United States Patent
Muni et al.

(10) Patent No.: US 7,410,480 B2
(45) Date of Patent: Aug. 12, 2008

(54) DEVICES AND METHODS FOR DELIVERING THERAPEUTIC SUBSTANCES FOR THE TREATMENT OF SINUSITIS AND OTHER DISORDERS

(75) Inventors: Ketan P. Muni, San Jose, CA (US); Hung V. Ha, San Jose, CA (US); Joshua Makower, Los Altos, CA (US); John H. Morriss, Portola Valley, CA (US); John Y. Chang, Mountain View, CA (US); William M. Facteau, Montain View, CA (US); Amrish Jayprakash Walke, Santa Clara, CA (US)

(73) Assignee: Acclarent, Inc., Menlo Park, CA (US)

( * ) Notice: Subject to any disclaimer, the term of this patent is extended or adjusted under 35 U.S.C. 154(b) by 158 days.

(21) Appl. No.: 11/234,395

(22) Filed: Sep. 23, 2005

(65) Prior Publication Data

US 2006/0106361 A1    May 18, 2006

Related U.S. Application Data

(63) Continuation-in-part of application No. 10/912,578, filed on Aug. 4, 2004, now Pat. No. 7,361,168, and a continuation-in-part of application No. 10/829,917, filed on Apr. 21, 2004.

(51) Int. Cl.
*A61M 31/00* (2006.01)
(52) U.S. Cl. ...................................................... 604/509
(58) Field of Classification Search .............. 604/890.1, 604/891.1, 93.1, 500, 506–510, 514, 516; 606/196; 128/204.12, 898; 424/434

See application file for complete search history.

(56) References Cited

U.S. PATENT DOCUMENTS 2,525,183 A    10/1950    Robison (Continued)

FOREIGN PATENT DOCUMENTS

DE    101 05 592    8/2002

(Continued)

OTHER PUBLICATIONS

Göttman, et al.; Balloon Dilation of Recurrent Ostial Occlusion of the frontal sinus; Abstract No. B-04353, European Congress of Radiology, Mar. 2001.

(Continued)

*Primary Examiner*—Kevin C. Sirmons
*Assistant Examiner*—Catherine N Witczak
(74) *Attorney, Agent, or Firm*—Robert D. Buyan; Stout, Uxa, Buyan & Mullins, LLP

(57) ABSTRACT

Devices and methods for delivering drugs and other therapeutic or diagnostic substances to desired locations within the bodies of human or non-human animal subjects. An implantable delivery device comprising a reservoir is initianlly attached to a deliver catheter or delivery tool and is introduced into the body and positioned at a desired site. A therapeutic or diagnostic substance is then introduced into the reservoir and the delivery catheter or deliver tool is then removed, leaving the implantable delivery device implanted within the body. The substance is then delivered from the reservoir at a rate that causes the desire diagnostic or therapeutic effect. Also provided are substance eluting stents that elute substance from a selected surface of the stent (e.g., the outer surface) but not from another surface of the stent (e.g., the inner surface).

25 Claims, 26 Drawing Sheets

U.S. PATENT DOCUMENTS

| | | |
|---|---|---|
| 3,173,418 A | 3/1965 | Baran |
| 3,469,578 A | 9/1969 | Bierman |
| 3,486,539 A | 12/1969 | Jacuzzi |
| 3,506,005 A | 4/1970 | Gilio et al. |
| 3,527,220 A | 9/1970 | Summers |
| 3,800,788 A | 4/1974 | White |
| 3,921,636 A | 11/1975 | Zaffaroni |
| 3,948,254 A | 4/1976 | Zaffaroni |
| 3,948,262 A | 4/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,102,342 A | 7/1978 | Akiyama et al. |
| 4,184,497 A | 1/1980 | Kolff et al. |
| 4,207,890 A | 6/1980 | Mamajek et al. |
| 4,217,898 A | 8/1980 | Theeuwes |
| 4,437,856 A | 3/1984 | Valli |
| 4,669,469 A | 6/1987 | Gifford et al. |
| 4,708,434 A | 11/1987 | Tsuno |
| 4,708,834 A | 11/1987 | Cohen et al. |
| 4,748,869 A | 6/1988 | Ohtsuka |
| 4,755,171 A | 7/1988 | Tennant |
| 4,815,478 A | 3/1989 | Buchbinder et al. |
| 4,851,228 A | 7/1989 | Zentner et al. |
| 4,898,577 A | 2/1990 | Badger et al. |
| 4,919,112 A | 4/1990 | Siegmund |
| 4,998,916 A | 3/1991 | Hammerslag et al. |
| 5,021,043 A | 6/1991 | Becker et al. |
| 5,026,384 A | 6/1991 | Farr et al. |
| 5,087,244 A | 2/1992 | Wolinsky et al. |
| 5,127,393 A | 7/1992 | McFarlin et al. |
| 5,152,747 A | 10/1992 | Olivier |
| 5,169,386 A | 12/1992 | Becker et al. |
| 5,171,233 A | 12/1992 | Amplatz et al. |
| 5,250,059 A | 10/1993 | Andreas et al. |
| 5,251,092 A | 10/1993 | Brady et al. |
| 5,255,679 A | 10/1993 | Imran |
| 5,263,926 A * | 11/1993 | Wilk .......................... 604/11 |
| 5,264,260 A | 11/1993 | Saab |
| 5,304,123 A | 4/1994 | Atala et al. |
| 5,343,865 A | 9/1994 | Gardineer et al. |
| 5,356,418 A | 10/1994 | Shturman |
| 5,368,566 A | 11/1994 | Crocker |
| 5,415,633 A | 5/1995 | Lazarus et al. |
| 5,425,370 A | 6/1995 | Vilkomerson |
| 5,439,446 A | 8/1995 | Barry |
| 5,465,717 A | 11/1995 | Imran et al. |
| 5,507,725 A | 4/1996 | Savage et al. |
| 5,512,055 A | 4/1996 | Domb et al. |
| 5,519,532 A | 5/1996 | Broome |
| 5,549,542 A | 8/1996 | Kovalcheck |
| 5,558,073 A | 9/1996 | Pomeranz et al. |
| 5,568,809 A | 10/1996 | Ben-haim |
| 5,578,007 A | 11/1996 | Imran |
| 5,634,908 A | 6/1997 | Loomas |
| 5,647,361 A | 7/1997 | Damadian |
| 5,656,030 A | 8/1997 | Hunjan et al. |
| 5,669,388 A | 9/1997 | Vilkomerson |
| 5,685,838 A | 11/1997 | Peters et al. |
| 5,685,847 A | 11/1997 | Barry |
| 5,693,065 A | 12/1997 | Rains, III |
| 5,694,945 A | 12/1997 | Ben-Haim |
| 5,713,946 A | 2/1998 | Ben-Haim |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,752,513 A | 5/1998 | Acker et al. |
| 5,775,327 A | 7/1998 | Randolph et al. |
| 5,792,100 A * | 8/1998 | Shantha ..................... 604/509 |
| 5,820,568 A | 10/1998 | Willis |
| 5,833,608 A | 11/1998 | Acker |
| 5,836,935 A | 11/1998 | Ashton et al. |
| 5,857,998 A | 1/1999 | Barry |
| 5,931,818 A | 8/1999 | Werp et al. |
| 5,935,061 A | 8/1999 | Acker et al. |
| 5,954,693 A | 9/1999 | Barry |
| 5,985,307 A | 11/1999 | Hanson et al. |
| 6,013,019 A | 1/2000 | Fischell et al. |
| 6,015,414 A | 1/2000 | Werp et al. |
| 6,048,299 A | 4/2000 | Hoffman |
| 6,113,567 A | 9/2000 | Becker .......................... 604/8 |
| 6,123,697 A * | 9/2000 | Shippert ..................... 604/514 |
| 6,148,823 A | 11/2000 | Hastings |
| 6,171,298 B1 | 1/2001 | Matsuura et al. |
| 6,171,303 B1 | 1/2001 | Ben-Haim et al. |
| 6,176,829 B1 | 1/2001 | Vilkomerson |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,195,225 B1 | 2/2001 | Komatsu et al. |
| 6,238,364 B1 | 5/2001 | Becker |
| 6,302,875 B1 | 10/2001 | Makower et al. |
| 6,340,360 B1 | 1/2002 | Lyles et al. |
| 6,375,615 B1 | 4/2002 | Flaherty et al. |
| 6,398,758 B1 | 6/2002 | Jacobsen et al. |
| 6,468,297 B1 | 10/2002 | Williams et al. |
| 6,500,130 B2 | 12/2002 | Kinsella et al. |
| 6,503,185 B1 | 1/2003 | Waksman et al. |
| 6,544,230 B1 | 4/2003 | Flaherty et al. |
| 6,551,239 B2 | 4/2003 | Renner et al. |
| 6,571,131 B1 | 5/2003 | Nguyen |
| 6,572,538 B2 | 6/2003 | Takase |
| 6,585,794 B2 | 7/2003 | Shimoda et al. |
| 6,638,233 B2 | 10/2003 | Corvi et al. |
| 6,669,689 B2 | 12/2003 | Lehmann et al. |
| 6,685,648 B2 | 2/2004 | Flaherty et al. |
| 6,716,813 B2 | 4/2004 | Lim et al. |
| D501,677 S | 2/2005 | Becker |
| 2001/0029317 A1 | 10/2001 | Hayakawa |
| 2003/0130598 A1 | 7/2003 | Manning et al. |
| 2003/0181827 A1 | 9/2003 | Hojeibane et al. |
| 2003/0185872 A1 | 10/2003 | Kochinke |
| 2004/0064083 A1 | 4/2004 | Becker |
| 2004/0064150 A1 | 4/2004 | Becker |
| 2004/0116958 A1 | 6/2004 | Gopferich et al. |
| 2006/0149310 A1 | 7/2006 | Becker ........................ 606/196 |
| 2007/0005094 A1 | 1/2007 | Eaton et al. |
| 2007/0073269 A1 | 3/2007 | Becker |

FOREIGN PATENT DOCUMENTS

| | | |
|---|---|---|
| WO | WO 92/15286 | 9/1992 |
| WO | WO 02/062269 | 8/2002 |
| WO | WO 2004/018980 | 3/2004 |

OTHER PUBLICATIONS

Göttman, et al., Balloon dilatation of recurrent ostial occlusion of the front sinus; ECR, Mar. 2, 2001.

Göttman, et al., Successful Treatment of Recurrent Post-operative Frontal Sinus Stenoses by Balloon Dilation; CIRSE, Oct. 5, 2002.

Göttman, et al., Balloon dilatation in the nasal cavity and paranasal sinuses; CIRSE, Sep. 25, 2004.

Robison, J. Matthews, M.D., Pressure Treatment of Purulent Maxillary Sinusitis, Texas State Journal of Medicine, May 1951, pp. 281-288.

Robison, J. Matthews, M.D., Pressure Treatment of Maxillary Sinusitis, J.A.M.A., May 31, 1952, pp. 436-440.

Strohm et al. Die Behandlung von Stenosen der oberen Luftwege mittels röntgenologisch gesteuerter Ballondilation Sep. 25, 1999.

Min, Yang-Gi et al., *Mucociliary Activity and Histopathology of Sinus Mucosa in Experimental Maxilary Sinusitis: A Comparison of Systemic Administration of Antibiotic and Antibiotic Delivery by Polylactic Acid Polymer*, Laryngoscope, Aug. 1995, 105:835-842.

Deutschmann, R. et al., *A Contribution to the Topical Treatment of [Maxillary] Sinusitis Preliminary Communication*, Stomat. DDR 26 (1976), 585-592.

Tarasov, D.I. et al., *Applications of Drugs Based on Polymers in the Treatment of Acute and Chronic Maxillary Sinusitis*, Vestn Otorinolaringol. (1978), vol. 6, pp. 45-47.

Chien, Y.W. et al., *Nasal Systemic Drug Delivery*, Drugs and the pharmaceutical sciences, vol. 39, pp. 60-63.

Croix, et al.; "Genes Expressed in Human Tumor Endothelium"; May 15, 2000; Science vol. 289 pp. 1197-1202.

Benninger, et al.; Adult Chronic Rhinosinustis: definitions, diagnosis, epidemiology, and pathophysiology; Arch Otolaryngol Head and Neck Surg; vol. 129, p. S1-S22; Sep. 2003.

Göttman, et al.; Balloon Dilation of Recurrent Ostial Occlusion of the frontal sinus; Abstract No. B-04353, European Congress of Radiology [date?].

Strohm et al. Die Behandlung von Stenosen der oberen Luftwege mittels röntgenologisch gesteurter Ballondilation Sep. 25, 1999.

Göttman, et al., Successful Treatment of Recurrent Post-operative Frontal Sinus Stenoses by Balloon Dilatation; CIRSE, Oct. 5, 2002.

Göttman, et al., Balloon dilatation of recurrent ostial occlusion of the front sinus; ECR, Mar. 2, 2001.

Göttman, et al., Balloon dilatation in the nasal cavity and paranasal sinuses; CIRSE, Sep. 25, 2004.

Davis, Greg E., et al., A Complication From Neurocranial Restructuring; Arch Otolaryngol Head Neck Surg; vol. 129, p. 472-474; Apr. 2003.

Robison, J. Matthews, M.D., Pressure Treatment of Purulent Maxillary Sinusitis, Texas State Journal of Medicine, May 1951, pp. 281-288.

Robison, J. Matthews, M.D., Pressure Treatment of Maxillary Sinusitis, J.A.M.A., May 31, 1952, pp. 436-440.

\* cited by examiner

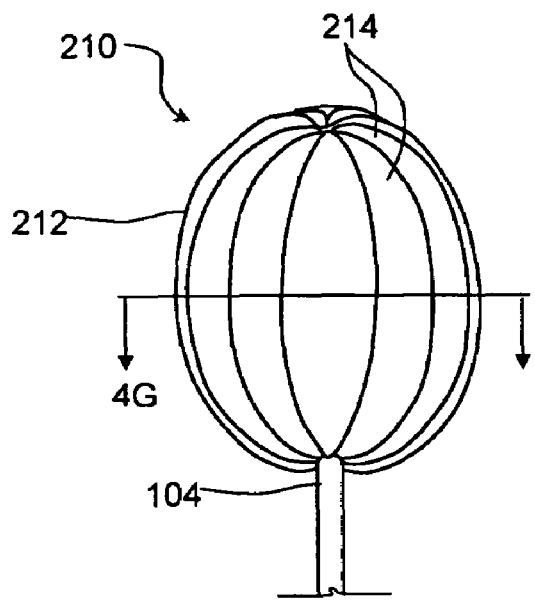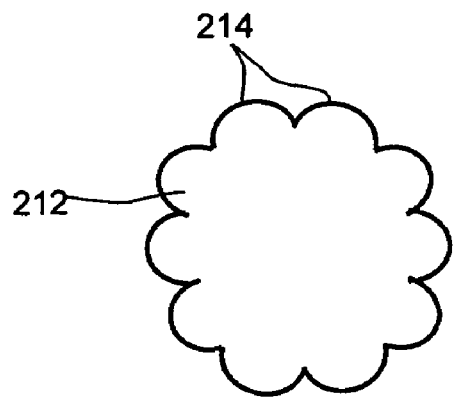
Fig. 4 F
Fig. 4 G
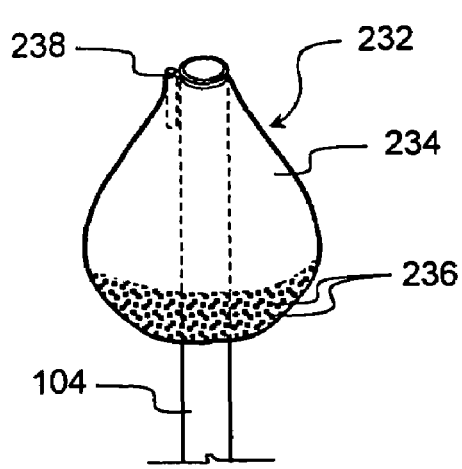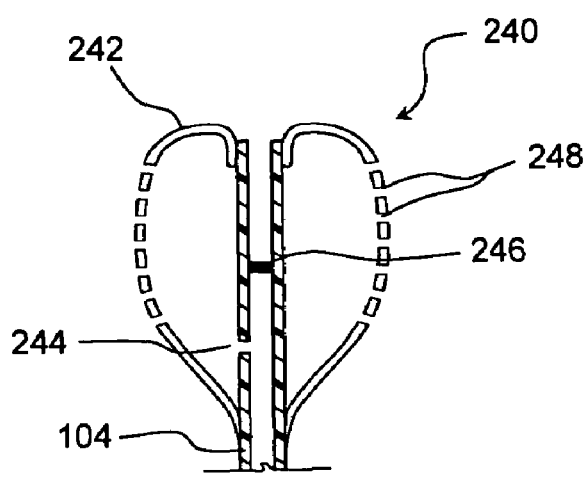
Fig. 4 K
Fig. 4 L

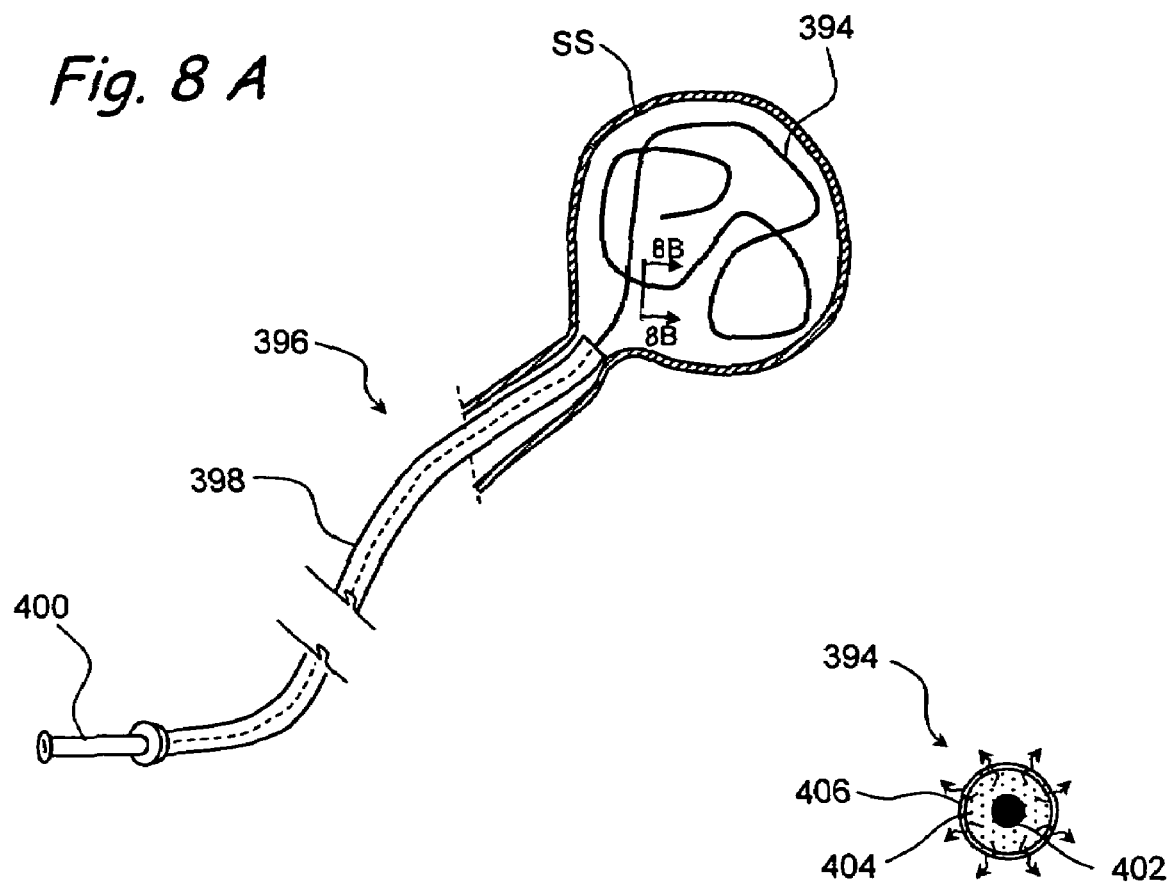

DEVICES AND METHODS FOR DELIVERING THERAPEUTIC SUBSTANCES FOR THE TREATMENT OF SINUSITIS AND OTHER DISORDERS

RELATED APPLICATIONS

This application is a continuation-in-part of copending U.S. patent application Ser. No. 10/829,917 entitled *Devices, Systems and Methods for Diagnosing and Treating Sinusitis and Other Disorders of the Ears, Nose and/or Throat* filed on Apr. 21, 2004 and 10/912,578 entitled *Implantable Device and Methods for Delivering Drugs and Other Substances to Treat Sinusitis and Other Disorders* filed on Aug. 4, 2004, each of which is expressly incorporated herein by reference.

FIELD OF THE INVENTION

The present invention relates generally to medical devices and methods and more particularly to substance delivering implants and methods for treating a broad range of disorders including but not limited to sinusitis and other ear, nose and throat disorders.

BACKGROUND

The paranasal sinuses are cavities formed within the bones of the face. The paranasal sinuses include frontal sinuses, ethmoid sinuses, sphenoid sinuses and maxillary sinuses. The paranasal sinuses are lined with mucous-producing epithelial tissue. Normally, mucous produced by the linings of the paranasal sinuses slowly drains out of each sinus through an opening known as an ostium, and into the nasopharnyx. Disorders that interfere with drainage of mucous (e.g., occlusion of the sinus ostia) can result in a reduced ability of the paranasal sinuses to function normally. This results in mucosal congestion within the paranasal sinuses. Such mucosal congestion of the sinuses can cause damage to the epithelium that lines the sinus with subsequent decreased oxygen tension and microbial growth (e.g., a sinus infection).

The nasal turbinates are three (or sometimes four) bony processes that extend inwardly from the lateral walls of the nasal cavity and are covered with mucosal tissue. These turbinates serve to increase the interior surface area of the nose and to impart warmth and moisture to air that is inhaled through the nose. The mucosal tissue that covers the turbinates is capable of becoming engorged with blood and swelling or becoming substantially devoid of blood and shrinking, in response to changes in physiologic or environmental conditions. The curved edge of each turbinate defines a passageway known as a meatus. For example, the inferior meatus is a passageway that passes beneath the inferior turbinate. Ducts, known as the nasolacrimal ducts, drain tears from the eyes into the nose through openings located within the inferior meatus. The middle meatus is a passageway that extends inferior to the middle turbinate. The middle meatus contains the semilunar hiatus, with openings or ostia leading into the maxillary, frontal, and anterior ethmoid sinuses. The superior meatus is located between the superior and medial turbinates.

Nasal polyps are benign masses that grow from the lining of the nose or paranasal sinuses. Nasal polyps often result from chronic allergic rhinitis or other chronic inflammation of the nasal mucosa. Nasal polyps are also common in children who suffer from cystic fibrosis. In cases where nasal polyps develop to a point where they obstruct normal drainage from the paranasal sinuses, they can cause sinusitis.

The term "sinusitis" refers generally to any inflammation or infection of the paranasal sinuses. Sinusitis can be caused by bacteria, viruses, fungi (molds), allergies or combinations thereof.

Various drugs have been used to treat sinusitis, including systemic antibiotics. Intranasal corticosteroid sprays and intranasal decongestant sprays and drops have also been used. However, the use of intranasal sprays and drops by most patients does not result in the drug actually entering the affected intranasal sinuses. Rather, such sprays and drops typically contact only tissues located within the nasal cavity. The introduction of drugs directly into the sinuses has been proposed by others, but has not become a widely used treatment technique. For example, United States Patent Application Publication 2004/0116958A1 (Gopferich et al.) describes a tubular sheath or "spacer" formed of biodegradable or non-biodegradable polymer that, prior to insertion in the patient's body, is loaded with a controlled amount of an active substance, such as a corticosteroid or anti-proliferative agent. Surgery is performed to create a fenestration in a frontal sinus and the sheath is inserted into such fenestration. Thereafter, the sheath which has been preloaded with the active substance is inserted into the surgically created fenestration where it a) deters closure of the surgically created fenestration, b) serves as a conduit to facilitate drainage from the sinus and d) delivers the active substance. The sheath of United States Patent Application Publication 2004/0116958A1 (Gopferich et al.) remains substantially in a single configuration (i.e., it does not transition between a collapsed configuration and an expanded configuration) although it may be coated with a material that swells when in contact with mucous or body fluid. In some embodiments, the sheath is formed of multiple layers of polymeric material, one or more of which is/are loaded with the active substance and one or more of which is/are free of the active substance. In other embodiments, the sheath has a "hollow body" which forms a reservoir system wherein the active substance is contained and a membrane which controls the release of the active substance from the reservoir. In some embodiments, the sheath may be anchored by causing the end of the sheath that extends into the sinus to swell or otherwise enlarge.

Also, Min, Yang-Gi, et al., *Mucociliary Activity and Histopathology of Sinus Mucosa in Experimental Maxilary Sinusitis: A Comparison of Systemic Administration of Antibiotic and Antibiotic Delivery by Polylactic Acid Polymer*, Laryngoscope, 105:835-842 (August 1995) describes experiments wherein experimental sinusitis was induced in three groups of rabbits by "pasting" the natural sinus ostia, forming an incision and small bore hole made in the anterior wall of the sinus, introducing pathogenic microbes through the bore hole and then closing the incision. Five days after introduction of the pathogenic microbes, the natural sinus ostia were reopened and the rabbits were divided into three (3) groups. Group 1 (control) received no treatment. Group 2 received repeated intramuscular injections of ampicillin. In the animals of Group 3, 1.5 cm×1.5 cm sheets of polylactic acid polymer (PLA) film containing ampicillin (0.326 mg/sheet) were rolled up and inserted through the natural ostia into the infected sinuses. Thereafter, measurements of mucocilliary transport speed were made and the tissues lining the affected sinuses were examined histopathologically. The authors concluded that the therapeutic effect observed in the animals that had received intrasinus implants of PLA/Ampicillin film (Group 3) was significantly better that that observed in the untreated control animals (Group 1) or those that has received repeated intramuscular doses of ampicillin (Group 2).

U.S. Pat. No. 3,948,254 (Zaffaroni) describes implantable drug delivery devices comprising a drug reservoir surrounded by a microporous wall. The reservoir may be formed of a solid drug carrier that is permeable to passage of the drug. The rate of passage of the drug through the wall may be slower than the rate at which the drug passes through the solid drug carrier that forms the reservoir. U.S. Pat. No. 3,948,254 (Zaffaroni) describes a number of applications for the implantable drug delivery devices including placement in a nasal passage. Specifically, U.S. Pat. No. 3,948,254 (Zaffaroni) claimed a nasal delivery device for dispensing a drug within a nasal passage at a controlled rate wherein the nasal device is comprised of (a) a wall defining the device dimensioned for insertion and placement within a nasal passage, with the wall formed of a nasal acceptable microporous material, (b) a reservoir surrounded by the wall and comprised of a solid carrier permeable to drug and containing drug in an amount sufficient for the device to meter it at a continuous and controlled rate for a prolonged period of time from the device, (c) a liquid medium permeable to the passage of drug by diffusion charged in the micropores, and (d) wherein the device releases drug when in a nasal environment by passage of drug from the carrier and through the liquid to the exterior of the device to produce a useful result. The entire disclosure of U.S. Pat. No. 3,948,254 (Zaffaroni) is expressly incorporated herein by reference.

Other publications have also reported that introduction of drugs directly into the paranasal sinuses is effective in the treatment of sinusitis. See,. Tarasov, D. I., et al., *Application of Drugs Based on Polymers in the Treatment of Acute and Chronic Maxillary Sinusitis*, Vestn Otorinolaringol. Vol. 6, Pages 45-7 (1978). Also, R. Deutschmann, et al., *A Contribution to the Topical Treatment of [Maxillary] Sinusitis Preliminary Communication*, Stomat. DDR 26 (1976), 585-592 describes the placement of a resorbable drug delivery depot within the maxillary sinus for the purposes of eluting drugs, specifically Chloramphenicol. In this clinical series a water soluble gelatin was used as carrier and was mixed with the drug prior to application and introduced as a mass into the sinus. Since the substance had little mechanical integrity and dissolved in a relatively short timeframe, to achieve a therapeutic effect, the author suggested that it must be instilled every 2 to 3 days. An alternative to gelatin could be a sponge loaded with the therapeutic substance as suggested in U.S. Pat. No. 6,398,758 (Jacobsen, et al.). In this patent directed at delivering a sustained release device against the wall of a blood vessel, a hollow cylindrical sponge is loaded with drug and pressed against the wall. This allows the drug to contact the wall while sustaining blood flow within the center of the lumen. Further, a skin is provided to direct the drug into the walls of the blood vessel and prevent drug from flowing into the lumen. While sponges loaded with drug at the time of their application do permit some degree of sustained release, the time required to load them also correlates closely the time over which they will elute substance. Thus, if delivery is required for a longer period of time additional mechanisms must be employed to regulate their release.

There are also several examples in the patent literature where various sustained release mechanisms have generally been proposed using systems with pre-incorporated drugs into matrices or polymers. These include U.S. Pat. No. 3,948, 254 (Zafferoni), US 2003/0185872A2 (Kochinke), WO 92/15286 (Shikani), and U.S. Pat. No. 5,512,055 (Domb, et al.). In general, these references discuss various materials and structures that may be used to construct sustained drug delivery vehicles and provide a good overview of the state of sustained drug delivery art. While helpful in laying out certain materials and schemes for creating sustained release systems for drugs, each of these references, however, do not describe specific methods, means or structures which would permit them to be easily adapted for intended uses in the targeted in this application.

Another common ear, nose and throat disorder is otitis media or inflammation of the middle ear. Most cases of otitis media are associated with some degree of Eustachian tube disfunction. Because air cannot adequately pass through the Eustachian tube into the middle ear, negative pressure can be created within the middle ear. This negative pressure may essentially pull or draw fluid out of the lining of the middle ear/mastoid, thereby resulting in an accumulation of fluid in the middle ear behind the eardrum. In some cases, fluid that accumulates within the middle ear can become infected. Several types of otitis have been identified. Serous otitis typically results from a fairly sudden obstruction of the Eustachian tube and is characterized by the collection of generally thin, clear fluid in the middle ear and mastoid. If this fluid does not clear within a few weeks, it is considered chronic serous otitis. Secretory otitis typically occurs in small children and is characterized by the collection of a thick fluid in the middle ear and mastoid. This thick fluid contains muccoid material that has been secreted by the mucous glands of the middle ear and also contains enzymes that can damage the small bones and other tissues of the middle ear. If left untreated, these enzymes can erode the bones enough to cause permanent hearing loss. Acute otitis media is characterized by the accumulation of pus in the middle ear and typically occurs in patients who have active respiratory infections which result in an abrupt obstruction of the Eustachian tube at the same time as infectious bacteria are present. Without antibiotic treatment, acute otitis of bacterial origin can cause perforation of the eardrum, with drainage of pus from the ear. Although the eardrum may heal after the infection has resolved, permanent damage to the middle ear and/or the inner ear can sometimes result from infections of this severity. Chronic otitis media is typically caused by a form of chronic mastoiditis and results in a chronic infection of the middle ear and mastoid cavity. Because the mastoid bone is involved, treatment with antibiotics administered by traditional routes of administration (i.v., i.m., oral, etc.) sometimes does not remove the infection from the bone and surgical removal of the infected mastoid bone may be necessary. A common complication associated with chronic otitis and mastoiditis is cholesteatoma. A cholesteatoma is a soft tissue sac that emanates from the eardrum and grows back into the middle ear or mastoid, thereby creating a mass of progressively increasing size which can destroy or damage the bones of the middle ear, the inner ear, the facial nerve and/or portions of the brain. Thus, the various forms of otits can be very serious if left untreated.

There remains a need in the art for the development of new devices and methods for delivering drugs and other therapeutic or diagnostic substances into paranasal sinuses, Eustachian tubes, middle ear and/or other locations within the body for the treatment of sinusitis, otitis or other diseases and disorders.

SUMMARY OF THE INVENTION

In accordance with the present invention there is provided a substance delivery device that generally comprises i) a removable portion comprising an elongate shaft having a lumen and a distal end and ii) an implantable portion comprising a substance delivery reservoir having a first configuration and a second configuration, said reservoir being in communication with the lumen of the removable portion such that a therapeutic or diagnostic substance, or a component thereof, may be introduced through the lumen and into the reservoir, said implantable portion being detachable from the removable portion such that the removable portion may be removed from the subject's body leaving the implantable portion within the subject's body. The reservoir may comprise a balloon or other vessel that expands or otherwise changes configuration when filled with the diagnostic or therapeutic substance. The removable portion may include a lumen, advanceable needle, injector or other substance introducing apparatus that is useable to introduce the desired substance, or a component thereof, into the reservoir after the reservoir has been introduced into the body. In addition to delivering the substance, all or part of the implantable portion of the device may function as a stent and/or scaffold and/or drain and/or vent.

Further in accordance with the present invention, there is provided a method for using a substance delivery device of the above-summarized character, such method generally comprising the steps of; i) introducing the substance delivery device into the subject's body while the reservoir is in a first configuration; ii) positioning the implantable portion at a desired location within the subject's body; iii) providing a therapeutic or diagnostic substance; iv) introducing the substance, or a component thereof, through the lumen and into the reservoir thereby causing the reservoir to assume the second configuration; v) detaching the removable portion from the implantable portion; and vi) removing the removable portion from the subject's body. In some embodiments of the method the substance delivery device is implanted within the ear, nose, throat or paranasal sinus of the subject, but such methods also have applicability in many other areas of the body.

Still further in accordance with the invention, there is provided a substance eluting implant (e.g., a stent) that generally comprises core that contains the substance, a layer on one side of the core through which the substance elutes and a layer on another side of the core through which substance does not elute. Thus, one surface (e.g., an outer tissue-contacting surface) of the implantable device may elute the substance while another surface (e.g., an inner or non-tissue contacting surface) does not elute the substance.

Still further in accordance with the present invention, there is provided a method for using a substance eluting implant of the above-summarized character, such method generally comprising the step of implanting the implat within the body of a human or non-human animal subject such that a substance eluting surface of the implant will elute the substance and a non-substance eluting surface of the implant will not elute any substantial amount of the substance.

Stull further aspects and details of the present invention willl be understood upon reading of the detailed description and examples set forth herebelow.

BRIEF DESCRIPTION OF THE DRAWINGS

FIG. 1A shows a perspective view of the sinus substance delivery device of FIG. 1.

FIGS. 1B and 1B' show side views of the deployment mechanism of the sinus substance delivery device of FIG. 1 in the un-deployed and deployed states respectively.

FIG. 1C shows a cross section through the plane 1C-1C of the delivery catheter of FIG. 1.

FIG. 1D-1F show various steps of introducing and deploying the substance delivery device of FIG. 1 into a paranasal sinus through the ostium of the paranasal sinus.

FIGS. 4A' through 4E' show a coronal view of a human head showing the various steps of an embodiment of a method of delivering an implantable substance delivery device to a Eustachian tube or middle ear of a patient.

FIG. 5A' shows a sectional view of the substance delivery device shown in FIG. 5A showing the pressure exerting mechanism exerting a pressure on a substance reservoir.

FIG. 6A' shows the substance delivery device of FIG. 6A deployed in a sphenoid sinus.

FIG. 6B' shows substance delivery device 610 of FIG. 6B deployed in a sphenoid sinus.

FIG. 6C' shows the substance delivery device of FIG. 6C deployed in a sphenoid sinus.

FIG. 6D' shows the substance delivery device of FIG. 6D deployed in a sphenoid sinus.

FIG. 6E' shows substance delivery device 352 of FIG. 6E deployed in a sphenoid sinus.

FIG. 8A shows an embodiment of an elongate substance delivery device comprising an elongate filament being introduced in a sphenoid sinus.

FIG. 8B shows a cross sectional view through a region of the substance delivery device of FIG. 8A through plane 8B-8B.

DETAILED DESCRIPTION

Figure 1:
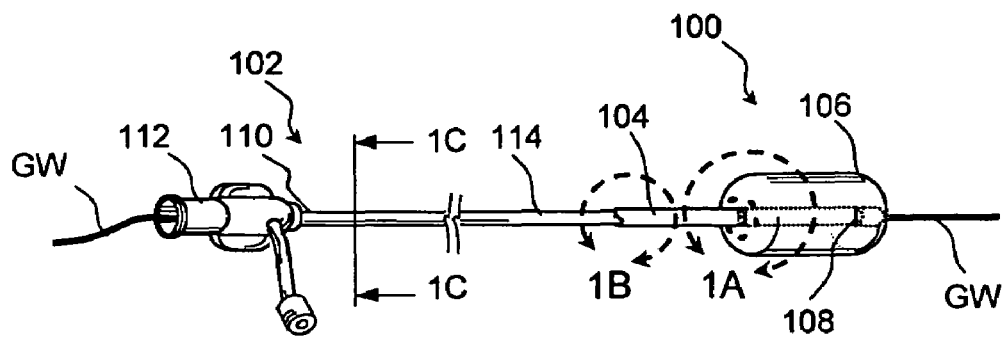
FIG. 1 shows a side view of an embodiment of a implantable sinus substance delivery device disposed on a removable delivery catheter
Figure 1:
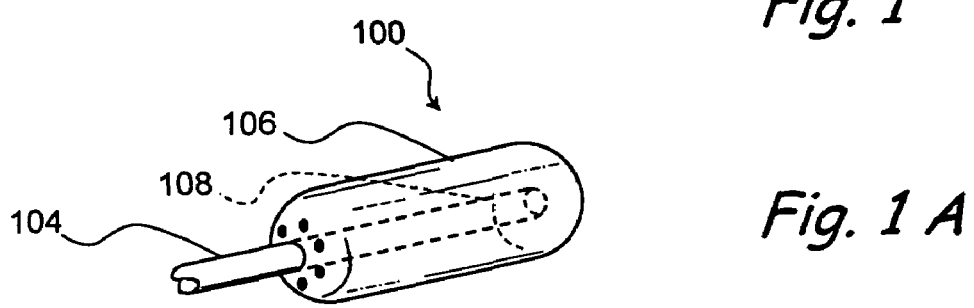
Figure 1:
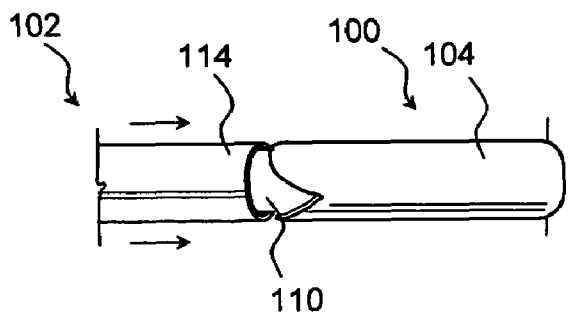
Figure 1:
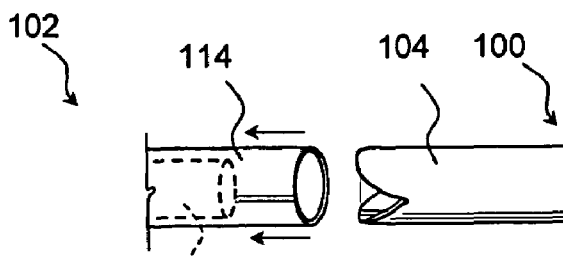
Figure 1:
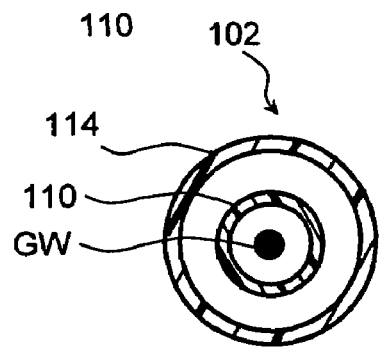
Figure 1:
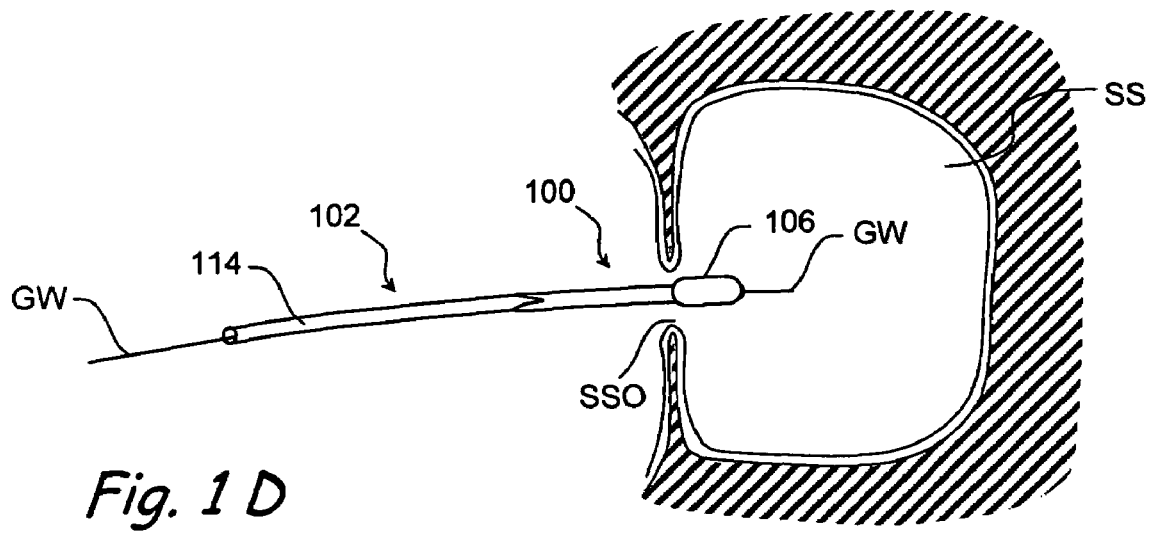
Figure 1:
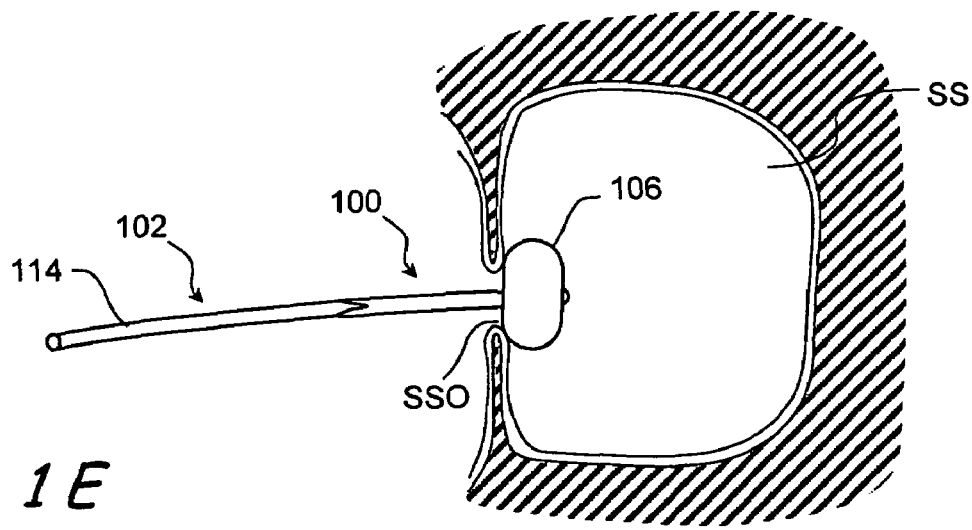
Figure 1:
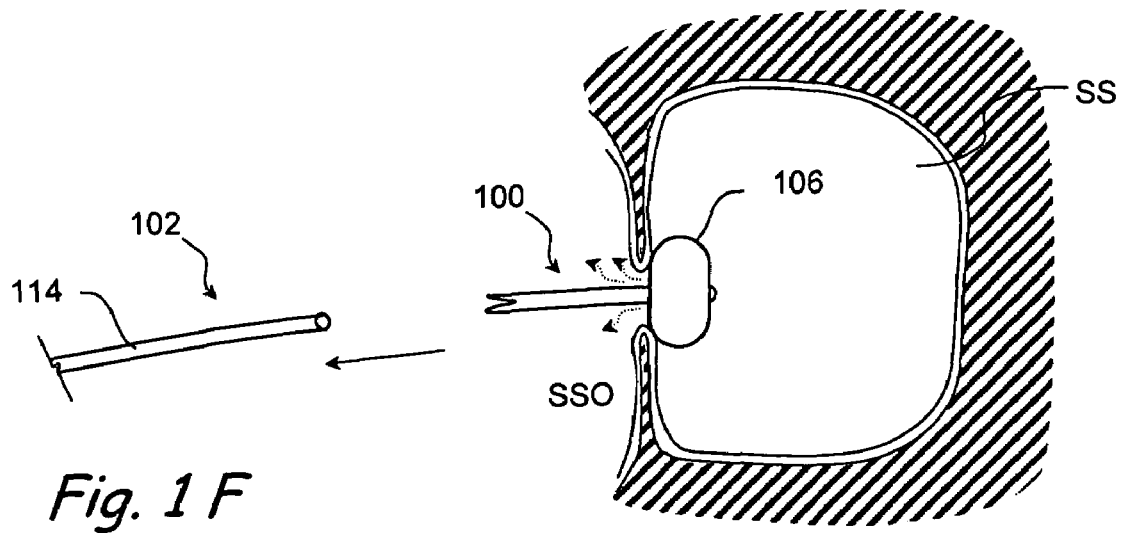

The following detailed description and the accompanying drawings are intended to describe some, but not necessarily all, examples or embodiments of the invention only. This detailed description and the accompanying drawings do not limit the scope of the invention in any way.

The present invention provides devices that may be positioned within naturally occurring or man-made anatomical cavities such as a nostrils, nasal cavities, nasal meatus, ostia or interior of paranasal sinuses, etc.; or naturally occurring or man-made passageways such as Eustachian tubes, naso-lachrymal ducts, etc. to deliver a diagnostic or therapeutic substance to tissues located adjacent to or near the implanted device. Certain non-limiting examples of the present invention are shown in FIGS. 1-11C and described in detail herebelow. Although certain examples shown in these drawings are targeted to the paranasal sinuses, regions of the middle ear, Eustachian tubes, etc., the devices and methods of the present invention are useable in a wide range of applications in various area of the body, including but not limited to natural or man made orifices and passageways such as naso-lachrymal ducts, subcutaneous locations, intravascular or intracardiac locations and locations within the gastrointestinal tract.

More specifically, one or more of the substance delivery devices disclosed herein may be positioned within natural or man-made openings to the frontal, maxillary, sphenoid, anterior or posterior Ethmoid sinuses; other cells or cavities; anatomical regions such as nostrils, nasal cavities, nasal meatus, etc.; and other passageways such as Eustachian tubes, naso-lachrymal ducts, etc. The step of placement of the substance delivery devices disclosed herein may be combined with a step of artificially creating an opening to an anatomical region. In one embodiment, the substance delivery devices disclosed herein are placed through natural or dilated anterior or posterior ethmoid sinus ostia or artificially created openings to the ethmoid sinuses. The artificially created openings may be created by punching a wall of the ethmoid sinuses. The sinus ostia or artificially created openings may be accessed through one or more artificially created holes in the ethmoid bulla. Such artificially created holes in the ethmoid bulla may be created by punching through the ethmoid bulla. In another embodiment, the substance delivery devices disclosed herein are placed through artificially created openings to the maxillary sinuses.

The term substance as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or non-fluid. For example, in some applications where it is desired to treat or prevent a microbial infection, the substance delivered may comprise a pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), an anesthetic agent with or without a vasoconstriction agents (e.g. Xylocaine with or without Epinephrine), an analgesic agent, an allergen or another substance that causes secretion of mucous by tissues, hemostatic agents to stop bleeding, anti-proliferative agents, cytotoxic agents e.g. alcohol, biological agents such as protein molecules, stem cells, genes or gene therapy preparations, viral vectors carrying proteins or nucleic acids such as DNA or mRNA coding for important therapeutic functions or substances, cauterizing agents e.g. silver nitrate, etc.

Some nonlimiting examples of antimicrobial agents that may be used in this invention include acyclovir, amantadine, rimantadine, oseltamivir, zanamivir, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillins including penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform); non-pathogenic or "friendly" microbes that cause the production of hydrogen peroxide or other substances that kill or inhibit the growth of pathogenic microbes (e.g., lactobacillus); antimicrobial proteins or peptides such as those described in U.S. Pat. No. 6,716,813 (Lin et al,.) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDs), analgesic agents or antipyretic agents. For example, corticosteroids that have previously administered by intranasal administration may be used, such as beclomethasone (Vancenase® or Beconase®), flunisolide (Nasalide®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor).

Additionally or alternatively, in some applications, such as those where it is desired to shrink mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine (Mucomyst™, Mucosil™) and guaifenesin.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chrom®) and nedocromil.

Additionally or alternatively, in some applications such as those where it is desired to prevent or inhibit the effect of histamine, the substances delivered in this invention may include various antihistamines such as azelastine (e.g., Astylin®), diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin/EDTA, hyaluronidase, and tosyllysylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anti-cholinergic agents that tend to dry up nasal secretions such as ipratropium (Atrovent Nasal®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include anti-tumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), anti-angiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired.

Additionally or alternatively to being combined with a device and/or a substance releasing modality, it may be ideal to position the device in a specific location upstream in the mucous flow path (i.e. frontal sinus or ethmoid cells). This could allow the deposition of fewer drug releasing devices, and permit the "bathing" of all the downstream tissues with the desired drug. This utilization of mucous as a carrier for the drug may be ideal, especially since the concentrations for the drug may be highest in regions where the mucous is retained; whereas non-diseased regions with good mucous flow will be less affected by the drug. This could be particularly useful in chronic sinusitis, or tumors where bringing the concentration of drug higher at those specific sites may have greater therapeutic benefit. In all such cases, local delivery will permit these drugs to have much less systemic impact. Further, it may be ideal to configure the composition of the drug or delivery system such that it maintains a loose affinity to the mucous permitting it to distribute evenly in the flow. For example, one or more substance eluting regions of a substance delivery device may be in physical contact with the mucous. Also, in some applications, rather than a drug, a solute such as a salt or other mucous soluble material may be positioned at a location whereby mucous will contact the substance and a quantity of the substance will become dissolved in the mucous thereby changing some property (e.g., pH, osmolarity, etc) of the mucous. In some cases, this technique may be used to render the mucous hyperosmolar so that the flowing mucous will draw water and/or other fluid from polyps, edematous mucosal tissue, etc., thereby providing a drying or desiccating therapeutic effect.

Additionally or alternatively to substances directed towards local delivery to affect changes within the sinus cavity, the nasal cavities provide unique access to the olfactory system and thus the brain. Any of the devices and methods described herein may also be used to deliver substances to the brain or alter the functioning of the olfactory system. Such examples include, the delivery of energy or the deposition of devices and/or substances and/or substance delivering implant(s) to occlude or alter olfactory perception, to suppress appetite or otherwise treat obesity, epilepsy (e.g., barbiturates such as phenobarbital or mephoobarbital; iminostilbenes such as carbamazepine and oxcarbazepine; succinimides such as ethylsuximide; valproic acid; benzodiazepines such as clonazepam, clorazepate, diazepam and lorazepam, gabapentin, lamotrigine, acetazolamide, felbamate, levetiraceam, tiagabine, topiramate, zonisamide, etc.), personality or mental disorders (e.g., antidepressants, anti-anxiety agents, antipsychotics, etc.), chronic pain, Parkinson's disease (e.g., dopamine receptor agonists such as bromocriptine, pergolide, ropinitrol and pramipexole; dopamine precursors such as levodopa; COMT inhibitors such as tolcapone and entacapone; selegiline; muscarinic receptor antagonists such as trihexyphenidyl, benztropine and diphenhydramine) and Alzheimer's disease, Huntington's disease or other dementias, disorders of cognition or chronic degenerative diseases (e.g. tacrine, donepezil, rivastigmine, galantamine, fluoxetine, carbamazepine, clozapine, clonazepam and proteins or genetic therapies that inhibit the formation of beta-amyloid plaques), etc.

The devices and methods disclosed herein may be used to deliver several combinations of two or more substances disclosed herein to a suitable target anatomical region. In one particular embodiment, the devices and methods disclosed herein are used to deliver a combination of an anti-inflammatory agent (e.g. a steroid or an NSAID) and a mucolytic agent.

The inner surface of some anatomical regions such as paranasal sinuses is lined by mucous. This mucous is continuously generated within the paranasal sinuses. Simultaneously, this mucous continuously flows out of paranasal sinuses through an ostium of the paranasal sinuses. Thus, a substance delivered to a paranasal sinus tends to be lost from the paranasal sinus along with the mucous flow. This reduces the net amount of the substance remaining in the paranasal sinus. Hence, there exists a need to replenish the substance delivered to the paranasal sinus to maintain an effective amount of the substance in the paranasal sinus. In order to address this need, one or more of the substance delivery devices disclosed herein may comprise one or more substance reservoirs to allow an effective amount of a substance to be delivered to target anatomical regions over an effective period of time.

Turning now to FIGS. 1-11C, it is to be understood that such figures show specific examples of the devices and methods of the present invention. Any elements, attributes, components, accessories or features of one embodiment or example shown in these figures may be eliminated from that embodiment or example, or may be included in any other embodiment or example, unless to do so would render the resultant embodiment or example unusable for its intended purpose.

FIG. 1 shows a side view of an embodiment of a device of the present invention comprising an implantable sinus substance delivery device 100 (e.g., an implantable portion) and a removable delivery catheter 102 (e.g, a removable portion). The implantable substance delivery device 100 is disposed on and is delivered by the removable delivery catheter 102. The implantable portion or substance delivery device 100 of this example comprises a tube or elongate shaft 104 and a substance reservoir 106 from which a desired substance is eluted or otherwise delivered. Elongate shaft 104 may be made of suitable biocompatible materials including, but not limited to Pebax, PEEK, Nylon, polyethylene, etc. This tube or elongate shaft may function and a stent and/or drain and/or vent when implanted. In this regard, the elongate shaft 104 may incorporate one or more lumens that are designed to allow drainage of secretions or other fluid substances and/or ventilation of air into desired anatomical regions (e.g., paranasal sinuses, the middle ear, etc. Additionally or alternatively, the elongate shaft 104 of the implantable portion 102 may incorporate a substance introducing lumenthat may be used to fill a reservoir 106 with fluid substances. As described in more detail below, the implantable drug delivery device 100 may also incorporate apparatus for preventing backflow of substance out of the reservoir 106 after the removable delivery catheter 102 has been removed. For example, the implantable substance delivery device 100 may have a substance introducing lumen through which a substance, or a component of the substance, may be introduced into the reservoir 106 and a check valve may be posititioned within that substance introducing lumen and/or within the reservoir to prevent backflow out of that substance introducing lumen. In this regard, the substance introducing lumen may have a collapsible or elastomeric region that is biased to a colosed or collapsed configuration so as to thereby act as a valve. This collapsible or elastomeric region will then expand when a user is filling reservoir 106 with a fluid substance under pressure, thus allowing the fluid substance to flow into the reservoir 106. The substance introducing lumen may be detachably connected to reservoir 106. In some embodiments, the reservoir 106 may be inflatable or expandable. In such inflatable or expandable embodiments, the reservoir 106 may be inflated or expanded in situ, after it has been implanted or otherwise positioned in a desired anatomical location. Thus the profile of substance delivery device 100 is reduced during the step of introducing reservoir 106 in the desired anatomical location. The lumen of elongate shaft 104 may be fitted with a one way valve to prevent unwanted drainage of a substance used to fill reservoir 106. In the embodiment shown in FIG. 1, reservoir 106 comprises a balloon that may be made from suitable biocompatible materials such as polyurethane, polyethylene, Nylon, etc. The balloon may comprise one or more pores or openings to allow delivery of the substance in reservoir 106 to the surrounding anatomy. Those pores or openings may be sized to allow the substance to be delivered from the reservoir 106 at a desired rate.

In some embodiments, a navigational marker 108 such as a radiopaque marker band may be present on elongate shaft 104 in the region enclosed by drug reservoir 106 or elsewhere on the device. The substance delivery device 100 is introduced into and advanced to a desired implantation site or target anatomy by the removable delivery catheter 102. The delivery catheter 102 provides support to substance delivery device 100 while substance delivery device 100 is introduced into and is delivered to the target anatomy. Delivery catheter 102 is also used to fill substance delivery device 100 with a suitable substance to be delivered to the anatomy. Delivery catheter 102 comprises an elongate shaft 110 that can be made of suitable biocompatible materials including, but not limited to metals e.g. stainless steel, titanium, Nickel-titanium alloy (e.g., Nitinol), etc.; polymers e.g. Pebax, PEEK, Nylon, polyethylene, etc. In one embodiment, the proximal end of elongate shaft 110 comprises a hub 112 such as a female luer hub. Hub 112 is in fluid communication with a lumen of elongate shaft 110. The lumen of elongate shaft 110 is in fluid communication with the lumen of elongate shaft 104 used to fill reservoir 106. The distal end of elongate shaft 110 is detachably connected to the proximal end of elongate shaft 104. Delivery catheter 102 may further comprise a deployment mechanism for deploying substance delivery device 100 in a desired location in the anatomy. In the embodiment shown in FIG. 1, the deployment mechanism comprises a pushing tube 114 that can be made of suitable biocompatible materials including, but not limited to Pebax, PEEK, Nylon, polyethylene, etc. Pushing tube 114 encloses and slides on elongate tube 110. To deploy substance delivery device 100 in the anatomy, a user pushes pushing tube 114 in the distal direction. The distal end of pushing tube 114 then pushes a proximal region of elongate shaft 104 that is detachably attached to elongate shaft 110. This causes substance delivery device 100 to detach from delivery catheter 102 thereby implant substance delivery device 100 in the anatomy. After implanting substance delivery device 100 in the anatomy, delivery catheter 102 is removed from the anatomy.

FIG. 1A shows a perspective view of sinus substance delivery device 100 showing elongate shaft 104 and reservoir 106 and navigational marker 108 located on elongate shaft 104.

FIGS. 1B and 1B' show side views of the deployment mechanism of the sinus substance delivery device of FIG. 1 in the un-deployed and deployed states respectively. In FIG. 1B, the proximal end of elongate shaft 104 of substance delivery device 100 is detachably attached to the distal end of elongate shaft 110 of delivery catheter 102. In FIG. 1B', a user pushes pushing tube 114 in the distal direction over elongate shaft 110. The distal end of pushing tube 114 pushes elongate shaft 104. This causes the proximal end of elongate shaft 104 to detach from the distal end of elongate shaft 110. This in turn causes substance delivery device 100 to detach from delivery catheter 102, thereby deploying substance delivery device 100 in the anatomy.

FIG. 1C shows a cross section through the plane 1C-1C of removable delivery catheter 102 of FIG. 1. FIG. 1C shows pushing tube 114 over the outer surface of elongate shaft 110. Elongate shaft 110 encloses guidewire GW.

FIG. 1D-1F show various steps of introducing and deploying implantable substance delivery device 100 of FIG. 1 into a paranasal sinus through the ostium of the paranasal sinus by a removable removable delivery catheter 102.

Substance delivery device 100 may be advanced into the anatomy by a suitable introducing device. In one embodiment, substance delivery device 100 is advanced into the anatomy by a suitable guidewire GW as shown in FIGS. 1D-1F. In this embodiment, substance delivery device 100 may comprise one or more arrangements to allow a user to introduce substance delivery device 100 over the guidewire. For example, elongate shaft 104 may comprise an end-to-end guidewire lumen, a rapid exchange guidewire lumen, etc. In another embodiment, substance delivery device 100 is advanced into the anatomy through a suitable guide catheter.

Substance delivery device 100 may be inserted into an anatomical region such as a paranasal sinus of a patient through natural ostia as shown in FIGS. 1D-1F or artificially created openings of the paranasal sinus. Substance delivery device 100 may be inserted into the paranasal sinus before or after sinus procedures such as FESS or Balloon Sinuplasty™. Substance delivery device 100 may be used to prevent or reduce post procedural scarring or adhesions and/or to provide ventilation or drainage of the paranasal sinus. Substance delivery device 100 may comprise one or more anchors or other retaining mechanisms to maintain the position of substance delivery device 100 inside the paranasal sinus for a desired treatment duration. In one embodiment, inflated reservoir 106 acts as an anchor. Substance delivery device 100 may be designed to allow its removal from the anatomy without the use of ionizing radiation such as X-rays.

The length of the implantable substance delivery device 100 may range from about 20 mm to about 80 mm. The combined length of the implantable substance delivery device 100 and the removable delivery catheter 102 may range from about 15 cm to about 135 cm.

In two preferred embodiments, the length of substance delivery device 100 is around 5 cm. Hub 112 is a luer lock. This enables a user to fill a suitable substance into reservoir 106 using a standard syringe. The length of the delivery system from the proximal end of the female luer hub to the distal end of elongate shaft 110 is around 25 cm. Elongate shaft 104 comprises a monorail guidewire lumen. The inner diameter of the monorail guidewire lumen is 0.037". This enables a user to introduce substance delivery device 100 into an anatomical region over a suitable 0.035" guidewire. Substance delivery device 100 and the suitable 0.035" guidewire may be delivered through a guide catheter of inner diameter 0.100". The filling lumen of elongate shaft 104 comprises a one way micro-valve. The micro-valve is located 4 cm proximal to the distal tip of elongate shaft 104. In an alternate embodiment, the micro-valve is located 1 cm from the distal tip of elongate shaft 104. Reservoir 106 comprises an elastomeric balloon of an inflated diameter ranging from 7-10 mm. The elastomeric balloon may be made from suitable biocompatible materials such as polyurethane, polyethylene, Nylon, etc. The length of the elastomeric balloon is about 10 mm. The inflated elastomeric balloon acts as an anchor to retain the position of substance delivery device 100 in the anatomy. A user may remove substance delivery device 100 from the anatomy by gently pulling substance delivery device 100. The elastomeric balloon is designed to touch at least one mucosal region in the anatomy after substance delivery device 100 is introduced in the anatomy. The substance stored in reservoir 106 may be delivered to the surrounding anatomy through one or more pores located on the elastomeric balloon or on a distal region of elongate shaft 104. In the first preferred embodiment, the elastomeric balloon comprises two micropores of diameter 80 microns. The two micropores are located on diagonally opposite regions on the proximal tapered region of the elastomeric balloon. This first embodiment was filled with 0.15 ml of distilled water at 37 degrees Celsius. The rate of delivery of the distilled water was measured in a shaker bath. This embodiment of substance delivery device 100 delivered 0.006-0.017 ml of distilled water in 15 hours. In the second preferred embodiment, a single micropore is located on elongate shaft 104. The micropore is located 10 mm from distal tip of elongate shaft 104. The micropore has a pore size of 60 microns. The elastomeric balloon was then inflated with 0.2 ml of a Kenalog solution and the rate of release of the Kenalog solution was measured in a shaker bath at a temperature of 37 degrees Celsius. This embodiment of substance delivery device 100 delivered 0.12-0.18 ml of the Kenalog solution in 24 hours.

The various substance delivery devices disclosed herein may comprise one or more substance reservoirs that are introduced in the anatomy in a first configuration. Thereafter, the reservoirs are filled with a suitable substance. This causes the reservoirs to assume a second configuration. Such a reservoir design having two or more configurations is especially useful to reduce the profile of the substance delivery devices while introducing the substance delivery devices in the anatomy. Such a reservoir design is also useful when the reservoir acts as an anchor. For example, substance delivery device 100 comprises an inflatable reservoir 106. Reservoir 106 is introduced in the anatomy in the un-inflated first configuration to reduce the profile of reservoir 106. Thereafter, reservoir 106 is filled with a suitable substance to cause reservoir 106 to assume a inflated second configuration.

The various substance delivery devices disclosed herein may comprise one or more rate limiting barriers to regulate the delivery of the substance stored in the substance delivery device to the surrounding anatomy. For example, in the two preferred embodiments described in the previous paragraph, the rate limiting barrier comprises micropores or apertures located on an elastomeric balloon or on a region of the elongate shaft. The rate limiting barrier may be designed to regulate the delivery of the substance to the surrounding anatomy based on one or more chemical or physical properties of the substance. In one embodiment, the rate limiting barrier is designed to regulate the delivery of the substance to the surrounding anatomy based on the viscosity of the substance. In another embodiment, the rate limiting barrier is designed to regulate the delivery of the substance to the surrounding anatomy based on the molecular weight of the substance. In another embodiment, the rate limiting barrier is designed to regulate the delivery of the substance to the surrounding anatomy based on the electric charge of the molecules of the substance. In another embodiment, the rate limiting barrier is designed to regulate the delivery of the substance to the surrounding anatomy based on the osmolarity or osmolality of the substance. In another embodiment, the rate limiting barrier is designed to regulate the delivery of the substance to the surrounding anatomy based on the hydrophobic or hydrophilic nature of the molecules of the substance. In another embodiment, the rate limiting barrier is designed to regulate the delivery of the substance to the surrounding anatomy based on the presence of a certain chemical group or atom in the molecules of the substance. In another embodiment, the rate limiting barrier is a semipermeable barrier. The semipermeable barrier may be designed to contain pores of a known size or a distribution of sizes to regulate the delivery of the substance to the surrounding anatomy.

The reservoirs of the substance delivery devices disclosed herein may be filled with a suitable substance through a substance introducing lumen located in a substance filling tube. Such a filling tube may be provided with one or more closure apparatus or mechanisms to prevent unwanted leakage of the suitable substance through the lumen of the substance filling tube. Examples of such closure apparatus or mechanisms include, but are not limited to valves such as check valves, clipping mechanisms, plugging mechanisms, etc. The valves may be located on the region of a substance delivery device enclosed by a substance reservoir. FIG. 2A shows a side view of an embodiment of a substance delivery device comprising a filling tube having a valve in the lumen of the filling tube. Substance delivery device 118 comprises a substance reservoir 106. Substance reservoir 106 comprises a means for delivering a stored substance to the surrounding anatomy over a period of time. In the example shown in FIG. 2A, substance reservoir 106 is an inflatable balloon. The length of the inflatable balloon may range from 10-20 mm. The inflated diameter of the inflatable balloon ranges preferably from 7-10 mm. The inflatable balloon is preferably made from suitable elastomeric materials including, but not limited to low density polyethylene, low durometer Pebax, polyurethane, etc. The inflatable balloon may also act as an anchor to secure the position of substance reservoir 106 in the anatomy. In one method embodiment, substance reservoir 106 is inserted into a paranasal sinus through the ostium of the paranasal sinus. Thereafter, the inflatable balloon is inflated with a suitable substance such that the size of the inflatable balloon is greater than the size of the ostium of the paranasal sinus. The inflatable balloon then acts as an anchor to secure the position of substance reservoir 106 in the paranasal sinus. Substance reservoir 106 can be filled with a suitable substance by an elongate shaft 104 that acts as a filling tube. Elongate shaft 104 comprises a lumen. A valve 120 is present in elongate shaft 104. In the example shown in FIG. 2A, valve 120 is a duck-bill valve. Other examples of valves include, but are not limited to flutter valves, slit valves, relief valves comprising springs, poppet valves, valves comprising one or more leaflets, etc. Valve 120 allows a user to fill substance reservoir 106. Valve 120 also prevents leakage of the substance from the proximal end of elongate shaft 104. In the example shown in FIG. 2A, valve 120 is located about 3-5 cm from the proximal end of substance reservoir 106. Alternatively, valve 120 may be located in the region of elongate shaft 104 enclosed by substance reservoir 106. In one embodiment, the outer diameter of the region of substance delivery device 118 enclosing valve 120 ranges from 2-3 mm. The proximal region of elongate shaft 104 may comprise a suitable hub such as a luer lock. Alternatively, the proximal region of elongate shaft 104 may be attached to the distal region of a second tube 122. The proximal region of second tube 122 may comprise a suitable hub such as a luer lock 112. Second tube 122 is made preferably from materials such as low density polyethylene, Pebax, polyurethane, etc. The attachment between the proximal region of elongate shaft 104 and the distal region of a second tube 122 may be non-detachable or detachable. In one embodiment the outer diameter of second tube 122 is around 0.05 inches and the inner diameter is around 0.03 inches. Substance delivery device 118 may comprise one or more mechanisms to allow substance delivery device 118 to be introduced in the anatomy along introducing devices. For example, substance delivery device 118 may be introduced over suitable guidewires, through suitable guide catheters, etc. In the example shown in FIG. 2A, substance delivery device 118 comprises a rapid exchange lumen located in a parallel tube 124 that is parallel to elongate shaft 104. In one embodiment, the outer diameter of parallel tube 124 is 0.048 inches and the inner diameter of parallel tube 124 is 0.038 inches. The distal region of the inflatable balloon is fixed to a region of parallel tube 124 to form a distal balloon joint. In one embodiment, the length of the distal balloon joint ranges from 2-3 mm. The proximal region of the inflatable balloon is fixed to a region of parallel tube 124 and elongate shaft 104 to form a proximal balloon joint. In one embodiment, the length of the proximal balloon joint ranges from 2-4 mm. The length from the proximal end of the proximal balloon joint till the proximal end of parallel tube 124 may range from 2-3 cm. The length from the distal end of the distal balloon joint till the distal end of parallel tube 124 may range from 1-2 mm. Substance delivery device 118 may comprise a marker 126 to allow the position of substance delivery device 118 to be tracked in the anatomy. In the example shown in FIG. 2A, marker 126 is a radiopaque marker. In one embodiment, the length of substance delivery device 118 measured from the distal end of hub 112 till the distal end of parallel tube 124 is around 30 cm.

FIGS. 2B, 2C and 2D show cross sections of the device shown in FIG. 2A through the planes 2B-2B, 2C-2C and 2D-2D respectively. FIG. 2B shows a cross section of parallel tube 124. FIG. 2C shows a cross section of elongate shaft 104 and parallel tube 124. FIG. 2D shows a cross section of second tube 122.

Various novel elastomeric sleeve valves may be used to design the various embodiments of the substance delivery devices disclosed herein. Such elastomeric sleeve valves comprise a sleeve or tubular piece of an elastomeric substance that is located near an opening of a reservoir filling lumen. For example, FIGS. 2E and 2F show longitudinal cross sections of an embodiment of a substance delivery device comprising a coaxial filling lumen and an elastomeric sleeve valve. Substance delivery device 127 of FIG. 2E comprises a substance reservoir 106. Substance reservoir 202 comprises a means for delivering a stored substance to the surrounding anatomy over a period of time. In the example shown in FIG. 2E, substance reservoir 106 is an inflatable balloon. The length of the inflatable balloon may range from 10-20 mm. The inflated diameter of the inflatable balloon ranges preferably from 7-10 mm. The inflatable balloon is preferably made from suitable elastomeric materials including, but not limited to low density polyethylene, low durometer Pebax, polyurethane, etc. Substance delivery device 126 further comprises a coaxial tube comprising an outer tube 128 and an inner tube 130.

Inner tube 130 comprises a first lumen 132. The region between outer tube 128 and inner tube 130 encloses a coaxial second lumen 134. In one embodiment, second lumen 134 is a substance introducing lumen used to fill substance reservoir 106. Substance delivery device 126 further comprises a second tube 136. The region between the inner surface of second tube 136 and the outer surface of the coaxial tube encloses a third lumen 138. In the example shown in FIG. 2E, the proximal end of the inflatable balloon is attached to a distal region of second tube. The distal end of the inflatable balloon is attached to the distal region of inner tube 130. Substance delivery device 126 further comprises a one way elastomeric sleeve valve 140. In the example shown in FIG. 2E, valve 140 comprises an elongate tube enclosing a lumen. Valve 140 can be made of suitable biocompatible materials including, but not limited to C-flex™, Kraton™, polyurethane, LDPE, silicone, EVA, other thermoplastic elastomers, etc. The one end of valve 140 is attached to a region of outer tube 128 by a fluid tight seal. The other end of valve is unattached. The unattached region of valve 140 compresses on the outer surface of inner tube 130 to seal second lumen 134 from third lumen 138. In FIG. 2E, a user introduces a substance in second lumen 134 under pressure. The pressure from second lumen 134 causes the unattached region of valve 140 to expand as shown. This causes the substance to travel from second lumen 134 to third lumen 138 and fills substance reservoir 106. In FIG. 2F, the introduction of the substance into second lumen 134 is stopped. This releases the pressure on valve 140 from second lumen 134. Thus the unattached region of valve 140 compresses on the outer surface of inner tube 130. This seals second lumen 134 from third lumen 138 thereby preventing the empting of substance reservoir 106 through second lumen 134. First lumen 132 may be used to introduce substance delivery device 126 into the anatomy over an introducing device such as a guidewire.

The shafts of the substance delivery devices disclosed herein may comprise one or more valves present in the region enclosed by a substance reservoir. For example, FIGS. 2G and 2H show cross sections through a portion of a substance delivery device comprising an elastomeric sleeve valve located in a region of an elongate shaft enclosed by a substance reservoir. FIG. 2G shows a cross sectional view of a drug delivery device 144 comprising an elongate shaft 104. Elongate shaft 104 may be made of suitable biocompatible materials including, but not limited to Pebax, PEEK, Nylon, polyethylene, etc. Elongate shaft 104 encloses a substance introducing lumen 146. A distal region of lumen 146 is blocked by a plug 148. A substance reservoir 106 is located on a distal region of elongate shaft 104. In the example shown in FIG. 2G, substance delivery reservoir comprises an inflatable balloon. The inflatable balloon is preferably made from suitable elastomeric materials including, but not limited to low density polyethylene, low durometer Pebax, polyurethane, etc. Lumen 146 is in fluid communication with substance reservoir 106 through one or more first openings or pores 150. Lumen 146 may thus be used to fill substance reservoir 106 with a suitable substance. An elastomeric sleeve valve 152 is located near first openings or pores 150. Valve 152 allows the substance to flow from lumen 146 to substance reservoir 106. Also, valve 152 prevents or substantially reduces the flow of the substance from substance reservoir 106 to lumen 146. In the example shown in FIG. 2G, valve 152 comprises an elongate tube enclosing a lumen. Valve 152 can be made of suitable biocompatible materials including, including, but not limited to C-flex™, Kraton™, polyurethane, LDPE, silicone, EVA, other thermoplastic elastomers, etc. One end of valve 152 is attached to a region of elongate tube 104 by a fluid tight seal. The other end of valve 152 is unattached. The unattached region of valve 152 compresses on the outer surface of elongate tube 104 to seal substance reservoir 106 from lumen 146. In FIG. 2G, a user introduces a substance in lumen 146 under pressure. The pressure from lumen 146 causes the unattached region of valve 152 to expand as shown. This causes the substance to flow from lumen 146 to substance reservoir 106. In FIG. 2H, the introduction of the substance into lumen 146 is stopped. This releases the pressure on valve 152 from lumen 146. Thus the unattached region of valve 152 compresses on the outer surface of elongate tube 104. This seals lumen 146 from substance reservoir 106 thereby preventing or substantially reducing the flow of the substance from substance reservoir 106 to lumen 146. The substance stored in substance reservoir 106 is controllably released into the surrounding anatomy through a substance delivery mechanism. In the example shown in FIGS. 2G and 2H, the substance delivery mechanism comprises one or more second openings or pores 154 that create a fluid communication between substance reservoir 106 and lumen 146. The distal end of lumen 146 opens into the surrounding anatomy such that the substance flows from substance reservoir 106 to the surrounding anatomy.

Valve 140 and valve 152 are made from elastomeric materials including, but not limited to C-flex™, Kraton™, polyurethane, LDPE, silicone, etc. The preferred thickness of the wall of the material of valve 140 and valve 152 ranges from 0.001 inches to 0.008 inches. The preferred longitudinal length of valve 140 and valve 152 ranges from 4-10 mm. Valve 140 and valve 152 may attached to an outer surface of elongate shafts by a variety of attachment mechanisms. In one embodiment of an attachment mechanism, valve 140 and valve 152 are attached by suitable biocompatible adhesives. For example, an adhesive such as Loctite® 4011 may be used with or without primers such as Loctite® 7701. In another embodiment of an attachment mechanism, valve 140 and valve 152 are attached to the elongate shafts by the mechanical compressive force of the elastomeric material of the valves. In another embodiment of an attachment mechanism, a cylindrical piece of heat-shrink tubing is clamped around a region of valve 140 and valve 152. In another embodiment of an attachment mechanism, valve 140 and valve 152 are laser welded or thermally welded to the elongate shafts.

The substance delivery devices disclosed herein may comprise various types of one-way valves. Such one-way valves enable a user to fill a substance reservoir with a suitable substance, but prevent the backflow of the substance after the substance reservoir is filled. For example, FIGS. 2I and 2J show a partial view of a region of a substance delivery device comprising a duck-bill valve. FIG. 2I shows a region of a substance delivery device 158 comprising a hollow shaft 160. Hollow shaft 160 encloses a reservoir filling lumen. A duck-bill valve 162 is provided in the substance introducing lumen of hollow shaft 160. Duck-bill valve 162 comprises a hollow body 164 enclosing a lumen. The distal region of duck-bill valve 162 comprises two or more leaflets 166. In one embodiment, duck-bill valve 162 is attached to the inner surface of hollow shaft 160 by a suitable adhesive. In the embodiment shown in FIG. 2I, the inner surface of hollow shaft 160 comprises a notch 168. An outer region of hollow body 164 of duck-bill valve 162 is locked in notch 168 as shown to attach duck-bill valve 162 to hollow shaft 160. Duck-bill valve 162 allows the flow of a fluid in the distal direction along hollow shaft 160. This enables a user to fill a substance reservoir located distal to duck-bill valve 162. Duck-bill valve 162 prevents the flow of fluid in the proximal direction along hollow shaft 160. This prevents unwanted drainage of the fluid substance from the substance reservoir through hollows shaft 160. FIG. 2J shows the step of filling the substance reservoir of substance delivery device 158 by inserting a fluid substance through the proximal region of hollow shaft 160. The pressure of the fluid substance spreads apart two or more leaflets 166 to open duck-bill valve 162. This allows the flow of the fluid substance in the distal direction along hollow shaft 160. Duck-bill valve 162 may be made from suitable biocompatible materials including, but not limited to elastomeric materials such as silicone, fluorosilicone, etc. In one embodiment, duck-bill valve 162 is made from a single piece of a suitable material.

Figure 2:
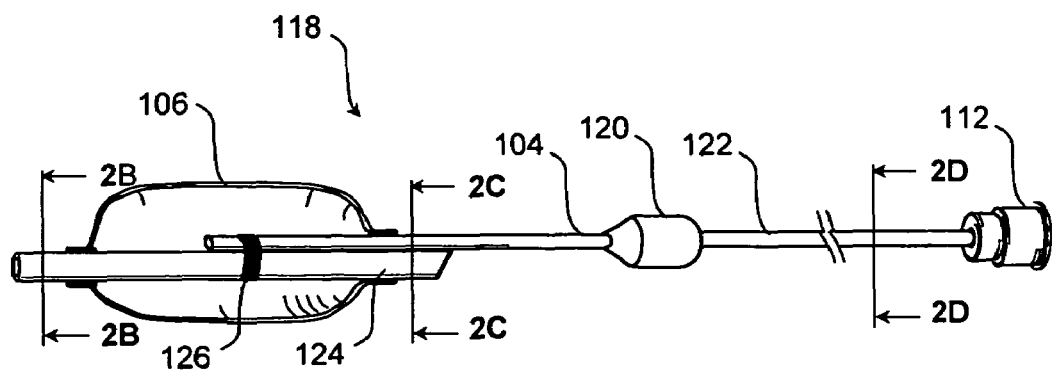
FIG. 2A shows a side view of an embodiment of a substance delivery device comprising a filling tube having a valve in the lumen of the filling tube.
FIGS. 2B, 2C and 2D show cross sections of the device shown in FIG. 2A through the planes 2B-2B, 2C-2C and 2D-2D respectively.
FIGS. 2E and 2F show longitudinal cross sections of an embodiment of a substance delivery device comprising a coaxial filling lumen and an elastomeric sleeve valve.
FIGS. 2G and 2H show cross sections through a portion of a substance delivery device comprising an elastomeric sleeve valve located in a region of an elongate shaft enclosed by a substance reservoir.
FIGS. 2I and 2J show a partial view of a region of a substance delivery device comprising a duck-bill valve.
FIGS. 2K and 2L show a partial view of a region of a substance delivery device comprising a dome valve.
FIGS. 2M and 2N show longitudinal sections through the filling mechanism of an embodiment of a substance delivery device comprising a self-sealing membrane.
FIGS. 2O and 2P show longitudinal sectional views of a region of an embodiment of a substance delivery device comprising a plugging mechanism.
Figure 2:
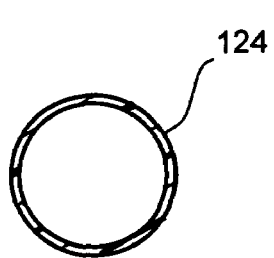
Figure 2:
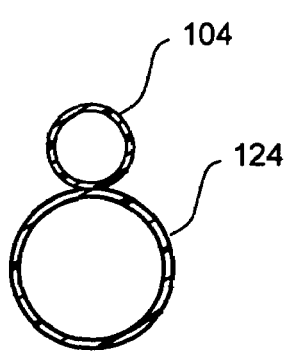
Figure 2:
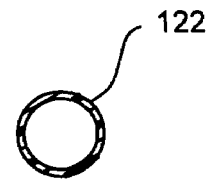
Figure 2:
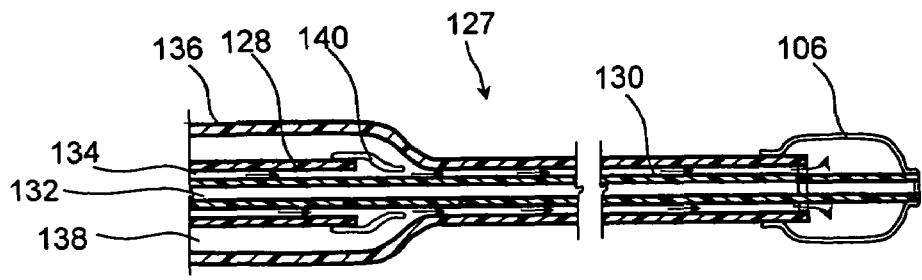
Figure 2:
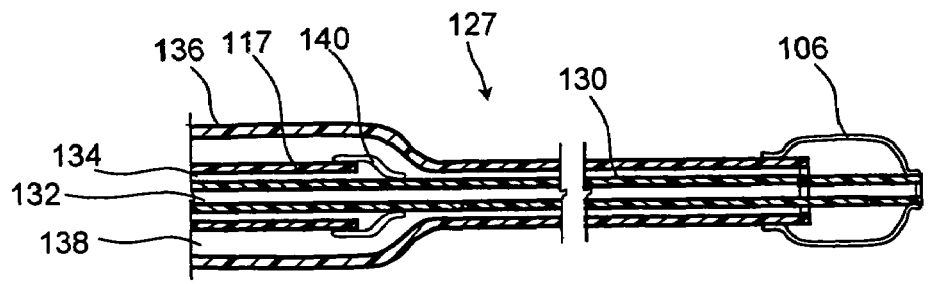
Figure 2:
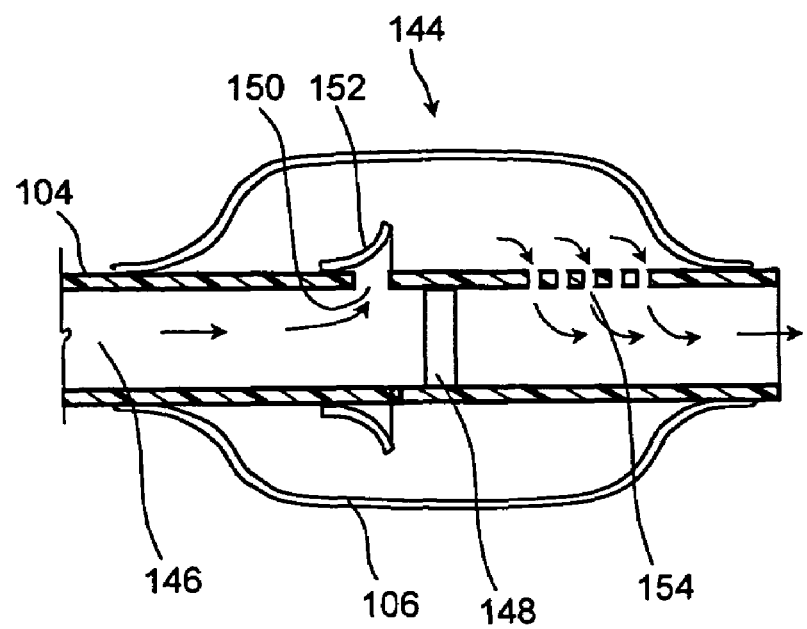
Figure 2:
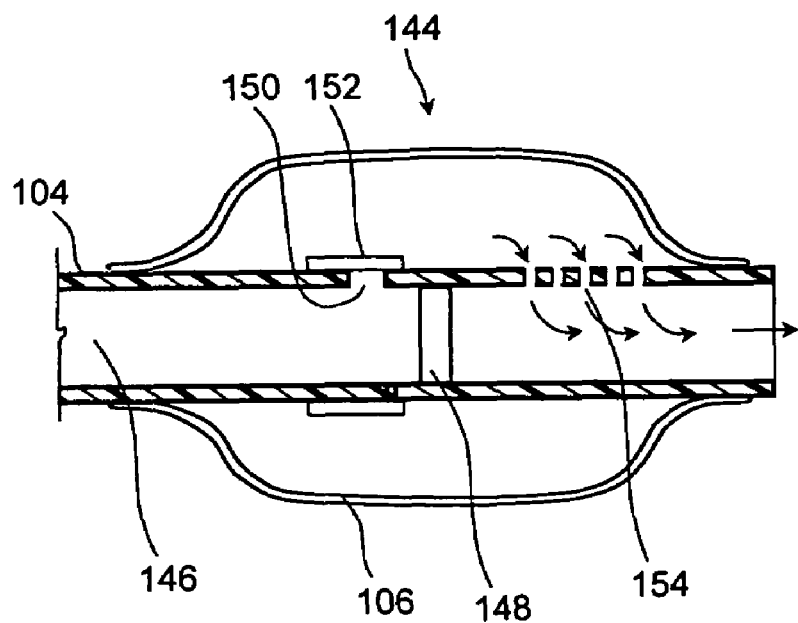
Figure 2:
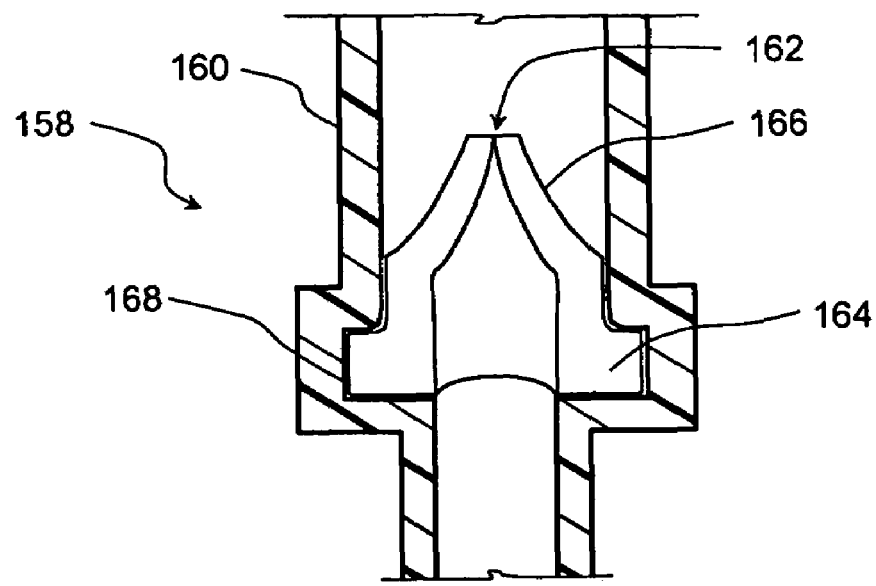
Figure 2:
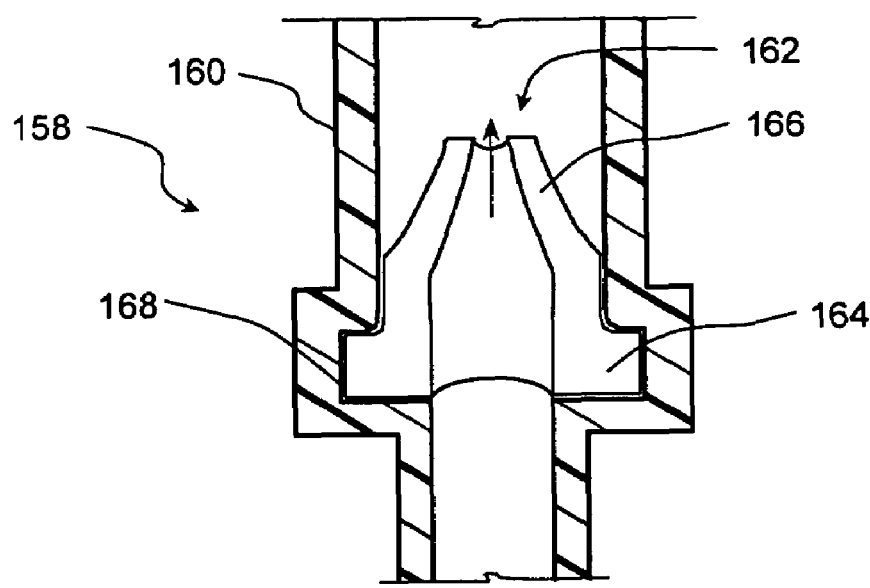
Figure 2K:
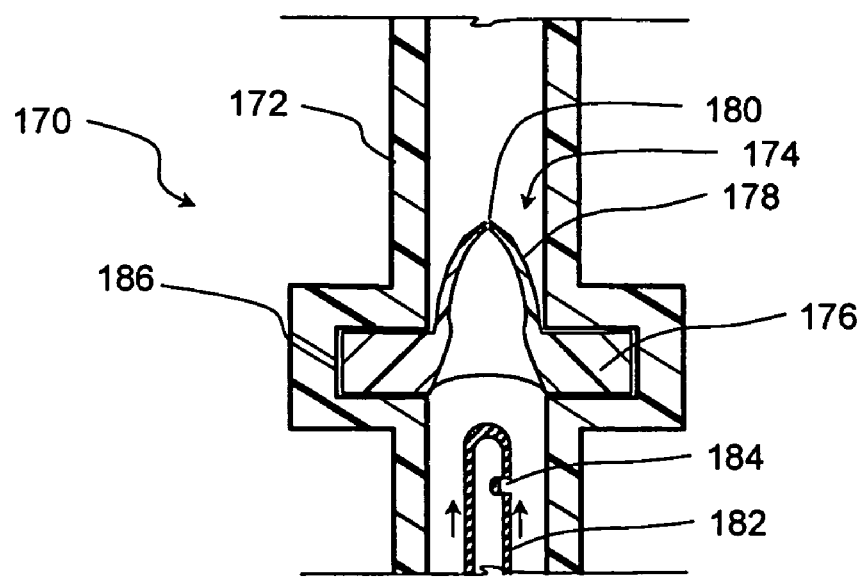
Figure 2L:
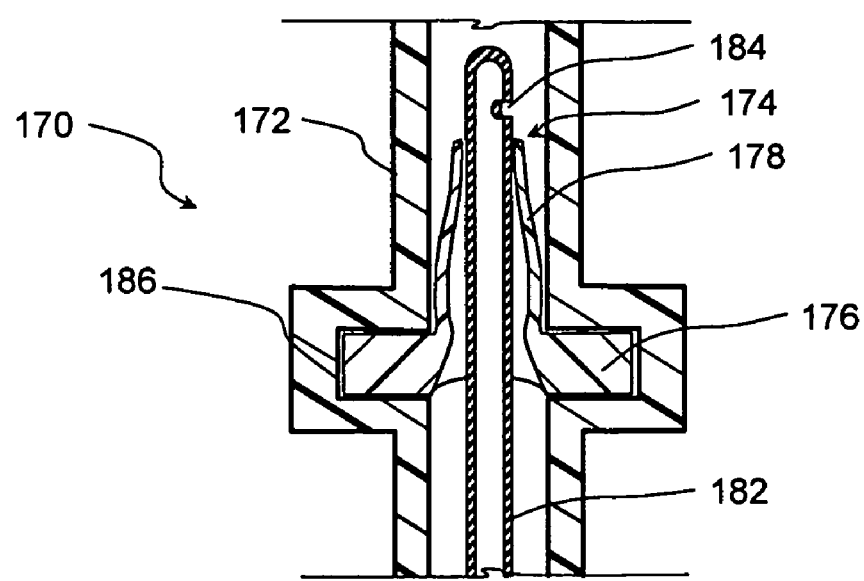
Figure 2:
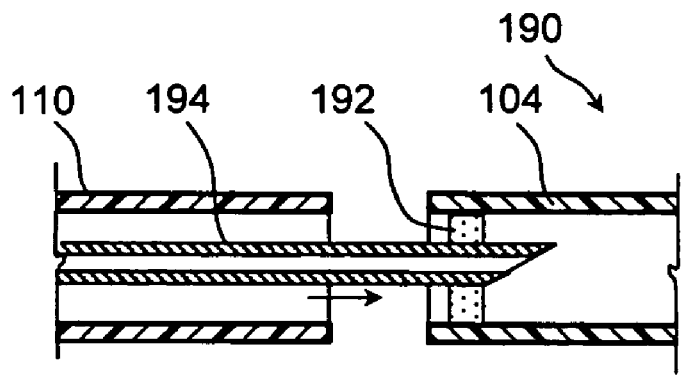
Figure 2:
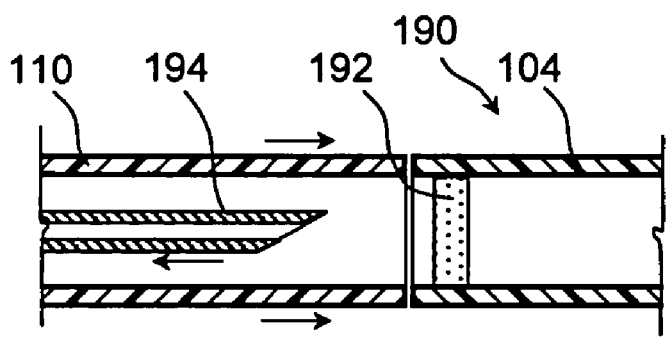
Figure 2:
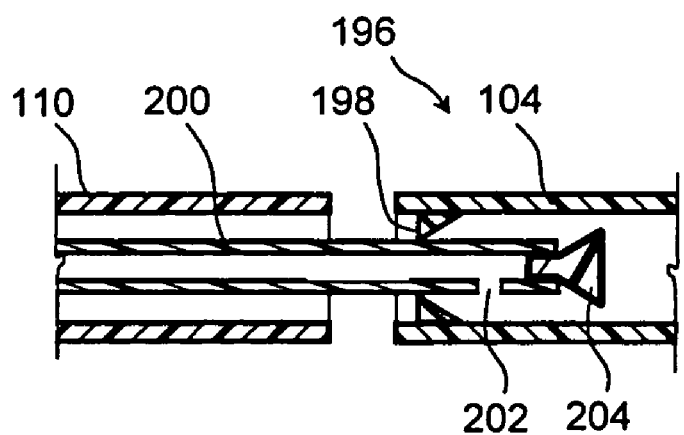
Figure 2:
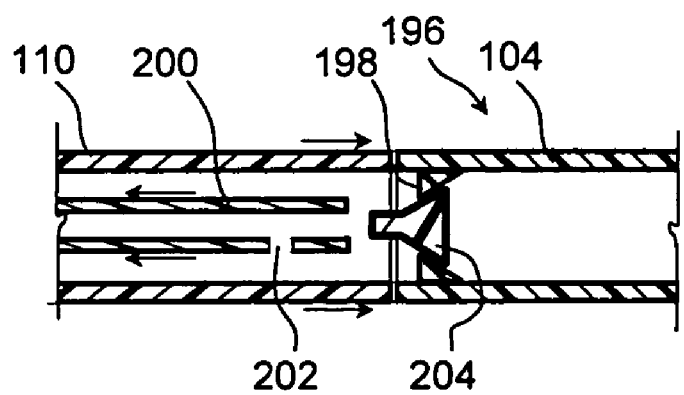
Figure 3:
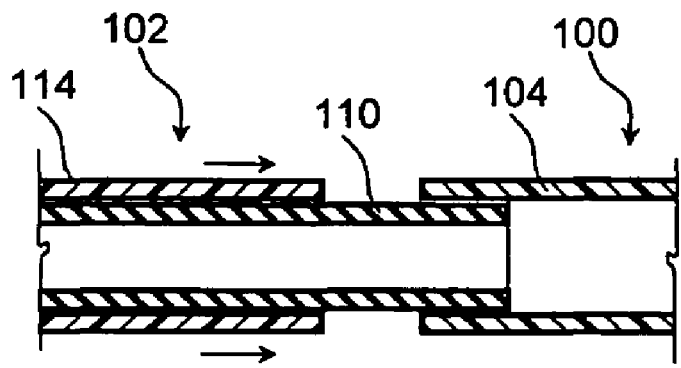
FIGS. 3A and 3B show a longitudinal section through a proximal region of a substance delivery device deployed by a sliding tube.
Figure 3:
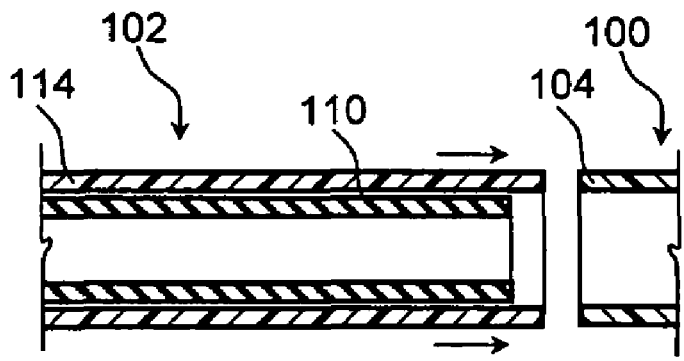

FIGS. 2K and 2L show a partial view of a region of a substance delivery device comprising a dome valve. FIG. 2K shows a region of a substance delivery device 170 comprising a hollow shaft 172. Hollow shaft 172 encloses a reservoir filling lumen. A dome valve 174 is provided in the lumen of hollow shaft 172. Dome valve 174 comprises a hollow body 176 enclosing a lumen. The distal region of dome valve 174 comprises a dome 178. One or more slits 180 are located in the distal most region of dome 178. To introduce a fluid substance in the lumen of hollow shaft 172 distal to dome valve 174, a user inserts an injecting device through slits 180 as shown in FIG. 2L. In the embodiment shown in FIGS. 2K and 2L, the injecting device comprises a hollow shaft 182 enclosing a lumen. Hollow shaft 182 comprises an atraumatic distal end. Hollow shaft 182 further comprises an opening or pore 184 that creates a fluid communication between the lumen of hollow shaft 182 and the exterior of hollow shaft 182. Slits 180 allow the passage of the injecting device 182 through them while maintaining a substantial fluid seal around the injecting device. The user can then introduce the fluid substance through the lumen of the injecting device to fill a substance reservoir located distal to dome valve 174. After the injecting device is withdrawn, dome valve 174 prevents the flow of fluid in the proximal direction along hollow shaft 172. This prevents unwanted drainage of the fluid substance from the substance reservoir through hollows shaft 172. In one embodiment, dome valve 174 is attached to the inner surface of hollow shaft 172 by a suitable adhesive. In the embodiment shown in FIGS. 2K and 2L, the inner surface of hollow shaft 172 comprises a notch 186. An outer region of hollow body 176 of dome valve 174 is locked in notch 186 as shown to attach dome valve 174 to hollow shaft 172. Dome valve 174 may be made from suitable biocompatible materials including, but not limited to elastomeric materials such as silicone, fluorosilicone, etc. In one embodiment, dome valve 174 is made from a single piece of a suitable material.

Similarly, substance delivery devices disclosed herein may comprise a variety of valves to allow a user to fill a substance reservoir located distal to the valves while preventing unwanted drainage of the fluid substance from the substance reservoir. Examples of such valves include, but are not limited to cross slit valves, umbrella valves, combinations of umbrella valve and duck-bill valve, valve balls, etc.

The shafts of the substance delivery devices disclosed herein may comprise various filling mechanisms to fill one or more substance reservoirs located distal to the filling mechanisms without leakage of the substance from the shafts. Such filling mechanisms may comprise a self-sealing membrane located proximal to the substance reservoirs. For example, FIGS. 2M and 2N show longitudinal sections through the filling mechanism of an embodiment of a substance delivery device comprising a self-sealing membrane. Substance delivery device 190 of FIGS. 2M and 2N comprises a hollow shaft 104. Hollow shaft 104 encloses a reservoir filling lumen. A proximal region of the lumen of hollow shaft 104 is plugged by a self sealing membrane 192. Self-sealing membrane 192 may be made of suitable biocompatible materials including, but not limited to silicone elastomers. Substance delivery device 190 further comprises a substance reservoir located distal to self sealing membrane 192. In FIG. 2M, substance delivery device 190 is introduced into the anatomy. In the embodiment shown in FIGS. 2M and 2N, substance delivery device 190 is introduced into the anatomy by a proximal shaft 110 that pushes hollow shaft 104 in the distal direction. Proximal shaft 110 comprises a lumen. An injecting device 194 is introduced through the lumen of proximal shaft 110. The distal tip of injecting device 194 punctures self-sealing membrane 192 and enters the region distal to self-sealing membrane 192. Self-sealing membrane 192 allows the passage of injecting device 194 while maintaining a substantial fluid seal around injecting device 194. Injecting device 194 may thereafter be used to introduce a fluid substance in the region distal to self-sealing membrane 192. Thus, injecting device 194 may be used to fill a substance reservoir located distal to self-sealing membrane 192. In FIG. 2N, injecting device 194 is pulled in the proximal direction and removed from self-sealing membrane 192. The area where injecting device 194 had punctured self-sealing membrane 192 seals itself due to the self-sealing property of self-sealing membrane 192. This prevents unwanted drainage of the fluid substance through the proximal end of hollow shaft 104.

The substance delivery devices disclosed herein may comprise various plugging mechanisms to plug a lumen of a filling lumen after filling a substance reservoir through the filling lumen. For example, FIGS. 2O and 2P show longitudinal sectional views of a region of an embodiment of a substance delivery device comprising a plugging mechanism. Substance delivery device 196 of FIGS. 2O and 2P comprises an elongate shaft 104 enclosing a reservoir filling lumen. The filling lumen may be used to fill one or more substance reservoirs located in the distal region of elongate shaft 104. A proximal region of elongate shaft 104 comprises a port 198 enclosing a lumen. In one embodiment, port 198 is made by locally reducing the diameter of elongate shaft 104. In another embodiment, port 198 is made of suitable biocompatible materials including, but not limited to silicone rubber, thermoplastic elastomers, etc. An injecting tube 200 is inserted through port 198. The outer diameter of injecting tube 200 is approximately equal to the inner diameter of the lumen enclosed by port 198. This creates a substantial fluid seal between the outer surface of injecting tube 200 and the inner surface of the lumen enclosed by port 198. Injecting tube 200 encloses a lumen that is in fluid communication with the exterior of injecting tube 200 through an opening or pore 202. The distal end of the lumen of injecting tube 200 is plugged by a suitable plug 204. Plug 204 is frictionally attached to a surface of injecting tube 200. The outer diameter of plug 204 is greater than the inner diameter of the lumen enclosed by port 198. Plug 204 may be made of suitable biocompatible materials including, but not limited to silicone rubber, thermoplastic elastomers, etc. In FIG. 2O, substance delivery device 196 is introduced into the anatomy. In the embodiment shown in FIGS. 2O and 2P, substance delivery device 196 is introduced into the anatomy by a proximal shaft 110 that pushes elongate shaft 104 in the distal direction. In FIG. 2O, a user injects a fluid substance through injecting device 200 in the region distal to port 198. This step may be used to fill a substance reservoir located distal to port 198. In FIG. 2P, the user pulls injecting device 200 in the proximal direction. This causes plug 204 to plug the lumen enclosed by port 198 as shown in FIG. 2P. When injecting device 200 is pulled further in the proximal direction, plug 204 detaches from injecting device 200. Thus the proximal end of the filling lumen is plugged by plug 204. This prevents or reduces leakage of the fluid substance through the proximal end of the filling lumen. Similarly, various other embodiments of plugging mechanisms may be used to prevent or reduce leakage of the fluid substance through the proximal end of the filling lumen.

In an alternate embodiment, plug 204 is located on the inner surface of the filling lumen of elongate shaft 104. Plug 204 comprises a swellable material that swells and increase in volume on coming into contact with the fluid substance. Plug 204 then occludes the filling lumen of elongate shaft 104 thereby preventing the leakage of the fluid substance from the proximal end of elongate shaft 104.

The substance delivery devices disclosed herein may be introduced into the anatomy by a variety of introducing devices comprising means for controllably deploying the substance delivery devices from the introducing devices. For example, FIGS. 3A and 3B show a longitudinal section through a proximal region of a substance delivery device deployed by a pushing tube similar to pushing tube 114 of FIG. 1. FIG. 3A shows the proximal region of a substance delivery device 100. In the embodiment substance delivery device comprises an elongate shaft 104 comprising a reservoir filling lumen. Elongate shaft 104 may be constructed from suitable biocompatible materials including, but not limited to metals, polymers, etc. The proximal region of elongate shaft 104 slides over the distal region of an elongate shaft 110 of an introducing device 102. The inner surface of elongate shaft 104 frictionally attaches to the outer surface of elongate shaft 110. This frictional attachment is strong enough to prevent detachment of substance delivery device 100 from introducing device 102 while inserting and navigating substance delivery device 100 through the anatomy. A pushing tube 114 slides on the outer surface of elongate shaft 110 proximal to the proximal end of elongate shaft 104. Pushing tube 114 can be moved over the outer surface of elongate shaft 110 by a user. In the step of deploying substance delivery device 100 from introducing device 102, the user pushes pushing tube 114 over the outer surface of elongate shaft 110 in the distal direction as shown in FIG. 3B. The distal end of pushing tube 114 pushes the proximal end of elongate shaft 104 to overcome the frictional attachment between the inner surface of elongate shaft 104 and the outer surface of elongate shaft 110. This causes elongate shaft 104 to be released from elongate shaft 110. Thereby, substance delivery device 100 is deployed from introducing device 102.

In an alternate means for controllably deploying the substance delivery devices, a substance delivery device is deployed by withdrawing a filling device from the substance delivery device. Three embodiments of this mechanism are illustrated in FIGS. 2K-2L, 2M-2N and 2O-2P.

In an alternate means for controllably deploying the substance delivery devices, the substance delivery devices are deployed by cutting or severing a region of the substance delivery devices. This causes the portion of the substance delivery device distal to the severed region to be deployed in the anatomy.

Figure 4:
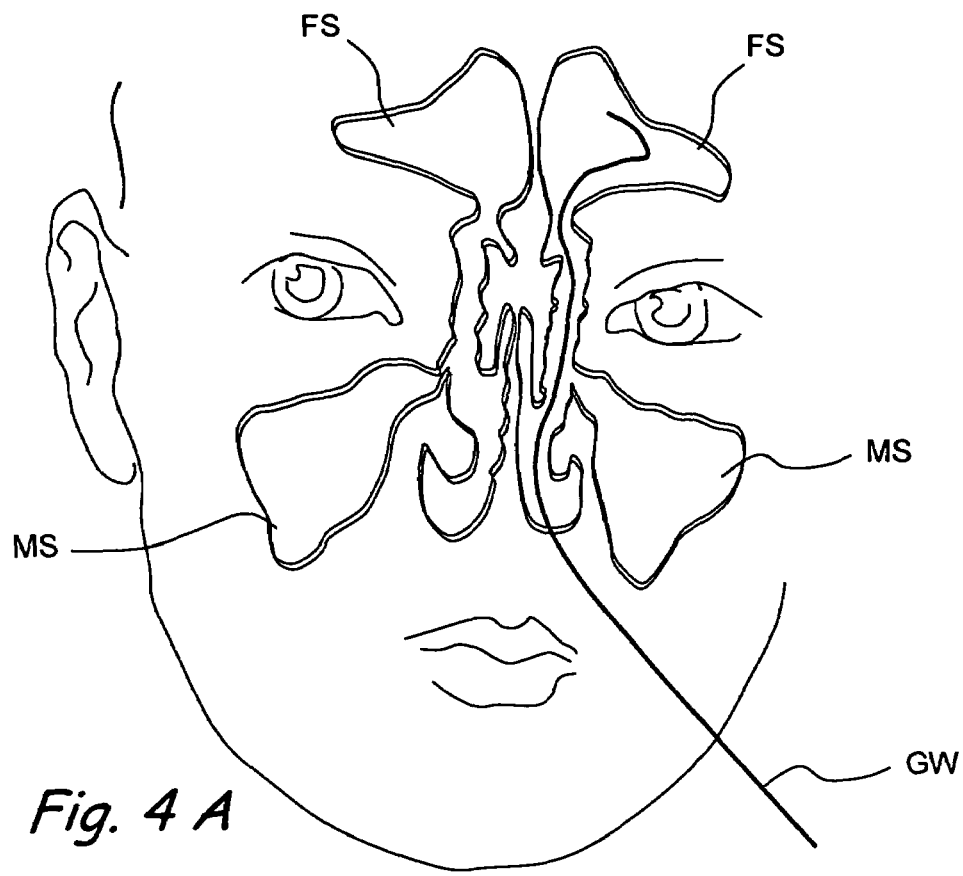
FIGS. 4A through 4E show a coronal view of a human head showing the various steps of a method of delivering an implantable substance delivery device to one of the paranasal sinuses of a patient.
FIG. 4F shows a region of a substance delivery device comprising an inflatable balloon comprising two or more lobes.
FIG. 4G shows a cross section of the balloon shown in FIG. 4F through the plane 4G-4G.
FIG. 4H shows a perspective view of an embodiment of an inflatable substance reservoir comprising a spiral inflatable balloon.
FIG. 4I shows a perspective view of a region of a substance delivery device comprising an inflatable balloon having one or more radial protrusions.
FIG. 4J shows a perspective view of a region of a substance delivery device comprising an inflatable balloon oriented transversely to the axis of the substance delivery device.
FIG. 4K shows a substance delivery device comprising an inflatable balloon that acts as a substance reservoir.
FIG. 4L shows a section through a substance delivery device comprising an inflatable substance delivery reservoir shaped to produce an atraumatic distal end.
FIG. 4M shows a cross section through a substance delivery device comprising two substance reservoirs that also act as anchors.
FIG. 4N shows a partial view of an embodiment of a substance delivery device comprising a substance reservoir made of foam.
Figure 4:
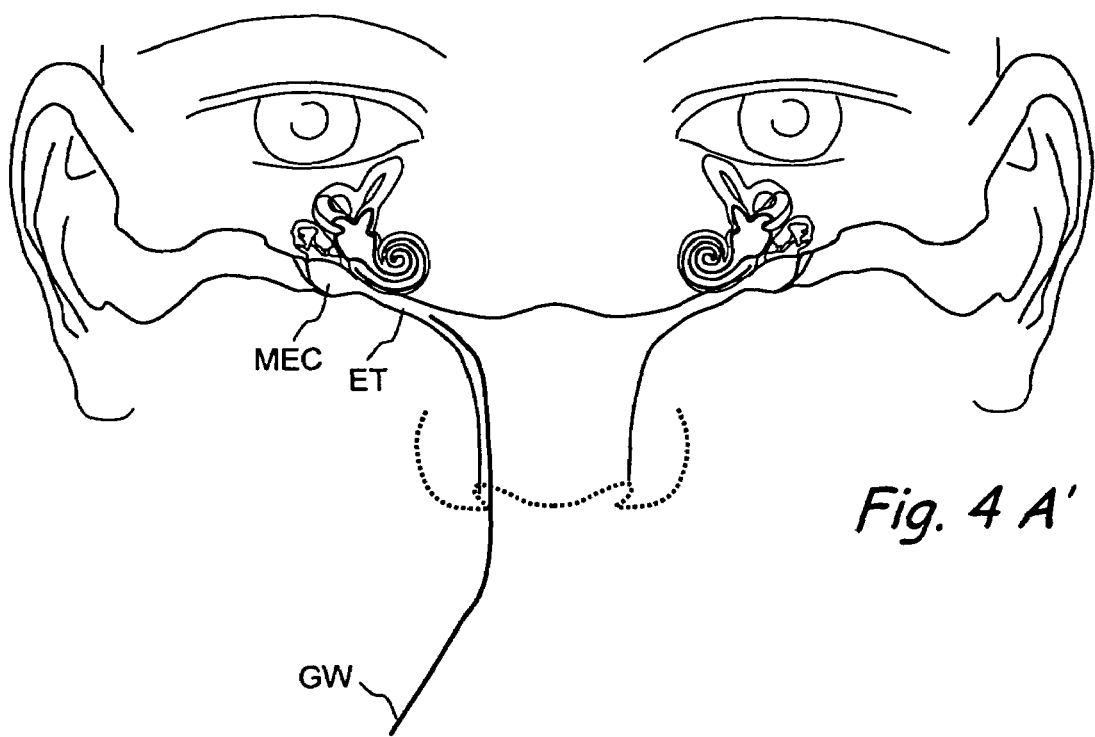
Figure 4B:
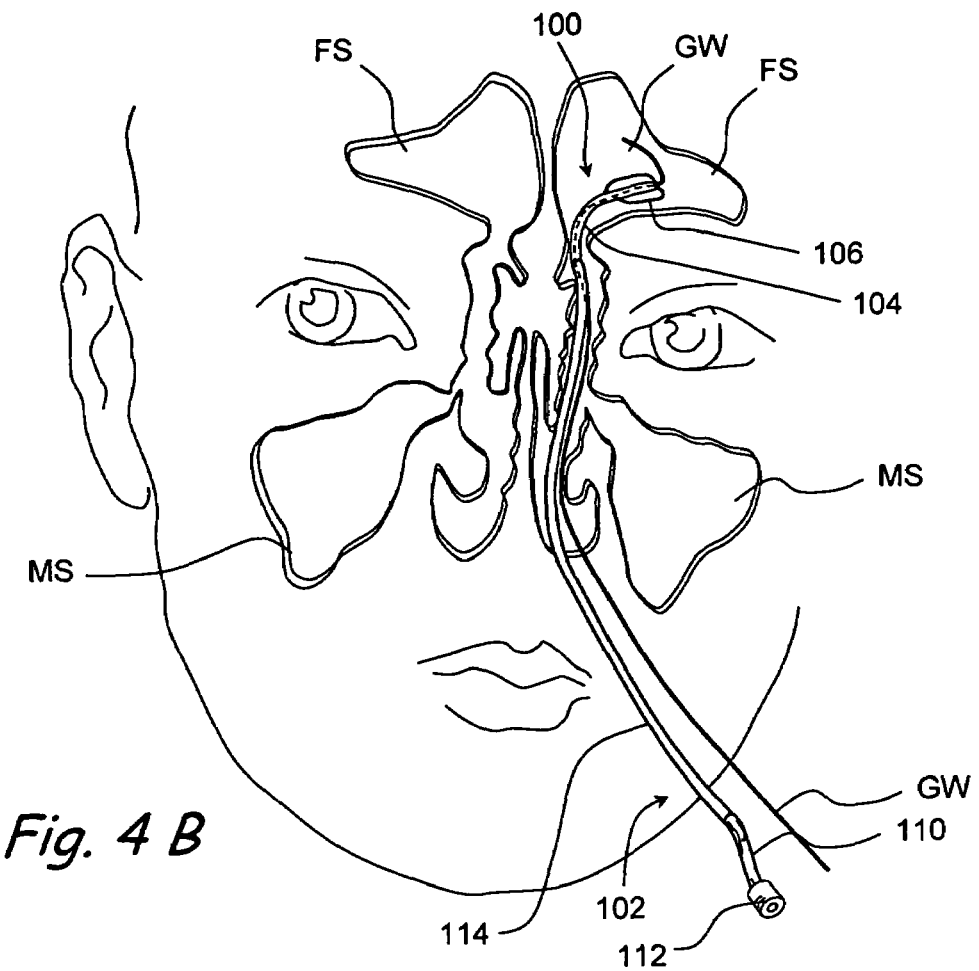
Figure 4B:
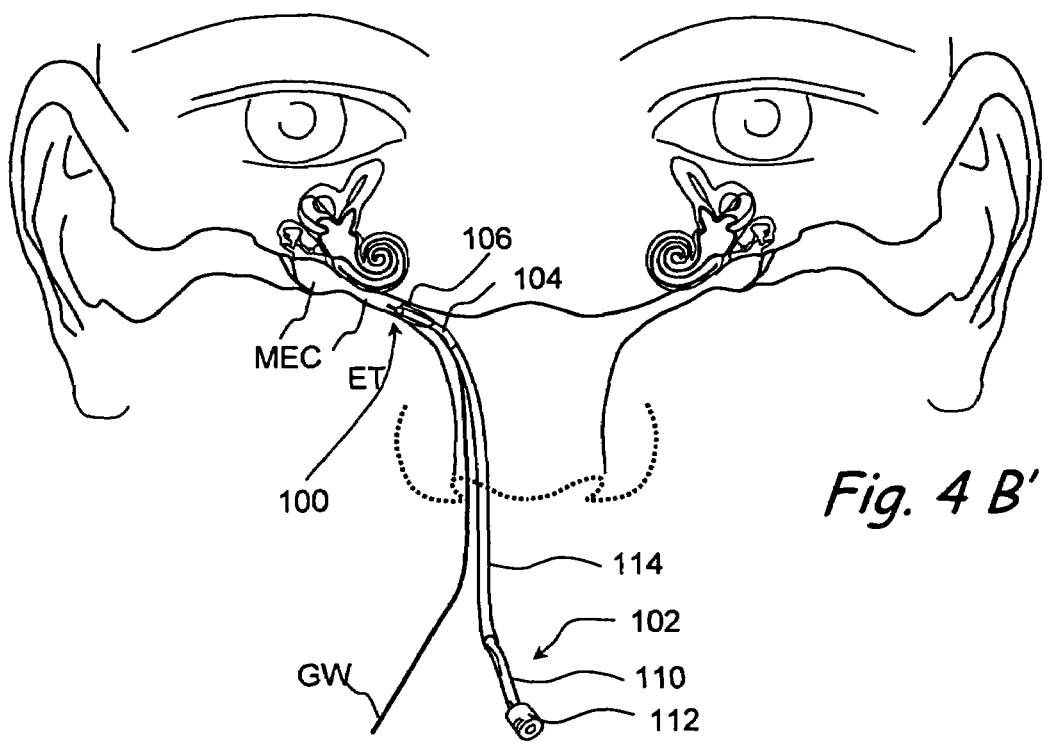
Figure 4C:
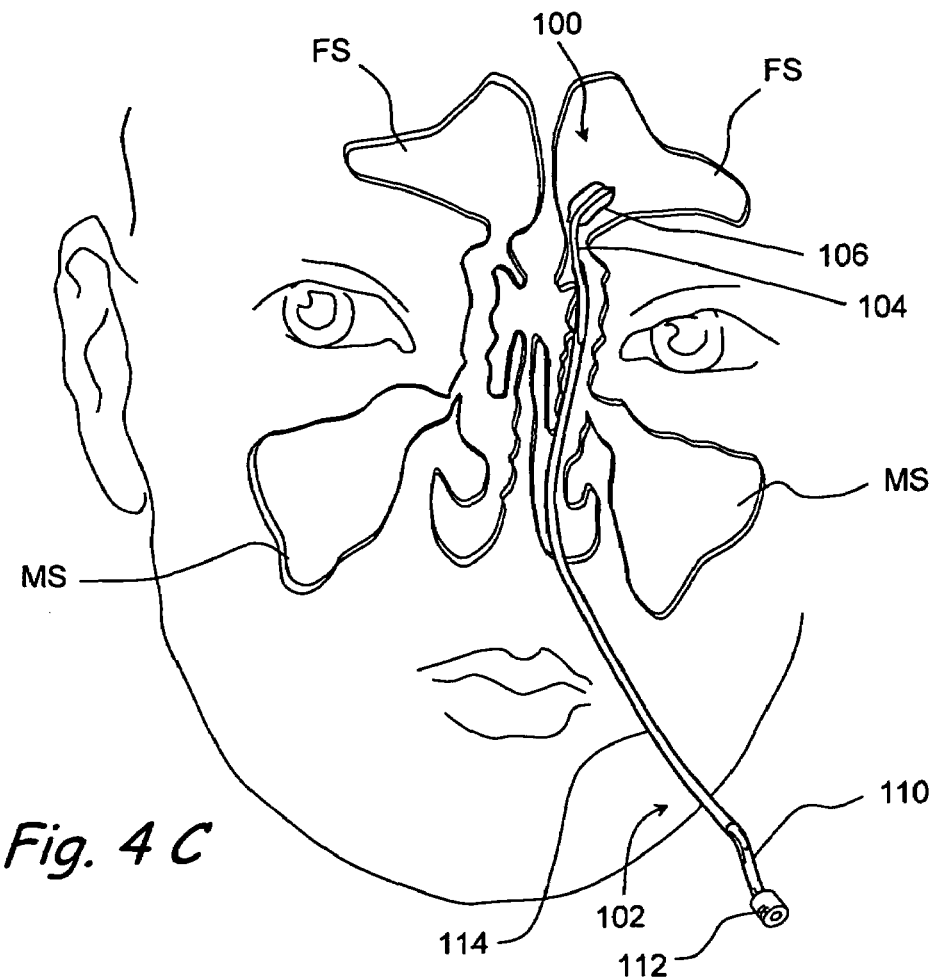
Figure 4C:
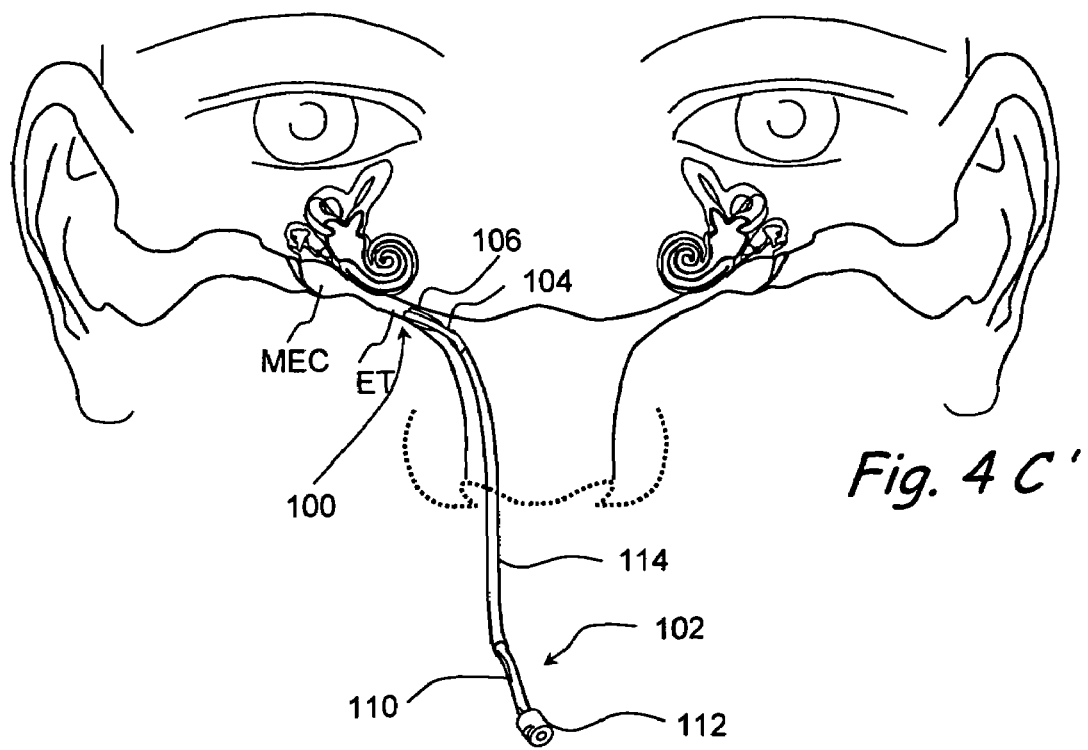
Figure 4D:
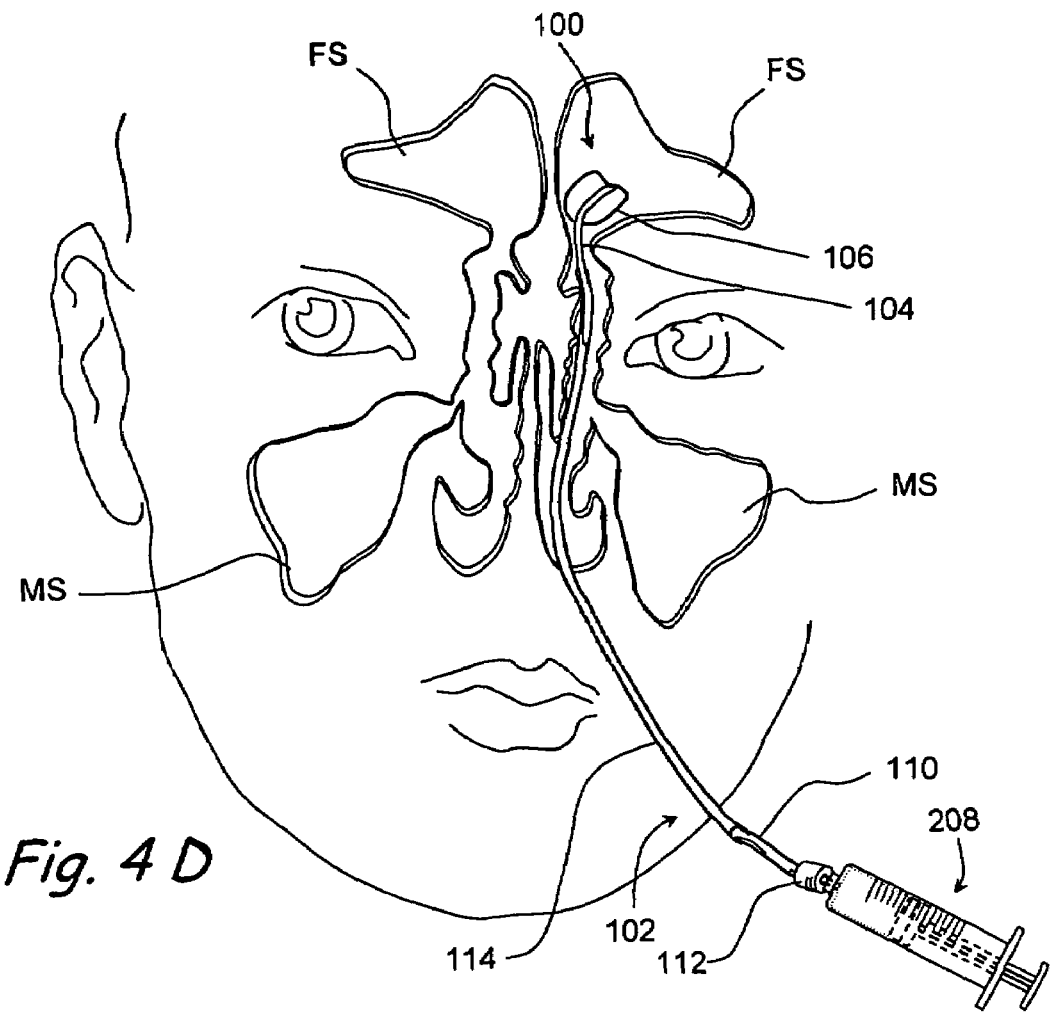
Figure 4D:
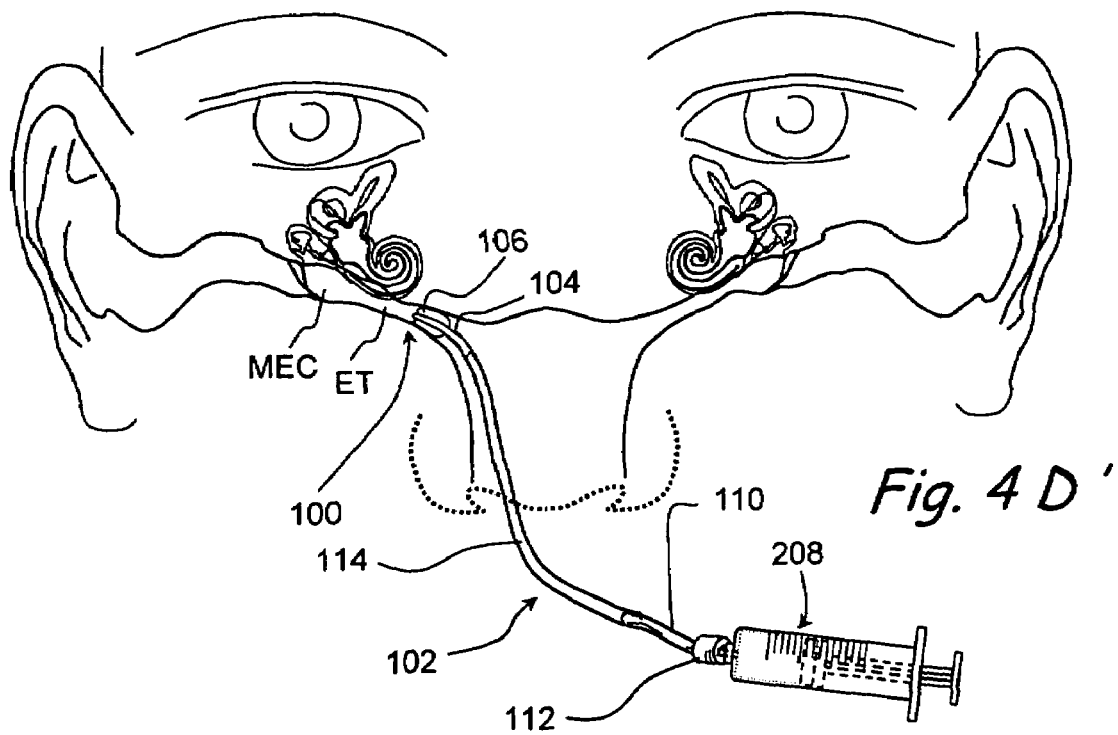
Figure 4:
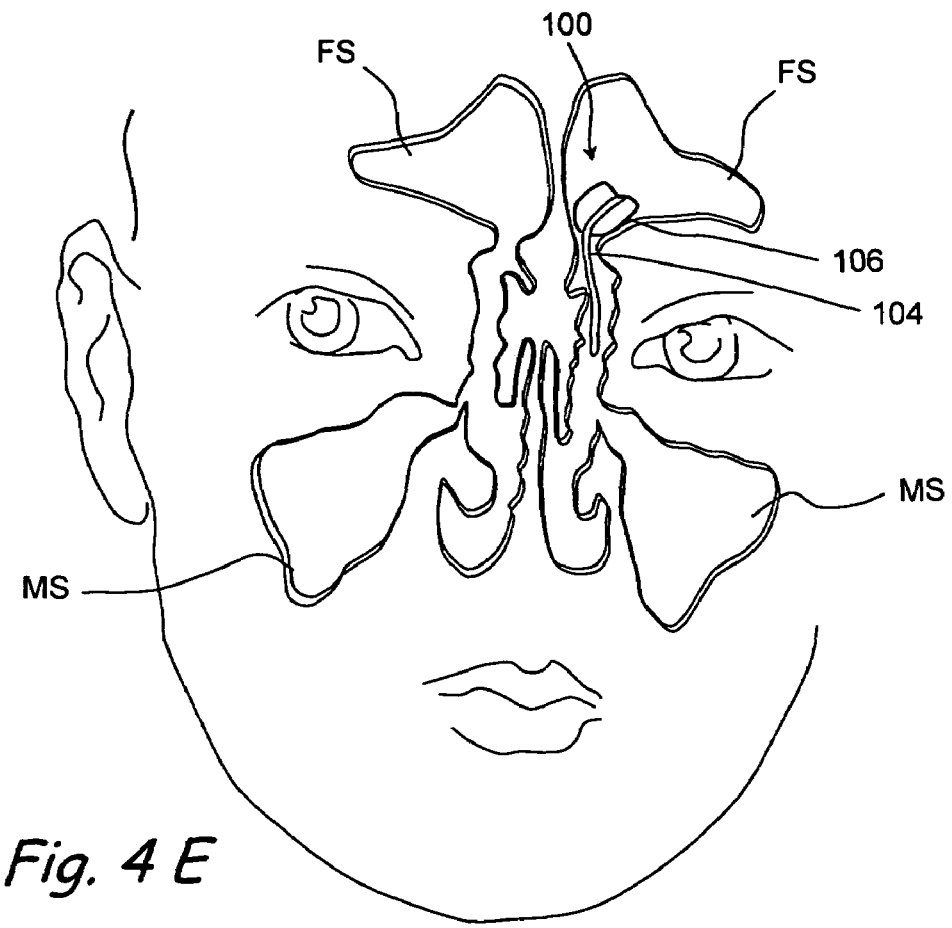
Figure 4:
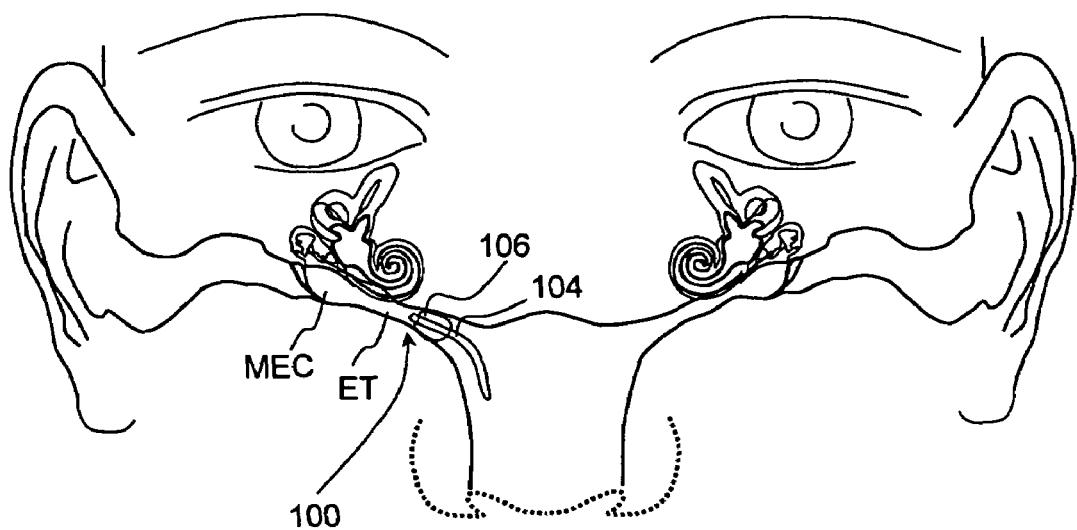
Figure 4:
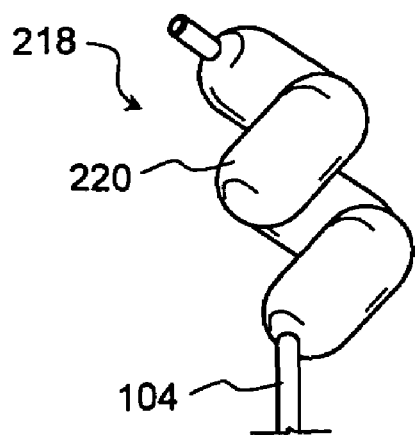
Figure 4:
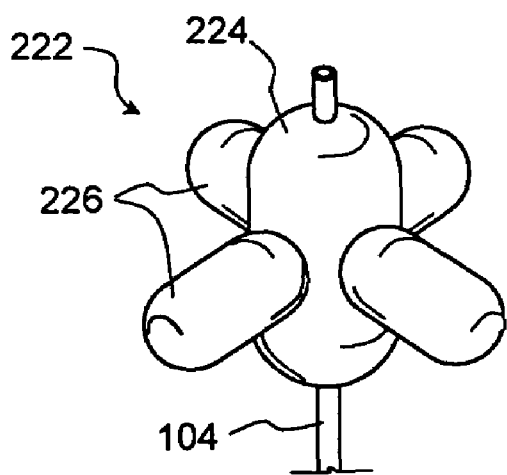
Figure 4:
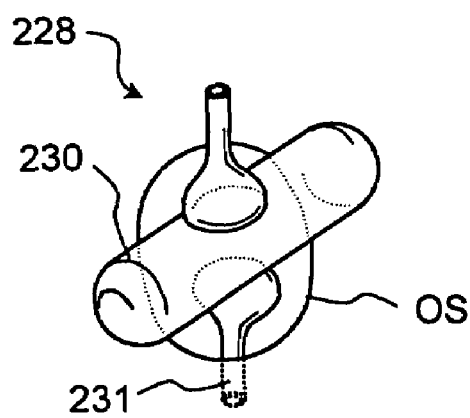
Figure 4:
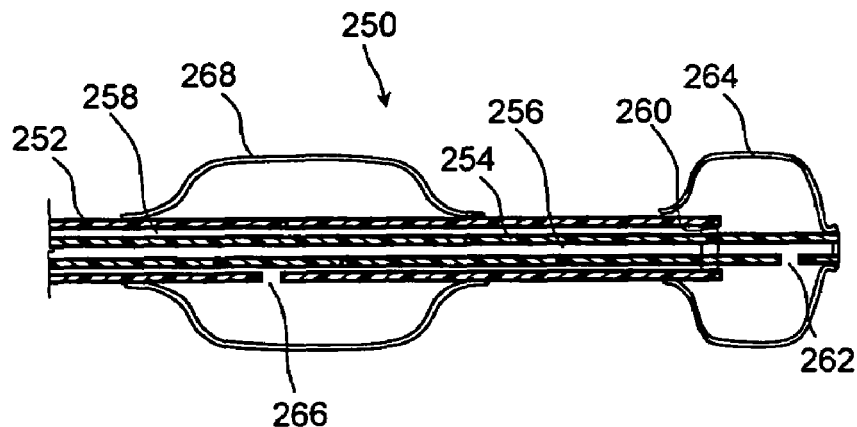
Figure 4:
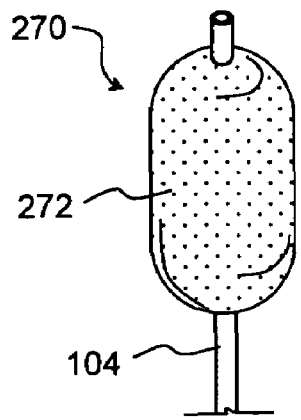

The various methods and devices disclosed herein may be used to delivery one or more substances to various regions in the head and neck as shown in FIGS. 4A-4E and 4A'-4E'. Examples of such regions include, but are not limited to paranasal sinuses, Eustachian tubes, middle ear regions, etc. FIGS. 4A through 4E show a coronal view of a human head showing the various steps of a method of delivering an implantable substance delivery device to one of the paranasal sinuses of a patient. In this example, a frontal sinus FS is used as an example of a paranasal sinus. Methods similar to those shown in FIGS. 4A through 4E may be used to deliver a substance delivery device in other paranasal sinuses or other spaces or cavities in the head. The substance delivery devices may be introduced along introducing devices such as guidewires, guide catheters, etc. For example, in FIG. 4A, a guidewire GW is introduced through a nostril of the patient. The distal end of the guidewire is navigated through the anatomy such that the distal end of the guidewire enters a paranasal sinus. This may be done by one or more methods disclosed in U.S. patent application Ser. Nos. 10/829,917; 10/912,578; 11/037,548 and i0/944,270, the entire disclosures of which are expressly incorporated herein by reference. Thereafter, in FIG. 4B, a substance delivery device 100 is introduced over the guidewire GW into the frontal sinus. In the embodiment shown in FIG. 4B, substance delivery device 100 comprises an elongate shaft 104 and a substance reservoir 106. In the example shown, substance delivery device 100 comprises a rapid exchange lumen which allows substance delivery device 100 to be introduced over guidewire GW. Alternatively substance delivery device 100 may comprise an end-to-end guidewire lumen. In FIG. 4B, the proximal end of substance delivery device 100 is connected to the distal end of a removable delivery catheter 102. In the embodiment shown, delivery and inflation device 114 comprises an elongate tube 114 comprising a lumen. The distal end of the lumen of elongate tube 114 is in fluid communication with the proximal end of a substance introducing lumen in elongate shaft 104. The proximal end of the lumen of elongate tube 114 is in fluid communication with a hub 112. A suitable syringe can be connected to hub 112 to inject a substance into reservoir 106 of substance delivery device 100. In the step shown in FIG. 4C, the guidewire GW is removed from the anatomy. In the step shown in FIG. 4D, reservoir 106 is filled with a substance through a syringe connected to hub 112. In the step shown in FIG. 4E, the proximal end of substance delivery device 100 is detached from the distal end of delivery catheter 102 thereby implanting substance delivery device 100 in the anatomy. Thereafter, delivery catheter 102 is removed from the anatomy. Substance delivery device 100 may be placed in the anatomy for a period ranging from 0.5 hours to 60 days after which it may be removed.

In another example, FIGS. 4A' through 4E' show a coronal view of a human head showing the various steps of an embodiment of a method of delivering an implantable substance delivery device to a Eustachian tube or middle ear of a patient. The method is performed by inserting a substance delivery device through the pharyngeal ostium of the Eustachian tube. Methods similar to those shown in FIGS. 4A' through 4E' may be used to deliver one or more substances to the Eustachian tubes or various regions of the middle or inner ear of patients. Examples of such inner ear regions include, but are not limited to cochlea, vestibule, etc. The substance delivery devices may be introduced along introducing devices such as guidewires, guide catheters, etc. For example, in FIG. 4A', a guidewire GW is introduced through a nostril of the patient. The distal end of the guidewire is navigated through the anatomy such that the distal end of the guidewire enters a Eustachian tube through the pharyngeal ostium of the Eustachian tube. This may be done by one or more methods disclosed in U.S. patent application Ser. Nos. 10/829,917; 10/912,578; 11/037,548 and 10/944,270, the entire disclosures of which are expressly incorporated herein by reference. In a particular embodiment, the guidewire GW is introduced through a guide catheter. Thereafter, in FIG. 4B', a substance delivery device 100 is introduced over the guidewire GW into the Eustachian tube. In the embodiment shown in FIG. 4B', substance delivery device 100 comprises an elongate shaft 104 and a reservoir 106. In the example shown, substance delivery device 100 comprises a rapid exchange lumen which allows substance delivery device 100 to be introduced over guidewire GW. Alternatively substance delivery device 100 may comprise an end-to-end guidewire lumen. In FIG. 4B', the proximal end of substance delivery device 100 is connected to the distal end of a removable delivery catheter 102. In the embodiment shown, delivery catheter 102 comprises an elongate tube 114 comprising a lumen. The distal end of the lumen of elongate tube 114 is in fluid communication with the proximal end of a substance introducing lumen in elongate shaft 104. The proximal end of the lumen of elongate tube 114 is in fluid communication with a hub 112. A suitable syringe can be connected to hub 112 to inject a substance into reservoir 106 of substance delivery device 100. In the step shown in FIG. 4C', the guidewire GW is removed from the anatomy. In the step shown in FIG. 4D', reservoir 106 is filled with a substance through a syringe connected to hub 112. In the step shown in FIG. 4E, the proximal end of substance delivery device 100 is detached from the distal end of delivery catheter 102 thereby implanting substance delivery device 100 in the anatomy. Thereafter, delivery catheter 102 is removed from the anatomy. Substance delivery device 100 may be placed in the anatomy for a period ranging from 0.5 hours to 60 days after which it may be removed.

Similar methods may be used to deliver a substance delivery device to a naso-lachrymal duct of a human or animal subject to deliver a substance to the naso-lachrymal duct.

The guidewires disclosed herein may comprise one or more anchors to temporarily anchor the guidewires to an anatomical region. Examples of such anchors include, but are not limited to anchoring balloons, notches on the guidewires, bent regions on the guidewires, self expanding elements, hooks, coiled elements, etc. The guidewires disclosed herein may comprise one or more sensors located on the distal region of the guidewires. The sensors enable the guidewires to be used in conjunction with suitable surgical navigation systems. In one embodiment, the sensor is an electromagnetic sensor used in conjunction with an electromagnetic surgical navigation system such as GE InstaTrak™ 3500 plus system etc. One or more sensors or other types of surgical navigation sensors or transmitters may also be located on other diagnostic or therapeutic devices disclosed herein.

The various substance reservoirs disclosed herein may be inflatable or non-inflatable. Inflatable substance reservoirs may be made of suitable balloons. The balloons may be made of various shapes including, but not limited to the balloon shapes disclosed herein and in the patent documents incorporated herein by reference. The balloons may be designed to also function as anchoring mechanisms to anchor the substance reservoir to the anatomy. Such anchoring is especially useful when the substance reservoirs are inserted into hollow regions such as paranasal sinuses. FIGS. 4F through 4L show various embodiments of substance reservoirs that can be used to design the various substance delivery devices disclosed herein. FIG. 4F shows a perspective view of an embodiment of an inflatable substance reservoir comprising an inflatable balloon comprising two or more lobes. FIG. 4F shows a region of a substance delivery device 210 comprising an inflatable balloon 212 comprising two or more lobes 214. Such a balloon shape comprising two or more lobes is useful to allow drainage of secretions when the balloon is placed in an anatomical region. For example, when inflatable balloon 212 is placed in a paranasal sinus through an ostium of the paranasal sinus, lobes 214 allows sinus secretions to flow between the lobes of the balloon and out of the ostium of the paranasal sinus. Inflatable balloon 212 may be made of suitable compliant, non-compliant or semi-compliant biocompatible materials. Examples of such materials include, but are not limited to polyurethane, silicone, Nylon, PET, polyethylene, PVC, etc. Inflatable balloon 212 is inflated by a substance introducing lumen in elongate shaft 104. FIG. 4G shows a cross section of inflatable balloon 212 shown in FIG. 4F through the plane 4G-4G. FIG. 4G shows inflatable balloon 212 comprising multiple lobes 214. In the example shown in FIGS. 4F and 4G, the substance reservoir comprised a balloon having 10 lobes. Similarly other substance reservoirs may be designed comprising a balloon having two or more lobes.

FIG. 4H shows a perspective view of an embodiment of an inflatable substance reservoir comprising a spiral inflatable balloon. FIG. 4F shows a region of a substance delivery device 218 comprising a spiral inflatable balloon 220. Such a spiral balloon is useful to allow drainage of secretions when the balloon is placed in an anatomical region. For example, when the balloon is placed in a paranasal sinus through an ostium of the paranasal sinus, a spiral balloon allows sinus secretions to flow between adjacent turns of the spiral balloon and out of the ostium of the paranasal sinus. Inflatable balloon 220 may be made of suitable compliant, non-compliant or semi-compliant biocompatible materials. Examples of such materials include, but are not limited to polyurethane, silicone, Nylon, PET, polyethylene, PVC, etc. Inflatable balloon 220 is inflated by an elongate shaft 104.

The inflatable substance reservoirs disclosed herein may comprise one or more radial protrusions. For example, FIG. 4I shows a perspective view of a region of a substance delivery device comprising an inflatable balloon having one or more radial protrusions. Substance delivery device 222 comprises an inflatable balloon 224. The inflatable balloon 224 comprises one or more radial protrusions 226. Radial protrusions 226 are oriented radially to the axis of inflatable balloon 224. Radial protrusions 226 may be inflatable or non-inflatable. This increases the profile of inflatable balloon 224 when inflatable balloon 224 is inflated. Such a balloon comprising one or more radial protrusions is useful to allow drainage of secretions when the balloon is placed in an anatomical region. For example, when balloon 224 is placed in a paranasal sinus through an ostium of the paranasal sinus, balloon 224 allows sinus secretions to flow between adjacent protrusions 226 and out of the ostium of the paranasal sinus. Protrusions 226 also help to anchor balloon 224 to the surrounding anatomy. Inflatable balloon 224 may be made of suitable compliant, non-compliant or semi-compliant biocompatible materials. Examples of such materials include, but are not limited to polyurethane, silicone, Nylon, PET, polyethylene, PVC, etc. Inflatable balloon 224 is inflated by a substance introducing lumen in elongate shaft 104.

The inflatable substance reservoirs disclosed herein may comprise a balloon oriented transversely to the axis of an inflating shaft. For example, FIG. 4J shows a perspective view of a region of a substance delivery device comprising an inflatable balloon oriented transversely to the axis of the substance delivery device. In FIG. 4J, a substance delivery device 228 is inserted through a paranasal sinus ostium into a paranasal sinus. Substance delivery device 228 comprises an elongate inflatable balloon 230. The axis of inflatable balloon is substantially perpendicular to the axis of substance delivery device 228. This increases the profile of inflatable balloon 230 when inflatable balloon 230 is inflated. This helps to anchor balloon 242 to the surrounding anatomy while still allowing secretions to flow around balloon 230. Inflatable balloon 230 may be made of suitable compliant, non-compliant or semi-compliant biocompatible materials. Examples of such materials include, but are not limited to polyurethane, silicone, Nylon, PET, polyethylene, PVC, etc. Inflatable balloon 230 is inflated by a substance introducing lumen in elongate shaft 231.

The inflatable substance reservoirs disclosed herein may comprise a balloon having one or more vents to prevent vacuum formation inside a substance reservoir. For example, FIG. 4K shows a side view of a region of an inflatable substance reservoir comprising a balloon with one or more pores and a vent. FIG. 4K shows a substance delivery device 232 comprising an inflatable balloon 234 that acts as a substance reservoir. Inflatable balloon 234 may be made of suitable non-compliant or semi-compliant biocompatible materials. Examples of such materials include, but are not limited to polyurethane, Nylon, PET, polyethylene, PVC, etc. Inflatable balloon 234 is inflated by an elongate shaft 104 comprising a reservoir filling lumen. The lumen of elongate shaft 104 is in fluid communication with inflatable balloon 234. Inflatable balloon 234 comprises one or more pores 236. The substance stored in inflatable balloon 234 is delivered through pores 236 into the surrounding anatomy. Thus, the volume of the substance stored in inflatable balloon 234 gradually reduces. This process gradually creates a vacuum inside inflatable balloon 234. The vacuum prevents or reduces the delivery of the substance stored in inflatable balloon 234 through pores 236. In order to prevent or reduce the formation of the vacuum, substance delivery device 232 further comprises a vent 238. Vent 238 allows air to enter inflatable balloon 234. This air replaces the amount of substance lost through pores 236 and thus prevents the formation of a vacuum in inflatable balloon 234. This in turn maintains the rate of delivery of the substance stored in inflatable balloon 234 through pores 236.

The distal end of one or more substance delivery devices disclosed herein may be designed to prevent or reduce trauma to the surrounding anatomy. In the embodiments of substance delivery devices comprising an inflatable substance reservoir, a portion of the inflatable reservoir may be designed to generate an atraumatic distal region. For example, FIG. 4L shows a section through a substance delivery device comprising an inflatable substance delivery reservoir shaped to produce an atraumatic distal end. In FIG. 4L, substance delivery device 240 comprises an inflatable balloon 242 that acts as a substance reservoir. Inflatable balloon 242 may be made of suitable compliant, non-compliant or semi-compliant biocompatible materials. Examples of such materials include, but are not limited to polyurethane, silicone, Nylon, PET, polyethylene, PVC, etc. Inflatable balloon 242 is inflated through an elongate shaft 104 comprising a reservoir filling lumen. The lumen of elongate shaft 104 is in fluid communication with balloon 242 through a shaft opening 244. A distal region of elongate shaft 104 is plugged or blocked by a plug 246. Inflatable balloon 242 may further comprise one or more pores 248 that are in fluid communication with the exterior of inflatable balloon 242. Substance delivery device 240 may deliver a substance to the surrounding anatomy through pores 248. Inflatable balloon 242 is connected to elongate shaft 104 at a proximal region and at a distal region of inflatable balloon 242. The distal region of inflatable balloon 242 is everted and connected to elongate shaft 104 as shown in FIG. 4L. Thus, when inflatable balloon 242 is inflated, a distal region of inflatable balloon 104 protrudes distal to the distal end of elongate shaft 104 as shown in FIG. 4L. This creates an atraumatic distal end of substance delivery device 240.

The one or more pores on the inflatable substance reservoirs such as the inflatable substance reservoirs disclosed in FIGS. 4K and 4L may be created by laser drilling the surface of the materials of the inflatable substance reservoirs. In one example of a method of creating the one or more pores, an Excimer laser is used to create pores. The Excimer laser may be used to create pores of a pore size ranging from about 20 microns to about 200 microns. Inflatable balloon 234 and inflatable balloon 242 of FIGS. 4K and 4L respectively may have a balloon diameter ranging from around 7-10 mm and balloon length ranging from around 10-20 mm. The balloon wall thickness may range from around 0.001-0.003 inches. The number and pore size of the one or more pores and the balloon wall thickness may be designed to avoid jetting of the substance stored in the inflatable substance reservoirs through the one or more pores.

One or more substance delivery devices disclosed herein may comprise more than one substance reservoirs that are inflated through one or more reservoir filling lumens. Also, one or more substance reservoirs disclosed herein may act as anchors to prevent or reduce relative motion between the substance delivery devices and regions of the anatomy. For example, FIG. 4M shows a cross section through a substance delivery device comprising two substance reservoirs that also act as anchors. Substance delivery device 250 of FIG. 4M comprises an outer tube 252 and an inner tube 254 enclosed by outer tube 252. Outer tube 252 and inner tube 254 may be made of suitable biocompatible materials including, but not limited to Pebax, PEEK, Nylon, polyethylene, polyurethane, polyethylene terephthalate, etc. Inner tube 254 encloses an inner lumen 256. The annular region between the outer surface of inner tube 254 and the inner surface of outer tube 252 forms an outer lumen 258. The distal end of outer lumen 258 is plugged by an annular plug 260. Inner tube 254 comprises a first opening or pore 262 located distal to the distal end of outer tube 252. First opening or pore 262 creates a fluid communication between inner lumen 256 and a distal balloon 264. Thus, inner lumen 256 may be used to inflate distal balloon 264 with a suitable fluid substance. A distal region of distal balloon 264 is attached to the outer surface of inner tube 254 and a proximal region of distal balloon 264 is attached to the outer surface of outer tube 252 as shown. A region of outer tube 252 proximal to annular plug 260 comprises a second opening or pore 266. Second opening or pore 266 creates a fluid communication between outer lumen 258 and a proximal balloon 268. Thus, outer lumen 258 may be used to inflate proximal balloon 268 with a suitable fluid substance. Outer lumen 258 and inner lumen 256 may be provided with valves, plugging mechanisms, etc. disclosed elsewhere in this patent application to prevent the leakage of the fluid substance from the proximal ends of outer lumen 258 and inner lumen 256. In one method embodiment, substance delivery device 250 is introduced through an anatomical opening such as a paranasal sinus ostium. Substance delivery device 250 is positioned such that distal balloon 264 lies distal to the anatomical opening and proximal balloon 268 lies proximal to the anatomical opening. Thereafter, both distal balloon 264 and proximal balloon 268 are inflated. Both distal balloon 264 and proximal balloon 268 acts as anchors and prevent or reduce the motion of substance delivery device 250 relative to the anatomical opening. In the embodiment shown in FIG. 4M, distal balloon 262 and proximal balloon 268 are inflated by two separate lumens. In an alternate embodiment, distal balloon 262 and proximal balloon 268 are inflated by a single lumen.

Although the substance reservoirs disclosed herein are mostly illustrated as inflatable balloons, the substance delivery devices disclosed herein may comprise several other embodiments of substance reservoirs. For example, the substance reservoirs disclosed herein may comprise an absorbent element. Examples of such absorbent elements include, but are not limited to foams, fibrous elements, etc. FIG. 4N shows a partial view of an embodiment of a substance delivery device comprising a substance reservoir made of foam. Substance delivery device 270 of FIG. 4N comprises an elongate shaft 104. Elongate shaft 104 comprises a reservoir filling lumen. The filling lumen is in fluid communication with a substance reservoir 272 located on the distal region of elongate shaft 104. The filling lumen may be used to introduce a suitable substance into substance reservoir 272 before or after insertion of substance delivery device 270 into the anatomy. Substance reservoir 272 may be made from suitable biocompatible foam materials including, but not limited to polyvinyl acetate, polyurethane, polylactides, carboxymethylated cellulose, polyethylene, silicone, biodegradable materials such as gelatin, fibers such as cotton, etc. Substance reservoir 272 may be connected to a controlled delivery element. The controlled delivery element may be used to deliver the substance in substance reservoir 272 to the surrounding anatomy at a controlled rate over a desired period of time. In one embodiment, the controlled delivery element comprises a membrane located on the outer surface of substance reservoir 272. The membrane regulates the delivery of the substance from substance reservoir 272 to the surrounding anatomy. Substance reservoir 272 may be enclosed in a series of struts that contain substance reservoir 272. In one embodiment, the struts are substantially parallel to elongate shaft 104.

One or more of the drug delivery devices disclosed herein may comprise a controlled substance release mechanism to controllably release a substance from a substance reservoir into the surrounding anatomy over a period of time. In one embodiment, the controlled substance release mechanism comprises a pressuring mechanism that exerts a pressure on the substance reservoir to squeeze the substance out of the substance reservoir into the surrounding anatomy. The pressuring mechanism may be designed to exert a fairly constant pressure over the treatment duration.

One example of a pressuring mechanism is shown in FIG. 5A. FIG. 5A shows a sectional view of an embodiment of a substance delivery device comprising a pressure exerting mechanism. The design of substance delivery device 276 of FIG. 5A is similar to the design of substance delivery substance 240 of FIGS. 2G and 2H. Drug delivery device 276 comprises an elongate shaft 278. Elongate shaft 278 may be made of suitable biocompatible materials including, but not limited to Pebax, PEEK, Nylon, polyethylene, etc. Elongate shaft 278 encloses a substance introducing lumen 280. A distal region of lumen 280 is blocked by a plug 232. A substance reservoir 282 is located on a distal region of elongate shaft 278. In the example shown in FIG. 5A, substance delivery reservoir 282 comprises an inflatable balloon. The inflatable balloon is preferably made from suitable non-compliant, compliant or semi-compliant materials including, but not limited to polyurethane, silicone, Nylon, PET, polyethylene, PVC, C-flex™, etc. The material of the inflatable balloon is substantially impermeable to water. Lumen 280 is in fluid communication with substance reservoir 282 through one or more first openings or pores 284. Lumen 280 may thus be used to fill substance reservoir 282 with a suitable substance. A valve 286 is located near first openings or pores 284. Valve 286 allows the substance to flow from lumen 280 to substance reservoir 282. Also, valve 286 prevents or substantially reduces the flow of the substance from substance reservoir 282 to lumen 280. The design of valve 286 in FIG. 5A is similar to the design of valve 252 in FIGS. 2G and 2H. The substance stored in substance reservoir 282 is released into the surrounding anatomy through one or more second openings or pores 288 that create a fluid communication between substance reservoir 282 and lumen 280. In the example shown in FIG. 5A, one or more second openings or pores 288 are present on the region of elongate shaft 278 enclosed by substance reservoir 282. In this example, the distal end of lumen 280 opens into the surrounding anatomy such that the substance flows from substance reservoir 282 to the surrounding anatomy. Substance delivery device 276 further comprises a pressure exerting mechanism comprising a water permeable membrane 290 and a water-swellable material 292 enclosed within water permeable membrane 290. Water-swellable material 292 is sandwiched between water permeable membrane 290 and the outer surface of substance delivery reservoir 282 as shown in FIG. 5A. After substance delivery device 276 is implanted in a target anatomical region such as a paranasal sinus, water molecules from the surrounding fluids e.g. sinus mucous gradually permeate through water permeable membrane 290. These water molecules then come into contact with water-swellable material 292. This in turn causes water-swellable material 292 to gradually swell over a period of time. FIG. 5A' shows a sectional view of the embodiment of the substance delivery device shown in FIG. 5A showing the pressure exerting mechanism exerting a pressure on a substance reservoir. Swelling of water-swellable material 292 exerts a gradually increasing pressure on substance delivery reservoir 282 as shown in FIG. 5A'. This gradually squeezes substance reservoir 282 and causes the substance stored in substance reservoir 282 to be gradually released through one or more second openings or pores 288 into the surrounding anatomy. Water permeable membrane 290 may be made of suitable materials that allow water molecules to pass through but filter out dissolved or un-dissolved solids including the substance stored in substance reservoir 282 as shown in FIG. 5A'. Examples of such membranes include, but not limited to reverse osmosis membranes, nanofiltration membranes, etc. Water permeable membrane 290 may be made of a wide variety of natural and synthetic polymers, including, but not limited to polydimethylsiloxanes (silicone rubbers), ethylene-vinylacetate copolymers, polyurethanes, polyurethane-polyether copolymers, polyethylenes, polyamides, polyvinylchlorides (PVC), polypropylenes, polycarbonates, polytetrafluoroethylenes (PTFE), polyacrylonitriles, polysulfones, cellulosic materials (e.g., cellulose monoacetate, cellulose diacetate, cellulose triacetate, cellulose nitrate, etc.), hydrogels (e.g., 2-hydroxymethylmethacrylate), etc. In one embodiment, water-swellable material 292 is made of suitable super-absorbent polymers including, but not limited to sodium salts of crosslinked polyacrylic acid, potassium salts of crosslinked polyacrylic acid/polyacrylamide copolymer, synthetic polyacrylamide with a potassium salt base, graft copolymers of cross-linked polyacrylic acid and starch, SNAPs (Safe and Natural Absorbent Polymers), etc.

Figure 5:
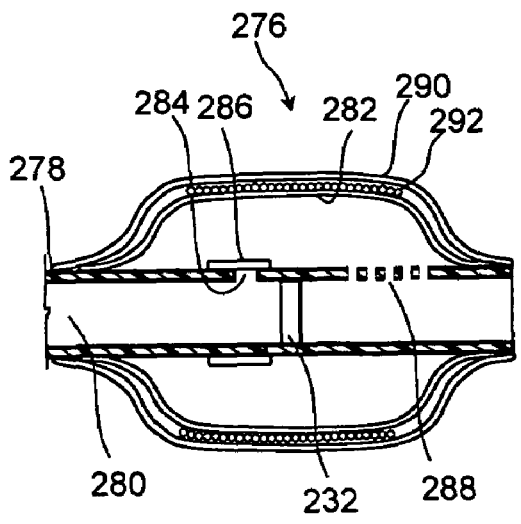
FIG. 5A shows a sectional view of an embodiment of a drug delivery device comprising a pressure exerting mechanism.
FIG. 5B shows a cross sectional view of an embodiment of a substance delivery device comprising a controlled substance release element in the form of a wick.
FIG. 5C shows the side view of an embodiment of an elongate porous tube that may be used to control the rate of delivery of a substance to the anatomy from a substance delivery device.
FIG. 5D shows a cross sectional view of an embodiment of a substance delivery device comprising the porous tube of FIG. 5C.
FIG. 5E shows a cross sectional view of an embodiment of a substance delivery device comprising a porous shaft region for controlled delivery of a substance to the anatomy.
FIG. 5F shows a cross section of the substance delivery device of FIG. 5E through the plane 5F-5F.
Figure 5:
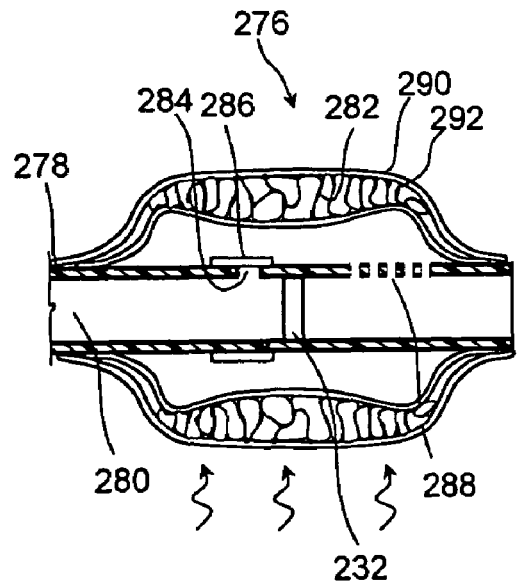
Figure 5B:
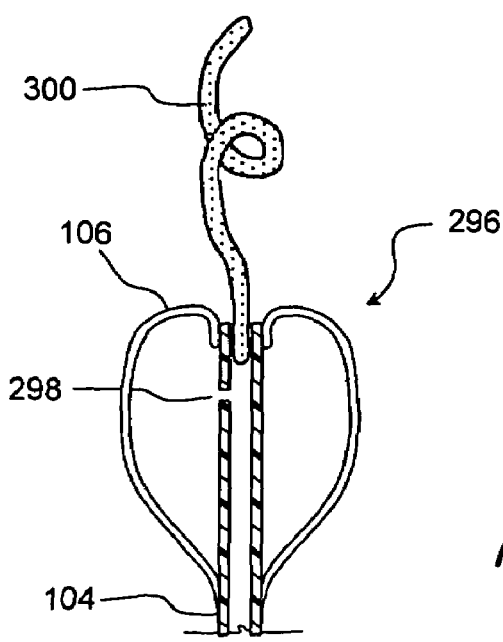

FIG. 5B shows a cross sectional view of an embodiment of a substance delivery device comprising a controlled substance release element in the form of a wick. The basic design of substance delivery device 296 of FIG. 5B is similar to the design of substance delivery device 240 of FIG. 4L. Substance delivery device 296 comprises a substance reservoir. In the embodiment shown in FIG. 5B, the substance reservoir is an inflatable balloon 106. Inflatable balloon 106 may be made of suitable compliant or semi-compliant biocompatible materials. Examples of such materials include, but are not limited to polyurethane, silicone, Nylon, PET, polyethylene, PVC, etc. Inflatable balloon 106 is inflated through an elongate shaft 104 comprising a reservoir filling lumen. Inflatable balloon 106 is connected to elongate shaft 104 at a proximal region and at a distal region of inflatable balloon 106. The distal region of inflatable balloon 106 is everted and connected to elongate shaft 104 as shown in FIG. 5B. Thus, when inflatable balloon 106 is inflated, a distal region of inflatable balloon 106 protrudes distal to the distal end of elongate shaft 104 as shown in FIG. 5B. This creates an atraumatic distal end of substance delivery device 296. The lumen of elongate shaft 104 is in fluid communication with inflatable balloon 106 through a shaft opening 298. The lumen of elongate shaft 104 further comprises a plugging mechanism e.g. a one way valve. The plugging mechanism is located proximal to shaft opening 298. The plugging mechanism prevents the backflow of fluid along the proximal direction after a user fills inflatable balloon 106 with a suitable fluid substance through the lumen of elongate shaft 104. Substance delivery device 296 further comprises a controlled delivery mechanism for controlled delivery of a substance from substance delivery device 296. In the embodiment shown in FIG. 5B, the controlled delivery mechanism is an elongate wick 300 attached to the distal end of elongate shaft 104. Wick 300 is in fluid communication with the lumen of elongate shaft 104. Wick 300 comprises a plurality of pores or channels such that a fluid in contact with the proximal region of wick 300 is transported in the distal direction along wick 300 by capillary action. Wick 300 may be made of suitable biocompatible polymers including, but not limited to cellulose, collagen, polyvinyl acetate, etc. Wick 300 may comprise a variety of two-dimensional or three dimensional shapes. For example, wick 300 may comprise one or more turns, coils, bends, curves or angled regions, etc. to increase the area of contact surface between wick 300 and a region of the anatomy. Wick 300 regulates the delivery of the substance from the substance reservoir to the surrounding anatomy and thus allows for extended delivery of the substance to the surrounding anatomy. In one embodiment of a method of using substance delivery device 296, a user introduces substance delivery device 296 into a target anatomical region such that one or more regions of wick 300 are in contact with the anatomical region. Thereafter, the user introduces a suitable substance in inflatable balloon 106. Thereafter, the substance in inflatable balloon 106 comes into contact with the proximal region of wick 300. The substance is then transported along wick 300 by capillary action. The substance is then delivered to the anatomical region at a controlled rate through wick 300.

In an alternate embodiment, the controlled delivery mechanism is a thin elongate delivery tube comprising a delivery lumen. The proximal end of the delivery lumen is in fluid communication with the substance stored in substance delivery device 296. The substance is delivered to the surrounding anatomy from the distal tip of the delivery lumen. The delivery tube may comprise one or more turns, coils, bends, curves or angled regions, etc. The delivery tube regulates the delivery of the substance from the substance reservoir to the surrounding anatomy and thus allows for extended delivery of the substance to the surrounding anatomy.

Figure 5C:
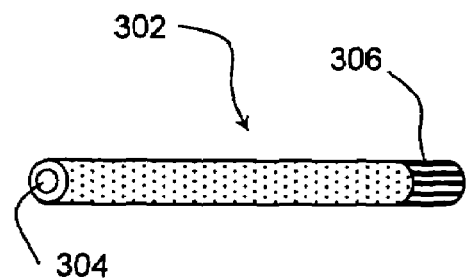

One or more embodiments of substance delivery devices disclosed herein may comprise various embodiments of porous elements for controlling the rate of delivery of a substance to the anatomy. Such porous elements may comprise one or more pores. The pore size of such pores may range from 0.2 microns to 200 microns. For example, FIG. 5C shows the side view of an embodiment of an elongate porous tube 302 that may be used to control the rate of delivery of a substance to the anatomy from a substance delivery device. Porous tube 302 comprises an elongate tube comprising a lumen. The elongate tube may be made of suitable biocompatible materials including, but not limited to silicone, Pebax, PEEK, Nylon, polyethylene, polyurethane, etc. The elongate tube comprises one or more pores that create a fluid communication between the exterior of porous tube 302 and the lumen of porous tube 302. The one or more pores may have a pore size ranging from 0.2 microns to 200 microns. The proximal end of porous tube 302 is plugged by a plug 304. An atraumatic tip 306 may be attached to the distal end of porous tube 302 to prevent or reduce damage to the anatomy by the distal end of porous tube 302.

Figure 5D:
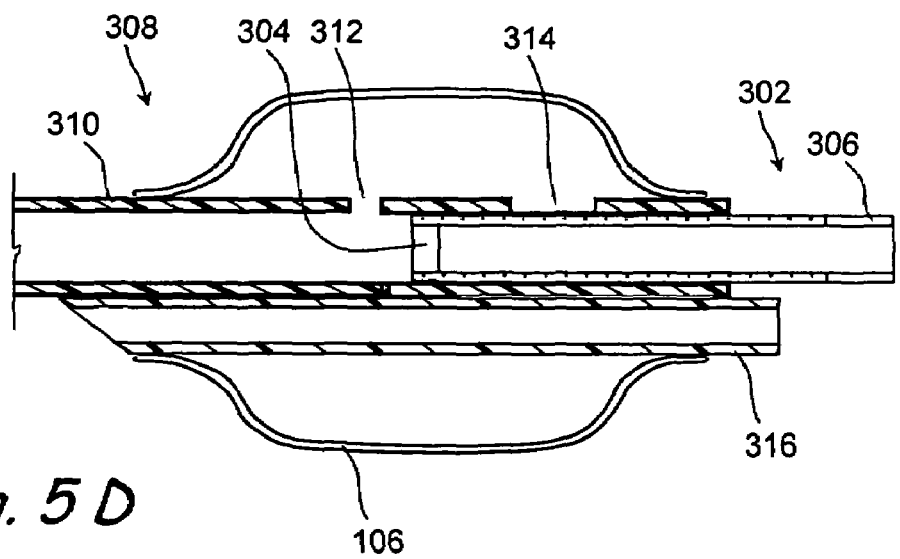
Figure 5:
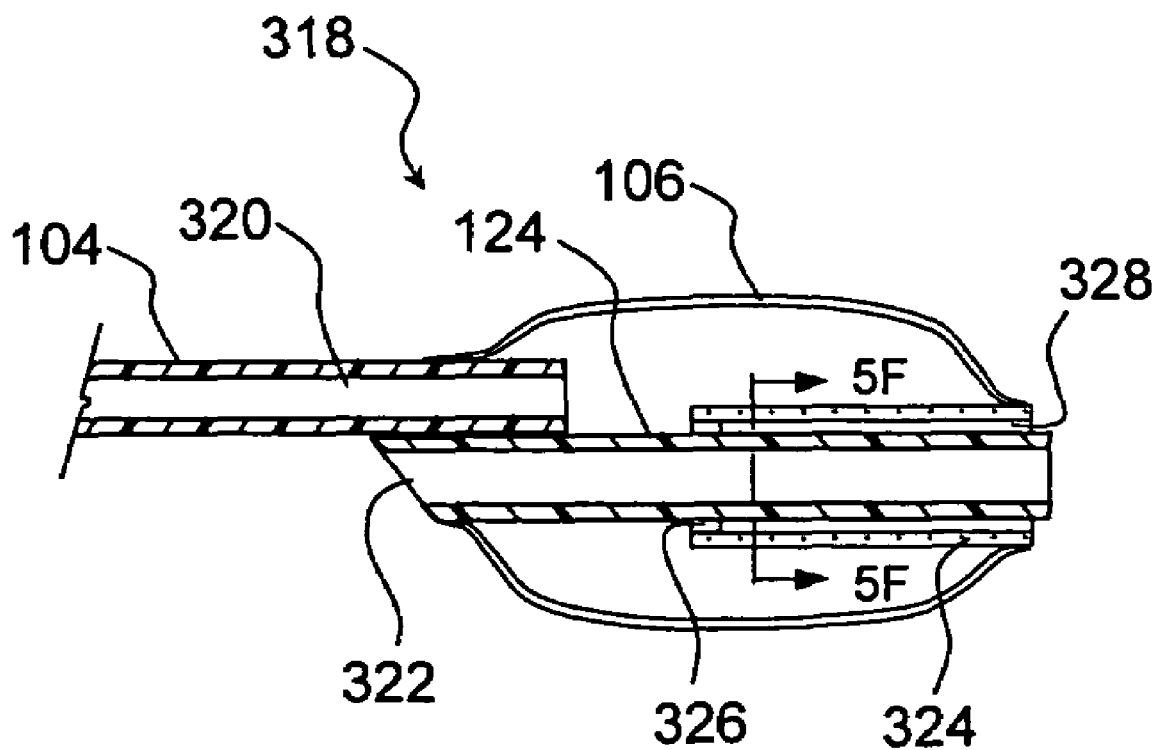
Figure 5:
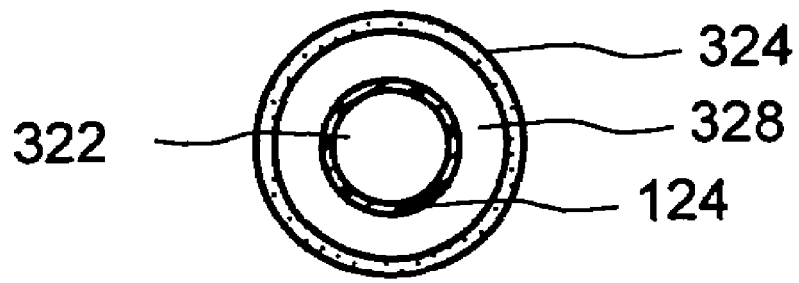
Figure 6:
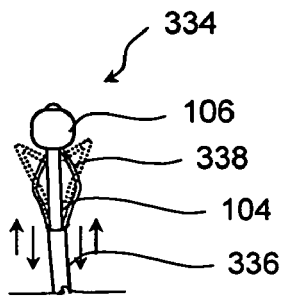
FIG. 6A shows an embodiment of a substance delivery device comprising an anchoring or retention element comprising deployable arms.
FIG. 6B shows a perspective view of an embodiment of a substance delivery device comprising a bent or angled shaft.
FIG. 6C shows a perspective view of an embodiment of a substance delivery device comprising a shaft comprising a curved or coiled region.
FIG. 6D shows a perspective view of an embodiment of a substance delivery device comprising an elongate shaft comprising flexible, projections.
FIG. 6E shows a perspective view of an embodiment of a substance delivery device comprising a substance reservoir having one or more radial projections.
FIGS. 6F-6H show embodiment of substance delivery devices comprising suturing arrangement to suture the substance delivery devices to anatomical structures.
Figure 6:
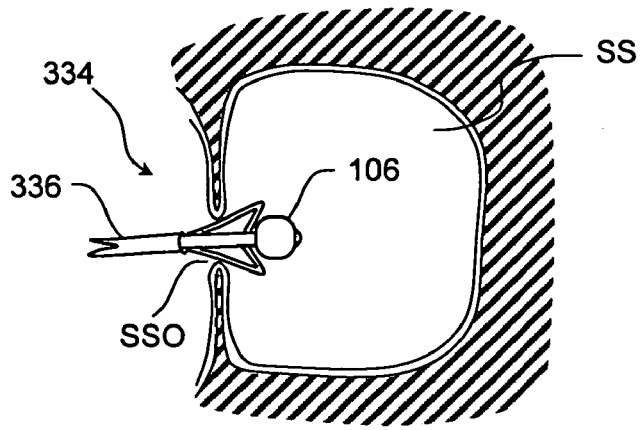
Figure 6:
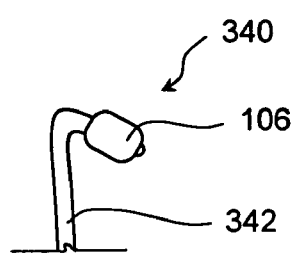
Figure 6:
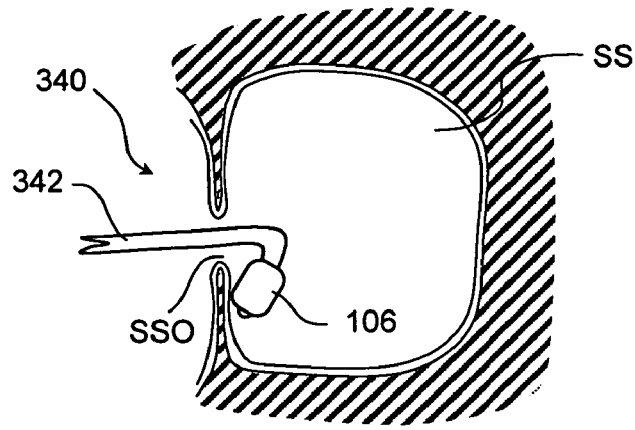
Figure 6:
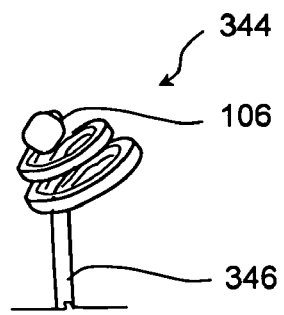
Figure 6:
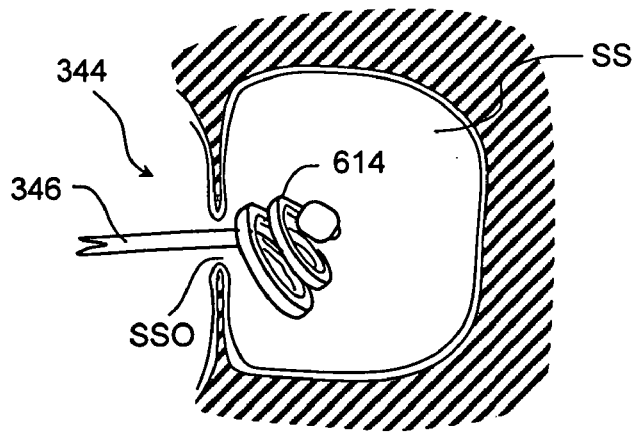
Figure 6:
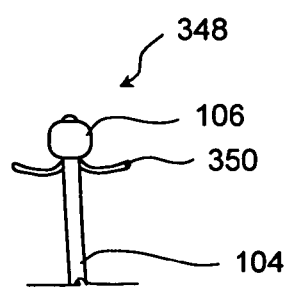
Figure 6:
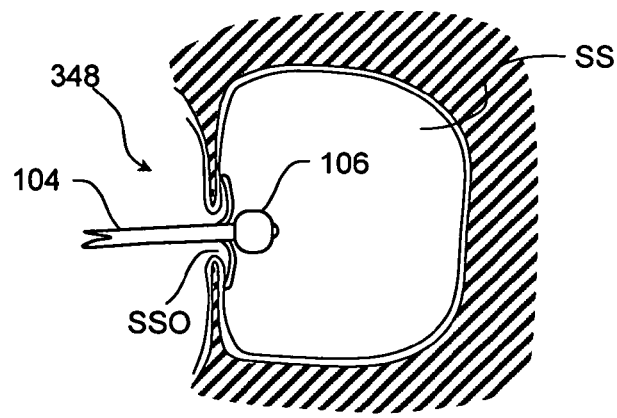
Figure 6:
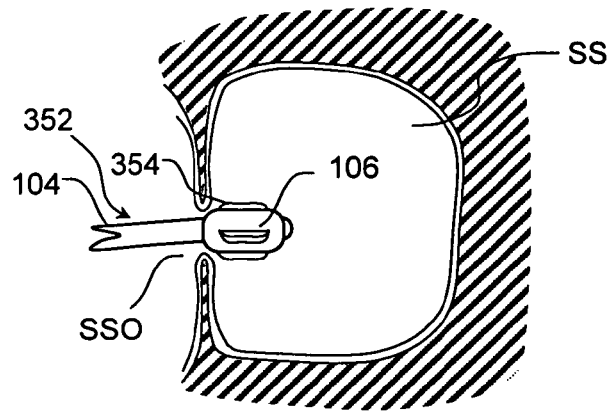
Figure 6:
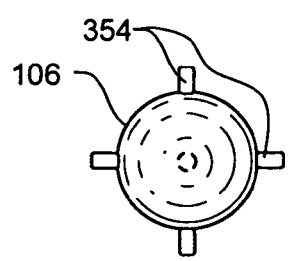
Figure 6:
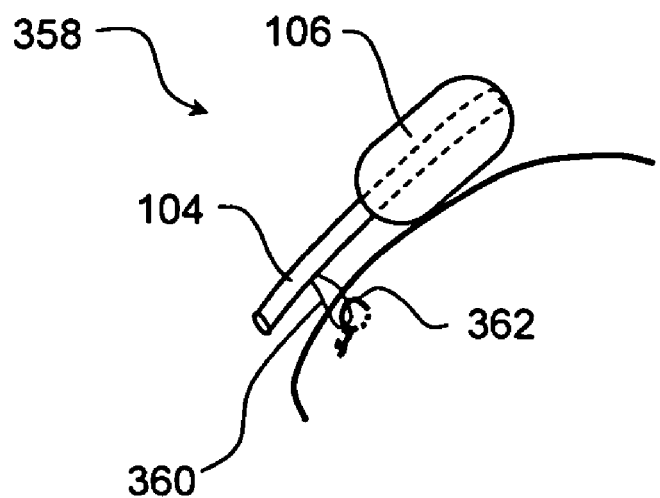
Figure 6:
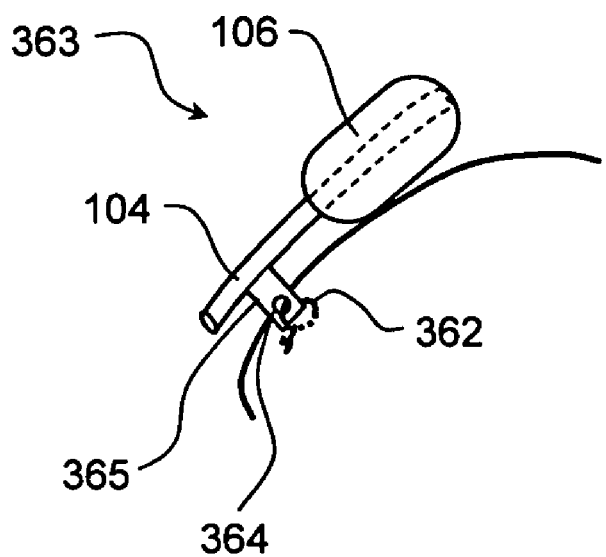
Figure 6:
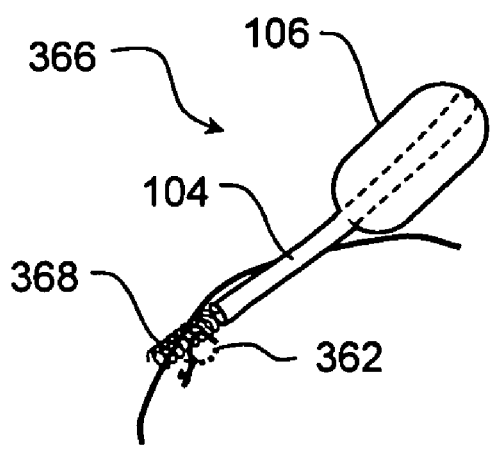
Figure 7:
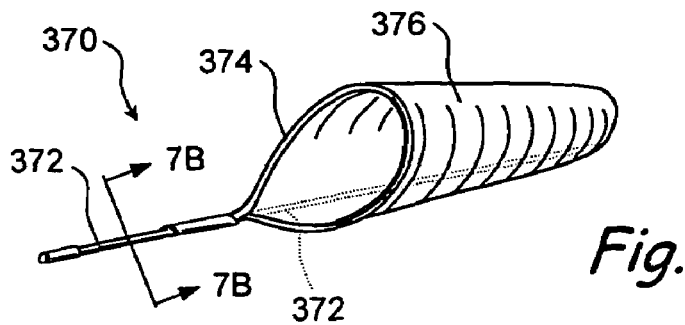
FIG. 7A shows a perspective view of an embodiment of a substance delivery device comprising an elastic, super-elastic or shape-memory material.
FIG. 7B shows a cross section through shaft 652 of substance delivery device 650 of FIG. 7A through the plane 7B-7B.
FIG. 7C shows the substance delivery device of FIG. 7A loaded on a delivery device.
FIG. 7D shows a cross section through the plane 7D-7D of FIG. 7B
FIG. 7E shows the substance delivery device of FIG. 7A loaded on the delivery device of FIG. 7C being introduced through an elongate introducing device.
Figure 7:
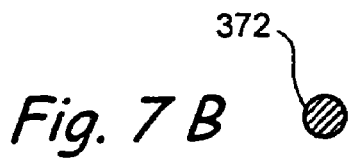
Figure 7:
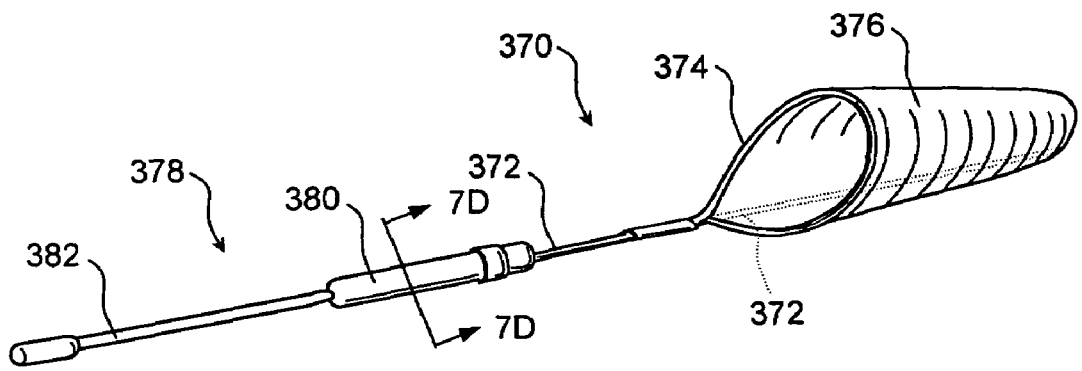
Figure 7:
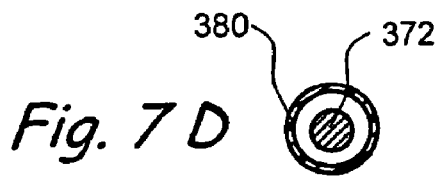
Figure 7:
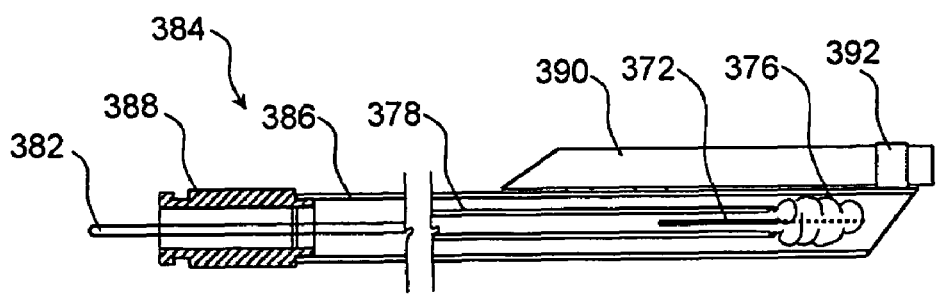

FIG. 5D shows a cross sectional view of an embodiment of a substance delivery device comprising the porous tube 302 of FIG. 5C. Substance delivery device 308 comprises a substance reservoir. In the embodiment shown in FIG. 5D, the substance reservoir is an inflatable balloon 106. Inflatable balloon 106 may be made of suitable compliant or semi-compliant biocompatible materials. Examples of such materials include, but are not limited to polyurethane, silicone, Nylon, polyethylene, PVC, etc. Inflatable balloon 106 is inflated through an elongate shaft 310 comprising a reservoir filling lumen. Elongate shaft 310 comprises a proximal opening 312 that creates a fluid communication between the lumen of elongate shaft 310 and inflatable balloon 106. The lumen of elongate shaft 310 further comprises a plugging mechanism e.g. a one way valve. The plugging mechanism is located proximal to proximal opening 312. The plugging mechanism prevents the backflow of fluid along the proximal direction after a user fills inflatable balloon 106 with a suitable fluid substance through the lumen of elongate shaft 310. Elongate shaft 310 further comprises a distal opening 314 that creates another fluid communication between the lumen of elongate shaft 310 and inflatable balloon 106. Distal opening 314 is located distal to proximal opening 312 as shown in FIG. 5D. The inner diameter of the lumen of elongate shaft 310 is slightly larger than the outer diameter of porous tube 302. This allows porous tube 302 to be inserted into elongate shaft 310 through the distal end of elongate shaft 310 as shown in FIG. 5D. Porous tube 302 is positioned relative to elongate shaft 310 such that plug 304 is located between distal opening 314 and proximal opening 312. Thereafter, porous tube 302 is attached to elongate shaft 310. A fluid substance present in inflatable balloon 106 can flow through distal opening 314 and thereafter through the walls of porous tube 302 and thereafter through the distal end of porous tube 302. Thus, substance delivery device 308 can be used to deliver a fluid substance to the surrounding anatomy at a controlled rate that is controlled by the design of porous tube 302. Substance delivery device 308 may adapted to be inserted into an anatomical region such as a paranasal sinus along an introducing device. Examples of such introducing devices include, but are not limited to guidewires, guide catheters, etc. In the example shown in FIG. 5D, substance delivery device 308 further comprises a second elongate shaft 316 comprising a lumen. Second elongate shaft 316 is attached to elongate shaft 310 such that second elongate shaft 316 is substantially parallel to elongate shaft 310. The lumen of second elongate shaft 316 acts as a rapid-exchange lumen to allow a user to advance substance delivery device 316 into the anatomy over a suitable guidewire.

FIG. 5E shows a cross sectional view of an embodiment of a substance delivery device comprising a porous shaft region for controlled delivery of a substance to the anatomy. Substance delivery device 318 comprises a substance reservoir. In the embodiment shown in FIG. 5E, the substance reservoir is an inflatable balloon 106. Inflatable balloon 106 may be made of suitable compliant or semi-compliant biocompatible materials. Examples of such materials include, but are not limited to polyurethane, silicone, Nylon, polyethylene, PVC, etc. Inflatable balloon 106 is inflated through an elongate shaft 104 comprising a substance introducing lumen 320. The distal end of elongate shaft 104 terminates within inflatable balloon 106 to create a fluid communication between the lumen 320 and inflatable balloon 106. Lumen 320 may be used to introduce a fluid substance into inflatable balloon 106. Lumen 320 further comprises a plugging mechanism e.g. a one way valve. The plugging mechanism prevents the backflow of fluid along the proximal direction after a user fills inflatable balloon 106 with a suitable fluid substance through lumen 320. Substance delivery device 318 may adapted to be inserted into an anatomical region such as a paranasal sinus along an introducing device. Examples of such introducing devices include, but are not limited to guidewires, guide catheters, etc. In the example shown in FIG. 5E, substance delivery device 318 further comprises a second elongate shaft 124 comprising a lumen 322. A region of second elongate shaft 124 is attached to elongate shaft 104 such that second elongate shaft 124 is substantially parallel to elongate shaft 104. Thus, lumen 322 can be used as a rapid-exchange lumen to allow a user to advance substance delivery device 318 into the anatomy over a suitable guidewire. Substance delivery device 318 further comprises a third elongate shaft 324. Third elongate shaft 324 is coaxial to second elongate shaft 124 as shown in FIG. 5E. Third elongate shaft 324 may be made of suitable biocompatible materials including, but not limited to silicone, Pebax, PEEK, Nylon, polyethylene, polyurethane, etc. Third elongate shaft 324 and second elongate shaft 124 enclose a lumen 328. The proximal end of lumen 328 is plugged with an annular plug 326 as shown in FIG. 5E. Third elongate shaft 324 comprises one or more pores that create a fluid communication between inflatable balloon 106 and lumen 328. The one or more pores may have a pore size ranging from 0.2 microns to 200 microns. A fluid substance present in inflatable balloon 106 can flow through the porous walls of third elongate shaft 324 and thereafter through the distal end of lumen 328. Thus, substance delivery device 318 can be used to deliver a fluid substance to the surrounding anatomy at a controlled rate that is controlled by the porous walls of third elongate shaft 324.

FIG. 5F shows a cross section of the substance delivery device of FIG. 5E through the plane 5F-5F. FIG. 5F shows second elongate shaft 124 enclosing lumen 322. Also shown is third elongate shaft 324 coaxial to second elongate shaft 124. Third elongate shaft 324 and second elongate shaft 124 enclose lumen 328.

In an alternate embodiment, the controlled substance release mechanism comprises a diffusion barrier. The diffusion barrier is in fluid communication with a substance stored in a substance reservoir. The substance diffuses through the diffusion barrier and into the surrounding over a period of time.

The substance delivery devices disclosed herein may comprise one or more anchoring or retention elements to secure the position of the substance delivery devices relative to the anatomy. In some embodiments, the one or more substance reservoirs may act as the anchoring or retention elements. For example, in one embodiment of a substance delivery device comprising an inflatable substance reservoir, the inflatable substance reservoir is located within a paranasal sinus. The size of the inflated inflatable substance reservoir is greater than the size of the ostium of the paranasal sinus. This prevents or minimizes the risk of the inflatable substance reservoir sliding out of the paranasal sinus. The inflatable substance reservoir may comprise a shape specially designed to prevent or minimize the risk of the inflatable substance reservoir sliding out of the paranasal sinus. Examples of such shapes include, but are not limited to the inflatable reservoir shapes shown in FIGS. 4F-4J.

The one or more anchoring or retention elements may be present on the shafts of the substance delivery devices disclosed herein. Examples of such anchoring or retention elements are shown in FIGS. 6A-6E'. FIG. 6A shows an embodiment of a substance delivery device comprising an anchoring or retention element comprising deployable arms. Substance delivery device 334 of FIG. 6A comprises an elongate shaft 104 connected to a substance reservoir 106. Substance delivery device 334 further comprises an outer sheath 336 that slides over elongate shaft 104. One or more deployable arms 338 are connected to outer sheath 336 and elongate shaft 104. In the embodiment shown in FIG. 6A, substance delivery device 334 comprises two deployable arms 338. Each deployable arm 338 comprises a bent, curved or angled region. The distal end of each deployable arm 338 is connected to elongate shaft 104. The proximal end of each deployable arm 338 is connected to a distal region of outer sheath 336. Deployable arms 338 may be made of suitable elastic materials including, but not limited to metals such as Nitinol, stainless steel, etc.; polymers such as Nylon, PET, Pebax, PEEK, etc. Deployable arms 338 assume a bent configuration in the relaxed state. In this configuration, a bent region of deployable arms 338 extends in a radially outward direction as shown in FIG. 6A'. This increases the profile of substance delivery device 334, thereby preventing substance delivery device 334 from slipping out of an anatomical region such as a paranasal sinus. A user can temporarily reduce the profile of substance delivery device 334 by pulling outer sheath 336 in the proximal direction relative to elongate shaft 104. This causes deployable arms 338 to get stretched along the axis of substance delivery device 334, thereby reducing the profile of substance delivery device 334. Substance delivery device 334 can be inserted into or removed from an anatomical region in this configuration. FIG. 6A' shows substance delivery device 334 of FIG. 6A deployed in a sphenoid sinus.

FIG. 6B shows a perspective view of an embodiment of a substance delivery device comprising a bent or angled shaft. Substance delivery device 340 of FIG. 6B comprises an elongate shaft 342 connected to a substance reservoir 106. Elongate shaft 342 may be made of suitable elastic materials including, but not limited to Pebax, Nylon, polyethylene, etc. A region of elongate shaft 342 comprises a bent or angled region as shown in FIG. 6B. The bent or angled region increases the profile of substance delivery device 340, thereby preventing substance delivery device 340 from slipping out of an anatomical region such as a paranasal sinus. A user may temporarily reduce the profile of substance delivery device 340 by using a suitable device such as a stylet, guidewire, guide catheter, etc. to temporarily straighten elongate shaft 342. The user may then introduce substance delivery device 340 into a region of the anatomy. The user may remove substance delivery device 340 from the anatomy by pulling elongate shaft 342 in the proximal direction with a force sufficient to cause elongate shaft 342 to temporarily straighten. FIG. 6B' shows substance delivery device 340 of FIG. 6B deployed in a sphenoid sinus.

FIG. 6C shows a perspective view of an embodiment of a substance delivery device comprising a shaft comprising a curved or coiled region. Substance delivery device 344 of FIG. 6C comprises an elongate shaft 346 connected to a substance reservoir 624. Elongate shaft 346 may be made of suitable elastic materials including, but not limited to Pebax, Nylon, polyethylene, etc. A region of elongate shaft 346 comprises a curved or coiled region as shown in FIG. 6C. The curved or coiled region increases the profile of substance delivery device 344, thereby preventing substance delivery device 344 from slipping out of an anatomical region such as a paranasal sinus. A user may temporarily reduce the profile of substance delivery device 344 by using a suitable device such as a stylet, guidewire, guide catheter, etc. to temporarily straighten elongate shaft 342. The user may then introduce substance delivery device 344 into a region of the anatomy. The user may remove substance delivery device 344 from the anatomy by pulling elongate shaft 346 in the proximal direction with a force sufficient to cause elongate shaft 346 to temporarily straighten. FIG. 6C' shows substance delivery device 344 of FIG. 6C deployed in a sphenoid sinus.

FIG. 6D shows a perspective view of an embodiment of a substance delivery device comprising an elongate shaft comprising flexible, projections. Substance delivery device 348 of FIG. 6D comprises an elongate shaft 104 connected to a substance reservoir 106. Elongate shaft 104 may be made of suitable materials including, but not limited to metals such as Nitinol, stainless steel, etc.; polymers such as Nylon, PET, Pebax, PEEK, polyethylene, silicone, etc. A region of elongate shaft 104 comprises one or more projections or arms 350. The one or more projections or arms 350 may be made of suitable flexible, biocompatible materials including, but not limited to metals such as Nitinol, stainless steel, etc.; polymers such as Nylon, PET, Pebax, PEEK, polyethylene, silicone, etc. The one or more projections or arms 350 extend in a radially outward direction from elongate shaft 104. This increases the profile of substance delivery device 348. Substance delivery device 348 may be inserted through an anatomical opening by pushing substance delivery device 348 with a sufficient force in the distal direction. This force bends the one or more projections or arms 350 and thus reduces the profile of substance delivery device 348. After substance delivery device 348 is inserted through the anatomical opening, the one or more projections or arms 350 extend in a radially outward direction and prevent slipping of substance delivery device 348 out of the anatomical opening. Substance delivery device 348 may be removed through the anatomical opening by pulling substance delivery device 348 with a sufficient force in the proximal direction. FIG. 6D' shows substance delivery device 348 of FIG. 6D deployed in a sphenoid sinus.

The substance delivery devices disclosed herein may comprise one or more anchoring or retention elements located on the substance reservoirs. Such anchoring or retention elements help to secure the position of the substance delivery devices relative to the anatomy. Such anchoring or retention elements may also help to maintain a particular position of the substance reservoir relative to an anatomical region to allow the natural flow of anatomical fluids around the substance reservoirs. For example, FIG. 6E shows a perspective view of an embodiment of a substance delivery device comprising a substance reservoir having one or more radial projections. Substance delivery device 352 of FIG. 6E comprises an elongate shaft 104 connected to a substance reservoir 106. Elongate shaft 104 may be made of suitable materials including, but not limited to metals such as Nitinol, stainless steel, etc.; polymers such as Nylon, PET, Pebax, PEEK, polyethylene, silicone, etc. Substance reservoir 106 comprises one or more radial projections or arms 354. The one or more projections or arms 354 may be made of suitable flexible, biocompatible materials including, but not limited to polymers such as Nylon, PET, Pebax, PEEK, polyethylene, silicone, etc. The one or more projections or arms 354 extend in a radially outward direction substance reservoir 106. This increases the profile of substance reservoir 106 after substance reservoir 106 is filled with a suitable substance. Substance delivery device 352 may be inserted through an anatomical opening by pushing substance delivery device 352 with a sufficient force in the distal direction. Thereafter, substance reservoir 106 is filled with a suitable substance. One or more projections or arms 354 extend in a radially outward direction and prevent slipping of substance delivery device 352 out of the anatomical opening. FIG. 6E' shows substance delivery device 352 of FIG. 6E deployed in a sphenoid sinus. In FIG. 6E', projections or arms 354 cause substance reservoir 352 to be positioned at a particular distance away from the sphenoid sinus ostium SSO. This prevents substance reservoir 354 from blocking the natural flow of mucous through the sphenoid sinus ostium.

The substance delivery devices disclosed herein may be sutured to an anatomical region to secure the position of the substance delivery devices relative to the anatomical region. This may be achieved by passing a suture through one or more suturing arrangements present on the substance delivery devices. Examples of such suturing arrangements are shown in FIGS. 6F-6H.

FIG. 6F shows a perspective view of an embodiment of a substance delivery device comprising a suturing arrangement comprising a loop. Substance delivery device 358 of FIG. 6F comprises an elongate shaft 104 and a substance reservoir 106 located on the distal region of shaft 104. Shaft 104 further comprises a loop 360. A user can pass a suitable suture 362 through loop 360 and secure substance delivery device 358 to an anatomical region. Suture 362 may be biodegradable or non-biodegradable.

FIG. 6G shows a perspective view of an embodiment of a substance delivery device comprising a suturing arrangement comprising an aperture. Substance delivery device 358 of FIG. 6G comprises an elongate shaft 104 and a substance reservoir 106 located on the distal region of shaft 104. Shaft 104 further comprises one or more apertures 364. In the embodiment shown in FIG. 6G, the one or more apertures 364 are located on a rectangular tab 365 attached to a region of shaft 104. A user can pass a suitable suture 362 through one or more apertures 364 and secure substance delivery device 363 to an anatomical region. In an alternate embodiment, one or more apertures 364 are located on a region of shaft 104. Suture 362 may be biodegradable or non-biodegradable.

FIG. 6H shows a perspective view of an embodiment of a substance delivery device comprising a suturing arrangement comprising a coiled, twisted or bent region. Substance delivery device 366 of FIG. 6H comprises an elongate shaft 104 and a substance reservoir 106 located on the distal region of shaft 104. Shaft 104 further comprises a coiled, twisted or bent region 368. In the embodiment shown in FIG. 6H, coiled, twisted or bent region 368 is a spring attached to a proximal region of shaft 104. A user can pass a suitable suture 362 around coiled, twisted or bent region 368 and secure substance delivery device 366 to an anatomical region. Suture 362 may be biodegradable or non-biodegradable.

One or more of the substance delivery devices disclosed herein may comprise an elastic, super-elastic or shape-memory material. Such an elastic, super-elastic or shape-memory material may be used to temporarily reduce the profile of the substance delivery devices while they are being inserted or removed through the anatomy. For example, FIG. 7A shows a perspective view of an embodiment of a substance delivery device comprising an elastic, super-elastic or shape-memory material. Substance delivery device 370 of FIG. 7A comprises an elongate shaft 372. Shaft 372 has a sufficient strength to allow a user to pull substance delivery device 370 out of an anatomical region after substance delivery device 370 has been placed in that anatomical region.

Shaft 372 may be made of suitable biocompatible materials including, but not limited to polymers such as polyethylene, Pebax, PEEK, etc.; metals or metals alloys such as stainless steel, nickel-titanium alloys, titanium, etc. Substance delivery device 370 further comprises a loop 374 located on the distal region of shaft 372. Loop 374 can be made from suitable elastic, super-elastic or shape-memory materials including, but not limited to polymers; metals or metals alloys such as stainless steel, nickel-titanium alloys, titanium, etc. A region of loop 374 is attached to a distal region of shaft 372 as shown in FIG. 7A. During the insertion of substance delivery device 370 into the anatomical region or removal of substance delivery device 370 from the anatomical region, loop 374 may temporarily deform or bend to reduce the profile of substance delivery device 370. After insertion of substance delivery device 370 into the anatomical region or removal of substance delivery device 370 from the anatomical region, loop 374 substantially regains its original shape and orientation. Substance delivery device 370 further comprises a cup shaped membrane 376. Membrane 376 may be coated or impregnated with one or more substances to be delivered to the surrounding anatomy. Membrane 376 is attached to substance delivery device 370 such that loop 374 is attached to the rim of the cup shaped membrane 376. The concave surface of membrane 376 faces the proximal direction and the convex surface of membrane 376 faces the distal direction. Membrane 376 may be made of suitable biocompatible materials including, but not limited to polyurethane, Nylon, polyethylene, silicon, etc. FIG. 7B shows a cross section through shaft 372 of substance delivery device 370 of FIG. 7A through the plane 7B-7B.

FIG. 7C shows a perspective view of the substance delivery device of FIG. 7A loaded on a delivery device. Delivery device 378 comprises a distal hollow tube 380. The inner diameter of distal hollow tube 380 is larger than the outer diameter of shaft 372. This allows a proximal region of shaft 372 to be introduced into hollow tube 380 as shown in FIG. 7C. Delivery device 378 further comprises an elongate pusher 382 attached to the proximal region of distal hollow tube 380. During a method of deploying substance delivery device 370 into an anatomical region, a user pushes pusher 382 in the distal direction. This in turn causes the distal end of distal hollow tube 380 to push substance delivery device 370 into the anatomical region. FIG. 7D shows a cross section through the plane 7D-7D of FIG. 7C showing shaft 372 of substance delivery device 370 of FIG. 7A enclosed by distal hollow tube 380 of delivery device 378.

Substance delivery device 370 and delivery device 378 may be introduced into the anatomy through one or more introducing devices. For example, FIG. 7E shows substance delivery device 370 of FIG. 7A loaded on delivery device 378 of FIG. 7C being introduced through a guide catheter 384. Guide catheter 384 comprises an elongate hollow introducing shaft 386. The diameter of the lumen of introducing shaft 386 is larger than the outer diameter of delivery device 378. This allows a user to introduce delivery device 378 through the lumen of introducing shaft 386. Substance delivery device 370 may be present in a collapsed or folded state within introducing shaft 386 and thereafter expand or unfold after being placed in a desired anatomical region. The proximal end of introducing shaft 386 may comprises a suitable hub such as a female luer lock 388. Guide catheter 384 may in turn be introduced over a guidewire into an anatomical region. In the embodiment shown in FIG. 7E, guide catheter 384 further comprises a rapid exchange lumen located on a short tube 390 attached to a distal region of introducing shaft 386. The distal end of tube 390 and/or introducing shaft 386 may comprise a radio-opaque marker 392 such as a radio-opaque marker band to enable the user to track guide catheter 384 using X-rays. The distal end of tube 390 and/or introducing shaft 386 may comprise an atraumatic tip to reduce or prevent damage to anatomical structures by the distal end of guide catheter 384.

One or more of the substance delivery devices disclosed herein may comprise an elongate filament, coil or wire. Such substance delivery devices may be introduced in an anatomical region through a suitable introducing device. Such substance delivery devices may be fully or partially biodegradable or non-biodegradable. Such substance delivery devices may comprise an elastic, super-elastic or shape-memory material to enable the substance delivery devices to assume a two or three dimensional shape after being deployed in an anatomical region. For example, FIG. 8A shows an embodiment of an elongate substance delivery device comprising an elongate filament being introduced in a sphenoid sinus. Substance delivery device 394 comprises an elongate filament can be introduced into a suitable anatomical region such as a paranasal sinus to deliver one or more substances. The diameter of substance delivery device 394 may range from 0.01 to 1 mm. This size allows mucous or other anatomical fluids to flow around substance delivery device 394 and out of a paranasal sinus when substance delivery device 394 is inserted into the paranasal sinus. Substance delivery device 394 can be delivered by a user into an anatomical region through a hollow introducing device 396. In the embodiment shown in FIG. 8A, introducing device 396 comprises a hollow, elongate shaft 398 and a suitable hub 400 connected to the proximal end of elongate shaft 398. FIG. 8B shows a cross sectional view through a region of substance delivery device 394 of FIG. 8A through plane 8B-8B. In the embodiment shown, substance delivery device 394 comprises an inner filament 402. Filament 402 may be made of suitable biocompatible materials such as various biodegradable or non-biodegradable suture materials. Examples of such materials include, but are not limited to poly-glycolic acid poly-L-lactic acid, poly-dioxanone, polyglyconate, Nylon, polyester, polypropylene, etc. Filament 402 may be manufactured by extrusion or drawing. Filament 402 is coated with a basecoat. The basecoat in turn is dip coated or spray coated with a matrix layer 404 comprising a substance to be delivered to the surrounding anatomy. Matrix layer 404 in turn may be coated with a topcoat 406 to control diffusion and release rate of the substance in matrix layer 404. In one embodiment, topcoat 406 is made of PBMA or phosphatidylcholine and the substance in matrix layer 404 is a steroid, antibiotic or an anti-fungal agent. In this embodiment, substance delivery device 394 is delivered through an opening of a paranasal sinus such that at least one region of substance delivery device 394 touches a region of the mucosa of the paranasal sinus.

Figure 9A:
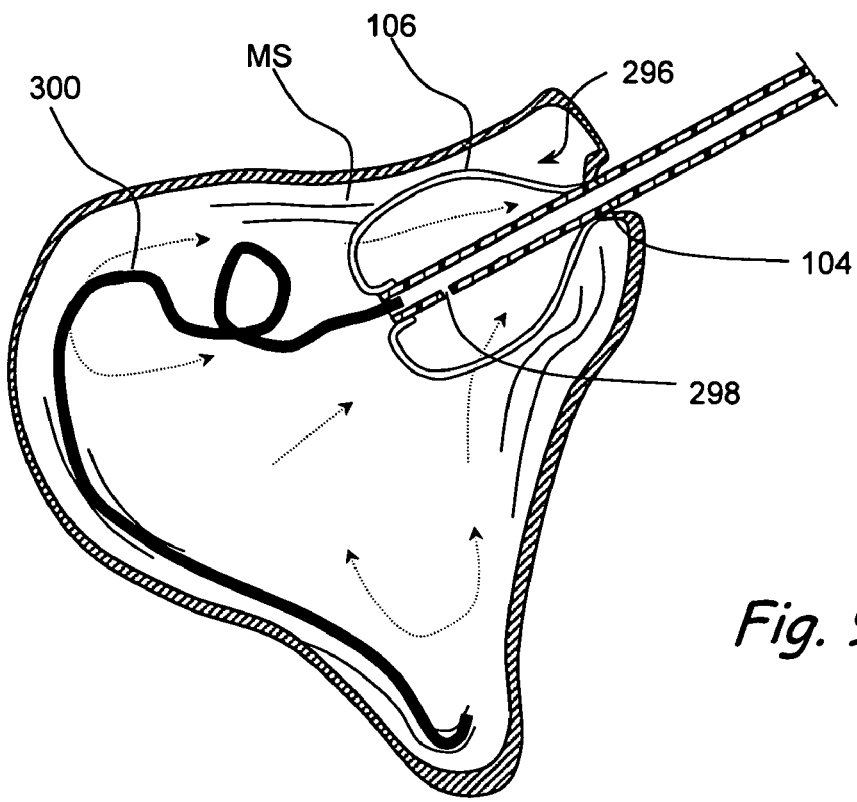
FIG. 9A shows a method of delivering a substance to the lateral wall of a maxillary sinus by the substance delivery device of FIG. 5B.

Several anatomical regions are lined by a layer of mucous that flows in a particular flow path. The devices and methods described herein may be used to selectively deliver a substance to an upstream region on the mucous flow path. This upstream region may be chosen such that the mucous flow delivers the substance throughout the anatomical region. For example, FIG. 9A shows a method of delivering a substance to the lateral wall of a maxillary sinus by the substance delivery device 296 of FIG. 5B. Wick 300 of substance delivery device 296 touches the mucous layer on the lateral wall of the maxillary sinus. Thereafter, the substance in inflatable balloon 106 is delivered by wick 300 to the mucous on the lateral wall of the maxillary sinus at a controlled rate. The substance is then transported along with the mucous flow to cover the entire inner wall of the maxillary sinus as shown in FIG. 9A.

Figure 9B:
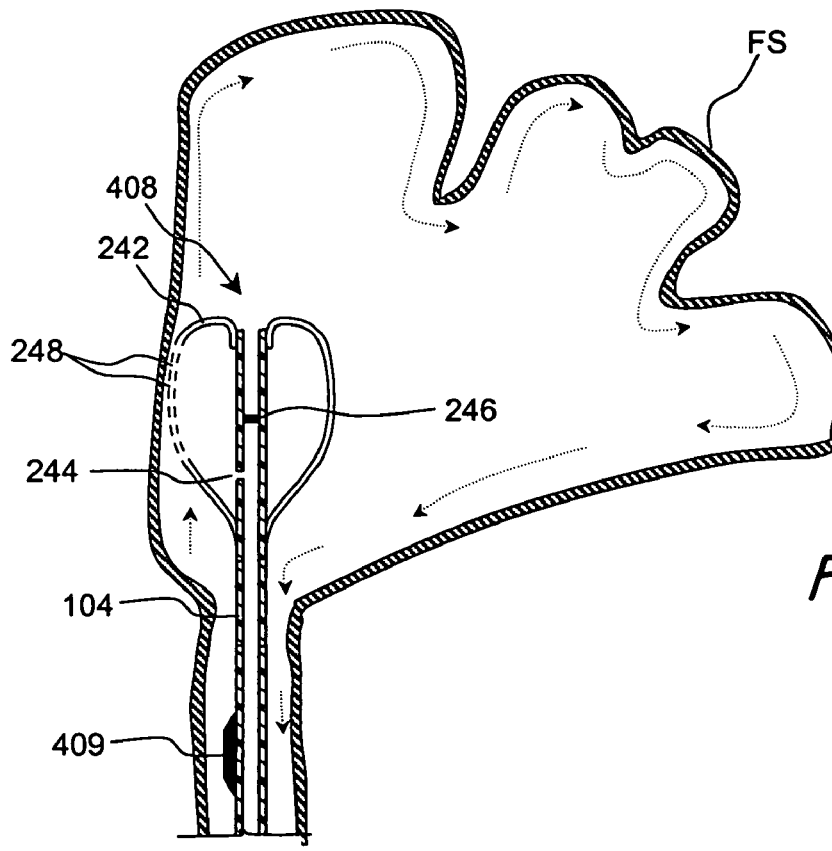
FIG. 9B shows a method of delivering a substance to the medial wall of a frontal sinus by a device similar to the substance delivery device of FIG. 4L.
Figure 10:
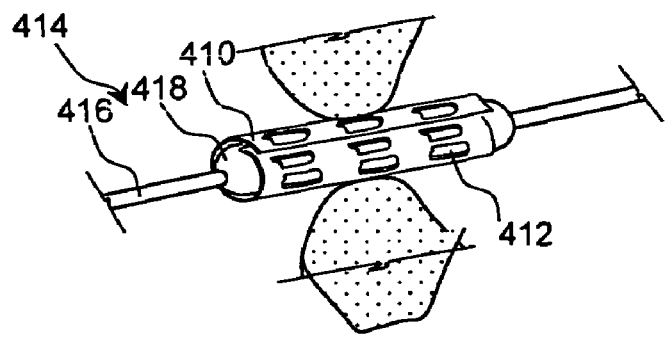
FIGS. 10A through 10C show the various steps of a method of implanting a substance delivering stent in an anatomical region.
FIG. 10D shows a cross section through a region 10D of an embodiment of the device of FIG. 10C.
Figure 10:
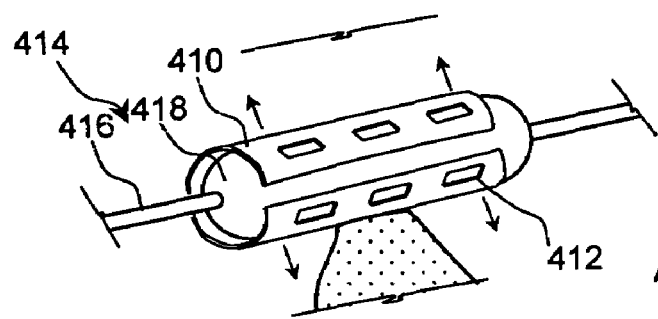
Figure 10:
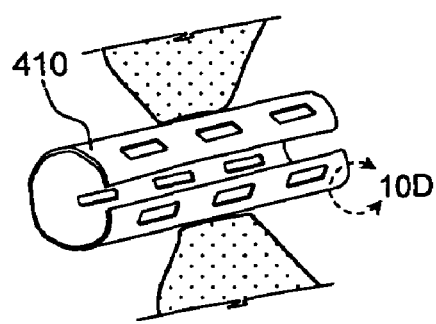
Figure 10:
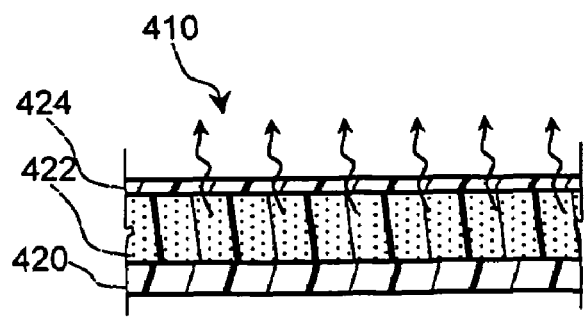
Figure 11:
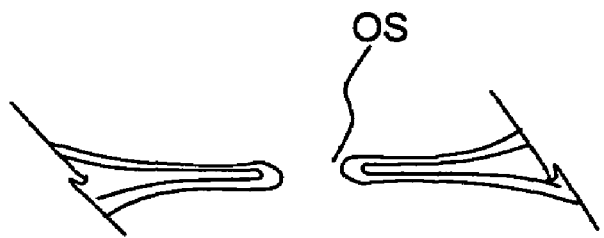
FIGS. 11A through 11C show a sequence of steps to deliver a substance delivery device through a sinus ostium that prevents post-surgical adhesions and also allows the natural flow of mucous through the sinus ostium.
Figure 11:
Figure 11:
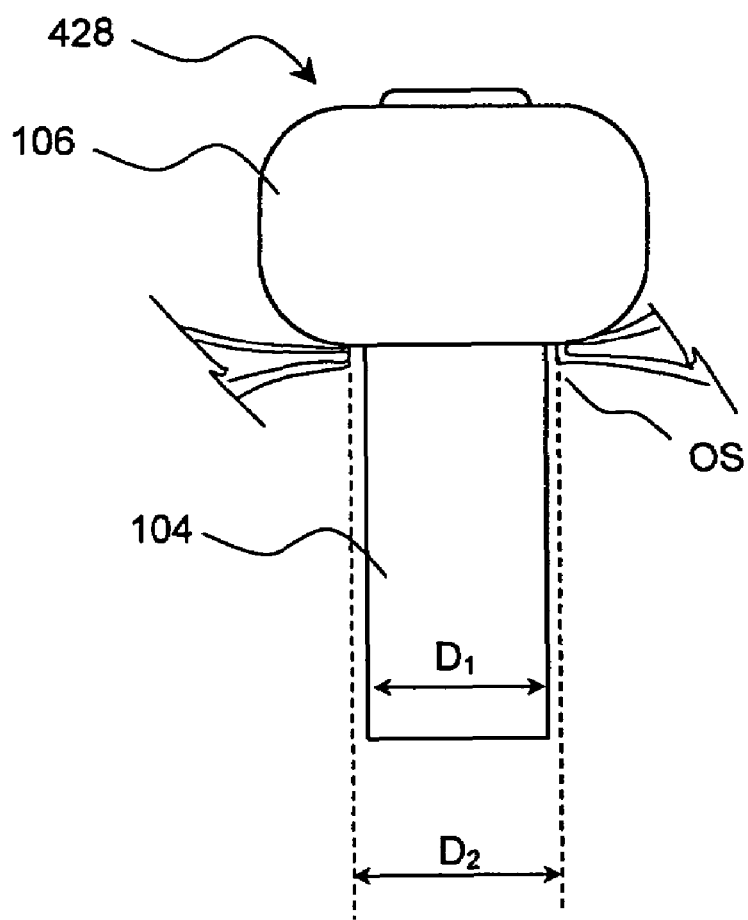

In another example, FIG. 9B shows a method of delivering a substance to the medial wall of a frontal sinus by a device similar to the substance delivery device of FIG. 4L. Substance delivery device 408 of FIG. 9B is similar to substance delivery device 240 of FIG. 4L. Substance delivery device 408 comprises an inflatable balloon 242 that acts as a substance reservoir. Inflatable balloon 242 further comprises one or more pores 248. One or more pores 248 are located only on one side of inflatable balloon 242. One or more pores 248 are oriented so that they deliver the substance stored in inflatable balloon 242 at a controlled rate to the mucous layer on the medial wall of a frontal sinus as shown in FIG. 9B. The substance is then transported along with the mucous flow to cover the entire inner wall of the frontal sinus as shown in FIG. 9B. Substance delivery device 408 further comprises an orientation marker to ensure that one or more pores 248 face the medial wall of the frontal sinus. In the embodiment shown in FIG. 9B, the orientation marker comprises a radiopaque marker 409 located on elongate shaft 104. Radiopaque marker 409 and one or more pores 248 are located in the same radial direction from the axis of elongate shaft 104. This enables a user to orient one or more pores 248 to face the medial wall of the frontal sinus under radiographic visualization.

One or more of the elongate devices disclosed herein may be used as stents. The stents may be positioned within natural or man-made openings to the frontal, maxillary, sphenoid, anterior or posterior Ethmoid sinuses; other cells or cavities; anatomical regions such as nostrils, nasal cavities, nasal meatus, etc.; and other passageways such as Eustachian tubes, naso-lachrymal ducts, etc.

For example, one or more of the elongate devices disclosed herein may be used as sinus stents. Sinus stents are used to prevent adhesions between mucosal surfaces that have been cut during surgical procedures such as FESS. Current sinus stents are bulky. They are difficult to insert and remove. Also, they are difficult to insert through small openings. Therefore low profile stents are needed to minimize invasiveness during insertion, removal and during the period they are implanted. One or more of the elongate devices disclosed herein including, but not limited to the devices illustrated in FIGS. 1, 2A, 4E, 4E' and 4M may be used as sinus stents. Such sinus stents may comprise one or more anchors or other mechanisms to secure the position of the sinus stents in the anatomy. Such sinus stents may for example be placed in anterior or posterior Ethmoid ostia or artificial openings leading to Ethmoid sinuses, natural or surgically created openings to other paranasal sinuses, etc. The step of placement of such sinus stents may be preceded by a step of surgically modifying an anatomical region. For example, a user may surgically create an artificial opening to the Ethmoid sinuses and thereafter place a sinus stent through the artificial opening.

FIGS. 10A through 10C show the various steps of a method of implanting a substance delivering stent in an anatomical region. The stent may be biodegradable or non-biodegradable. In one embodiment of a biodegradable stent, the stent is made of a combination of PLLA and PGA. In another embodiment of a biodegradable stent, the stent is made of a combination of mometasone furoate and poly(ester urethane) multi-block copolymers. The poly(ester urethane) multi-block copolymers may be made by combining different combinations of DL-lactide, glycolide, ε-caprolactone and polyethylene glycol. The stent may be made of a rolled sheet of a material or a tube. In the example shown in FIG. 10A, stent 410 comprises a rolled sheet of a biocompatible material. The rolled sheet comprises one or more substances to be delivered to an anatomical region where stent 410 is delivered. Stent 410 may comprise one or more windows or slots 412 that allow a fluid to pass through the wall of stent 410. Such a stent 410 does not substantially disrupt the normal drainage of anatomical fluids in the anatomical region. Stent 410 may be used to deliver steroids or other substances to anatomical regions including, but not limited to sinus ostia and/or passageways over a desired period of time. In one embodiment, stent 410 is a self-expanding stent. Such as self-expanding stent 410 may be introduced through a hollow guide or sheath into an anatomical region. Stent 410 may be pushed out of the hollow sheath or guide by a pusher. In the method embodiment shown in FIGS. 10A through 10C, stent 410 is a balloon-expandable stent inserted in an anatomical region by a balloon catheter 414. Balloon catheter 414 comprises an elongate shaft 416 and an inflatable balloon 418 on the distal end of elongate shaft 416. Inflatable balloon 418 may be made of suitable compliant, non-compliant or semi-compliant materials. Stent 410 is tightly rolled on the surface of inflatable balloon 418. This reduces the profile of stent 410. Balloon catheter 414 and stent 410 are inserted into an anatomical region. In FIG. 10A, an ostium of a paranasal sinus is used as an example of the anatomical region. In FIG. 10B, inflatable balloon 418 is inflated by a user. This causes stent 410 to expand as shown in FIG. 10B. In one embodiment, inflatable balloon 418 is also used as a dilating balloon to dilate the anatomical region. Thereafter, inflatable balloon 418 is deflated. This causes stent 410 to separate from balloon catheter 414. Thereafter, as shown in FIG. 10C, balloon catheter 414 is removed from the anatomical region. Stent 410 remains in the anatomical region. Stent 410 encloses a hollow region that allows a user to pass a range of devices through the hollow region. Examples of such devices include, but are not limited to guidewires, catheters, flexible scopes and cutters.

In one embodiment, the material of stent 410 comprises a polymer, one or more substances to be delivered and a stabilizer. Stent 410 may be designed to delivery a substance through only one surface of the rolled sheet. FIG. 10D shows a cross section through a region 10D of an embodiment of the device of FIG. 10C. In the embodiment of stent 410 shown in FIG. 10D, the wall of stent 410 comprises three layers. Inner layer 420 is thick and provides mechanical strength to stent 410. In one example, inner layer 420 is made of ethylene vinyl acetate (EVA). Middle layer 422 comprises a suitable substance to be delivered to the surrounding anatomy. In one example, middle layer 422 comprises a mixture of EVA and dexamethasone and polyvinyl pyrrolidone. The substance to be delivered to the surrounding anatomy cannot diffuse through inner layer 420, but can diffuse through an outer layer 424. Outer layer 424 thus controls the rate of release of the substance to the surrounding anatomy. In one example, outer layer is made of EVA. Stent 410 is designed to be easily removable after a desired period of time. Stent 410 may be removed for example by forceps or other grasping devices. In one embodiment, stent 410 comprises a removal element that enables a user to easily remove stent 410 from the anatomy. In one embodiment, the removal element of an elongate string or filament attached to stent 410. A user pulls the elongate string or filament in the proximal direction to remove stent 410 from the anatomical region.

The various substance delivery devices disclosed herein may comprise a hollow tubular region through which anatomical fluids can flow. Such embodiments of substance delivery devices cause minimal or zero disruption to the natural flow of anatomical fluids such as mucous. Such embodiments of substance delivery devices may also be used to prevent adhesions between mucosal surfaces that have been cut during surgical procedures such as FESS. For example, FIGS. 11A through 11C show a sequence of steps to deliver a substance delivery device through a sinus ostium that prevents post-surgical adhesions and also allows the natural flow of mucous through the sinus ostium. FIG. 11A shows a cross section of a sinus ostium OS of a patient with sinusitis. In FIG. 11B, the sinus ostium OS is surgically dilated. This dilation may be performed by a variety of methods including, but not limited to the Balloon Sinuplasty™ procedure, FESS, etc. Thereafter, in FIG. 11C, a substance delivery device 428 is inserted through the sinus ostium OS. Substance delivery device 428 comprises an elongate shaft 104 and a substance reservoir 106. The outer diameter $D_1$ of elongate shaft 104 is slightly smaller than the inner diameter $D_2$ of the dilated sinus ostium OS. This enables a user to introduce substance delivery device 248 through the dilated sinus ostium OS. Elongate shaft comprise an end-to-end lumen. This end-to-end lumen allows the natural flow of mucous generated within the sinus thereby preventing unwanted accumulation of the mucous within the sinus. Elongate shaft 104 also prevents prevent adhesions between mucosal surfaces of the sinus ostium OS that have been dilated thereby acting as a sinus stent.

The stent devices disclosed herein may be retained in the anatomy for a desired time period ranging from approximately 3 days to approximately 4 weeks. Such stents may be implanted in suitable anatomical regions such as surgically enlarged or dilated opening(s) of a paranasal sinus. They may be sized to maintain a desired diameter of said surgically enlarged or dilated opening between about 2 mm and about 10 mm.

The devices and methods disclosed herein may be used to deliver substances to anatomical regions such as paranasal sinuses by dripping and evaporation of the substances. In one method embodiment, dexamethasone is delivered to paranasal sinuses. In this embodiment, dexamethasone is dissolved in a volatile solvent such as ethanol to achieve a solution with a desired dexamethasone concentration (e.g. 10 mg/ml). A substance delivery device such as substance delivery device 240 of FIG. 4L is then inserted into a paranasal sinus. A suitable volume of the solution (e.g. approx. 0.2 ml) is then delivered to inflatable balloon 242 of drug delivery device 240. The solution is then allowed to drip and evaporate slowly through one or more pores 248 located on inflatable balloon 242. The size of one or more pores 248 may range from 20 to 100 microns. Dripping and evaporation of the solution through one or more pores 248 of substance delivery device 240 causes the dexamethasone to be delivered to the inner walls of the paranasal sinuses. Similarly, other devices disclosed herein such as substance delivery device 296 of FIG. 5B may be used to deliver substances to anatomical regions such as paranasal sinuses by dripping and evaporation of the substances.

The devices and methods disclosed herein may be used to deliver gels or viscous liquids comprising one or more substances to anatomical regions such as paranasal sinuses. Such gels or viscous liquids may coat and adhere to a mucous membrane and thus provide sustained delivery of one or more substances to the mucous membrane. In one embodiment, a plasticized hydrocarbon gel comprising gelatin, pectin and sodium carboxymethylcellulose and a suitable substance may be delivered to a mucous membrane such as the mucous membrane of a paranasal sinus. Such gels can be used for sustained delivery of the suitable substance to the mucous membrane.

One or more of the substance reservoirs disclosed herein may comprise multiple compartments such that each compartment stores a particular substance formulation. The multiple compartments prevent mixing of multiple substance formulations before substance formulations are delivered to the anatomy.

One or more of the substance reservoirs comprising pores may be filled with a suitable substance at a sufficiently high pressure to cause a portion of the substance to squirt out of the pores. This process may be used to deliver an initial bolus of the substance to the surrounding anatomy.

One or more of the substance reservoirs disclosed herein may be filled with a suitable substance after the substance reservoir is introduced in an anatomical region. Alternatively, one or more of the substance reservoirs disclosed herein may be filled with a suitable substance before the substance reservoir is introduced in an anatomical region. Alternatively, one or more of the substance reservoirs disclosed herein may be pre-filled with a solid, lyophilized or concentrated substance. The solid, lyophilized or concentrated substance is converted to an active form by introducing a solvent into the substance reservoir. This may be done just before or after the substance reservoir is introduced in an anatomical region. Alternatively, one or more of the substance reservoirs disclosed herein may be pre-filled with an inactive form of a substance. The inactive form of the substance is converted to an active form by introducing an activating agent into the substance reservoir. This may be done just before or after the substance reservoir is introduced in an anatomical region.

The devices and methods disclosed herein may be used to treat middle ear or inner ear pathologies. This may be done by accessing the middle ear through the Eustachian tube or through the tympanum. For example, the devices and methods disclosed herein may be used to treat Meniere's disease by delivering gentamicin to the inner ear through the round window membrane. The devices and methods disclosed herein may be used to treat a variety of diseases or disorders by a variety of substances including, but not limited to the substances and diseases or disorders disclosed in Table 1.

TABLE 1

| ANATOMICAL LOCATION OF THE DISEASE/ DISORDER | DISEASE/DISORDER TO BE TREATED | EXAMPLES OF SUBSTANCES THAT MAY BE DELIVERED |
|---|---|---|
| Inner ear | Meniere's disease, Vertigo | Gentamicin, Vestibular suppressants (e.g. anticholinergics, antihistamines, and benzodiazepines), antiemetic drugs, diuretics, etc. |
| Inner ear | Autoimmune inner ear disease | Corticosteroids, etc. |
| Inner ear | Free radical induced damage | Glutamate antagonists(e.g. memantine, caroverine and magnesium), Calpain inhibitor (e.g. Leupeptin), Antioxidants (e.g. glutathione, Methionine), etc. |
| Inner ear | Hearing loss and tinnitus | Neurotrophic factors (e.g. NeuroTrophin-3), Genes for Neurotrophic factors such as BDNF (brain-derived neurotropic factor), etc. |
| Middle ear | Otitis media | Amoxicillin, ampicillin, azithromycin, cefaclor, cefdinir, ceftibuten, ceftriaxone, erythomycin, clarithromycin, combination of trimethoprim/ sulfamethoxazole, ofloxacin, etc. |
| Inner ear | Degeneration of inner | Grafted neural stem cells, |

TABLE 1-continued

| ANATOMICAL LOCATION OF THE DISEASE/ DISORDER | DISEASE/DISORDER TO BE TREATED | EXAMPLES OF SUBSTANCES THAT MAY BE DELIVERED |
|---|---|---|
| | ear cells, especially sensory hair cells and associated neurons, | embryonic stem cells, dorsal ganglion cells and cell lines derived from fetal inner ear cells, autologous bone marrow stromal cells, etc. |

It is to be further appreciated that, as described herein, the implantable portion of a substance delivery device 100 may include a through lumen that may function as a vent and/or drain when such implantable portion device is in the Eustachian tube or through an opening formed in the tympanum.

The devices and methods disclosed herein may be used to mark an anatomical region with a suitable imageable marker. For example, the devices and methods disclosed herein may be used to deliver a radio opaque marker such as a radio opaque contrast agent to an ostium of a paranasal sinus. This enables a user to image the ostium of the paranasal sinus using X-rays or fluoroscopy.

One or more of the substance delivery devices disclosed herein may comprise a curved, bent or angled region to enable the drug delivery devices to navigate through the anatomy.

The distal-most regions of one or more substance delivery devices disclosed herein may comprise an atraumatic tip. The atraumatic tip is used to prevent or reduce damage to the anatomy by the distal-most regions of the one or more substance delivery devices.

The outer surface of one of more substance delivery devices disclosed herein may comprise a coating that reduces or eliminates the risk of encrusting of the outer surface by a biological material. In one embodiment, the coating comprises a material that absorbs water to form a gel. Examples of such materials include, but are not limited to hyaluronic acid, etc.

One or more of the substance delivery devices disclosed herein may be designed to be easily removable from the anatomy after completion of a treatment.

One or more of the substance delivery devices disclosed herein may be refilled after a significant volume of substance filled in a substance reservoir has been delivered to the anatomy.

One or more of the substance delivery devices disclosed herein may comprise one or more markers to enable a user to locate and/or navigate the substance delivery devices through the anatomy. For example, the substance delivery devices may comprise visual markers to enable the user to determine the depth of insertion of the substance delivery devices into the anatomy. In another example, the substance delivery devices may comprise imaging markers to enable the user to locate and/or navigate the substance delivery devices using imaging modalities such as X-rays, MRI, etc.

As used herein, the term "opening or a paranasal sinus" shall include any transnasally accessible opening in a paranasal sinus or air cell such as natural ostia, surgically altered natural ostia, surgically created openings, antrostomy openings, ostiotomy openings, burr holes, drilled holes, ethmoidectomy openings, natural or man made passageways, etc.

As used herein, the term "implantable" shall include any device that is maintained in the body of a human or animal for a period ranging from 30 minutes to 60 days.

As used herein, the term "porous" shall include any element that comprises one or more pores or apertures.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method for delivering a substance to a location within a head of a subject, said method comprising:
introducing an implantable substance delivery reservoir comprising an expandable reservoir body in an unexpanded configuration through a nostril of the head, wherein the reservoir is removably coupled with an elongate shaft having a lumen in fluid communication with the reservoir;
positioning the implantable reservoir at a desired location within a paranasal sinus or paranasal sinus ostium of the head;
introducing a therapeutic or diagnostic substance, or a component thereof, through the lumen of the elongate shaft and into the reservoir causing expansion of the expandable reservoir body;
detaching the elongate shaft from the implantable reservoir; and
removing the elongate shaft from the head, thus leaving the implantable reservoir behind such that the therapeutic or diagnostic substance will pass out of the reservoir through at least one aperture located in the expandable reservoir body; preventing the diagnostic or therapeutic substance from backflowing out of the reservoir after removal of the elongate shaft.

2. A method according to claim 1, wherein the reservoir, when expanded, engages at least one of a paranasal sinus wall or a paranasal sinus ostium in a manner that deters unwanted movement of the reservoir after it has been implanted.

3. A method according to claim 2, wherein at least a portion of the reservoir is positioned within a paranasal sinus and, when expanded, is too large to pass through an opening of that paranasal sinus, thereby deterring unwanted movement of the reservoir.

4. A method according to claim 1, wherein the implantable reservoir further comprises a reservoir lumen in fluid communication with the lumen of the elongate shaft.

5. A method according to claim 4, wherein the step of preventing backflow comprises clamping, clipping, ligating, tying or compressing the reservoir lumen to prevent substance that has been introduced in the reservoir from backflowing out of the reservoir lumen.

6. A method according to claim 4, wherein the step of preventing backflow comprises allowing, after the substance is introduced into the reservoir, a closure apparatus on the reservoir to automatically close to prevent substance from backflowing out of the reservoir lumen.

7. A method according to claim 6, wherein the closure apparatus comprises a one-way valve.

8. A method according to claim 1, wherein at least one of the implantable reservoir or the elongate shaft comprises at least one imageable marker, and wherein the method further comprises imaging the imageable marker.

9. A method according to claim 1, further comprising using an anchoring apparatus coupled with the implantable reservoir to anchor the implantable reservoir to tissue in the head.

10. A method according to claim 1, wherein the at least one aperture comprises multiple apertures or pores in the expandable reservoir body, and wherein the substance passes out of at least some of the apertures or pores.

11. A method according to claim 10 wherein the substance is a substance that will pass through the pores at a known rate.

12. A method according to claim 1, wherein the implantable reservoir is at least partially biodegradable.

13. A method according to claim 1 wherein the substance is selected from the group consisting of: an imageable contrast agent; a diagnostic indicator agent; an antibiotic; an antifungal; an antiparasitic; an antimicrobial; a steroid; a vasoconstrictor; a leukotriene inhibitor; an IgE inhibitor; an anti-inflammatory; a mast cell stabilizer; an antihistamine; an immunomodulator; an SYK kinase Inhibitor a chemotherapeutic agent; an antineoplastic agent; a mucolytie agent; an agent that thins or otherwise changes the viscosity of mucous; and a substance that facilitates remodeling of soft tissue and/or bone and/or cartilage.

14. A method according to claim 1, wherein the substance comprises a steroid or non-steroidal anti-inflammatory agent.

15. A method according to claim 14, wherein the substance comprises a steroid selected from the group consisting of beclomethasone, flunisolide, fluticasone, triamcinolone, mometasone, aclometasone, desonide, hydro cortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone.

16. A method according to claim 1, wherein the substance comprises an antimicrobial.

17. A method according to claim 16 wherein the antimicrobial is selected from the group consisting of: acyclovir, amantadine, am rimantadine, oseltamivir, zanamivir, inoglycosides, amikacin, gentamicin, tobramycin, amoxicillin, amoxicillin/clavulanate, amphotericin B, ampicillin, ampicillin/sulbactam, atovaquone, azithromycin, cefazolin, cefepime, cefotaxime, cefotetan, cefpdoxime, ceftazidime, ceftizoxime, cefiriaxone, cefuroxime, cefhroxime axetil, cephalexin, chioramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazoic, ketoconazole, metronidazole, nafcillin, nafcillin, nystatin, penicillins including penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triameinolone/nystatin, clotrimazole/betamethasone, clotrimazole, ketoconazole, butoconazole, miconazole, tioconazole, detergent-like chemicals that disrupt or disable microbes, nonoxynol-9, octoxynol-9, benzalkonium chloride, menfegol, and N-docasanol, chemicals that block microbial attachment to target cells, chemical that inhibits entry of infectious pathogens into cells, sulphated polymers, sulponated polymers, carrageenan, antiretroviral agents, PMPA gel, antibodies, genetically engineered or naturally occurring antibodies that combat pathogens, plantibodies, agents which change the condition of the tissue to make it hostile to the microbes, agents which alter mucosal pH, buffer gel, acidform non-pathogenic microbes that kill or inhibit the growth of pathogenic microbes and antimicrobial metals.

18. A method according to claim 1, wherein the implantable reservoir further comprises a tubular member forming a reservoir lumen, wherein introducing the substance or component thereof comprises introducing it through the lumen of the elongate shaft, through the reservoir lumen and through the one-way valve into the reservoir.

19. A method according to claim 1, wherein at least one of the implantable reservoir or the elongate shaft further comprises a guidewire lumen, and wherein the method further comprises, before introducing the reservoir:
    inserting a guidewire into the head; and
    introducing at least one of the reservoir or the shaft over the guidewire.

20. A method according to claim 19, wherein the guidewire lumen extends from a distal opening in the distal end of the reservoir to a proximal opening in the proximal end of the shaft.

21. A method according to claim 19, wherein the guidewire lumen extends from a distal opening in the distal end of the reservoir to a side opening located between proximal and distal ends of the shaft.

22. A method according to claim 1, wherein the implantable reservoir is configured such that, when expanded, a body fluid may flow through or around the implantable reservoir.

23. A method according to claim 1, at least one wicking member coupled with the implantable reservoir for promoting passage of the substance out of the reservoir by a wicking action.

24. A method according to claim 1, wherein detaching the shaft from the reservoir comprises cutting at a junction of the shaft with the reservoir.

25. A method according to claim 1, wherein detaching the shaft from the reservoir comprises cutting the shaft at a location proximal to a junction of the shaft with the reservoir, wherein a distal portion of the shaft is left in the head, coupled with the implantable reservoir.

* * * * *